(12) United States Patent
Wallecha et al.

(10) Patent No.: US 10,258,679 B2
(45) Date of Patent: Apr. 16, 2019

(54) **RECOMBINANT *LISTERIA* VACCINE STRAINS AND METHODS OF PRODUCING THE SAME**

(71) Applicant: ADVAXIS, INC., Princeton, NJ (US)

(72) Inventors: Anu Wallecha, Yardley, PA (US); Robert Petit, Newtown, PA (US)

(73) Assignee: ADVAXIS, INC., Princeton, NJ (US)

( * ) Notice: Subject to any disclaimer, the term of this patent is extended or adjusted under 35 U.S.C. 154(b) by 0 days.

(21) Appl. No.: 15/306,289

(22) PCT Filed: Apr. 14, 2015

(86) PCT No.: PCT/US2015/025690
§ 371 (c)(1),
(2) Date: Oct. 24, 2016

(87) PCT Pub. No.: WO2015/164121
PCT Pub. Date: Oct. 29, 2015

(65) Prior Publication Data
US 2017/0042996 A1 Feb. 16, 2017

Related U.S. Application Data

(60) Provisional application No. 61/983,732, filed on Apr. 24, 2014.

(51) Int. Cl.
*A61K 39/00* (2006.01)
*A61K 39/12* (2006.01)
(Continued)

(52) U.S. Cl.
CPC .......... *A61K 39/0011* (2013.01); *A61K 39/12* (2013.01); *C07K 14/005* (2013.01);
(Continued)

(58) Field of Classification Search
CPC ................ C07K 14/005; C07K 14/705; C07K 2319/00; C07K 14/34; C12N 2760/16122; A61K 39/00
See application file for complete search history.

(56) References Cited

U.S. PATENT DOCUMENTS 5,830,702 A 11/1998 Portnoy et al.
6,051,237 A 4/2000 Paterson
(Continued)

FOREIGN PATENT DOCUMENTS

WO wo 1996/14087 A1 5/1996
WO WO 1999/025376 A1 5/1999
(Continued)

OTHER PUBLICATIONS

Petit et al. "12 Month Survival and Safety Data from a Phase 2 Study in Recurrent Cervical Cancer," 2013 ASCO Annual Meeting, Abstract #5529, May 29, 2013 (May 29, 2013). Retrieved from the Internet:.*
(Continued)

*Primary Examiner* — Jana A Hines
(74) *Attorney, Agent, or Firm* — Alston & Bird LLP

(57) ABSTRACT

The present invention provides methods of treating, protecting against and inducing an immune response against a tumor or cancer, comprising the step of administering to a subject a recombinant *Listeria* strain. In one embodiment the present invention relates to a recombinant *Listeria* strain, said recombinant *Listeria* strain comprising a recombinant nucleic add, said nucleic add comprising a first open reading frame encoding a recombinant polypeptide comprising a first N-terminal fragment of an LLO protein fused to a heterologous antigen or fragment thereof, and wherein said
(Continued)

recombinant nucleic add further comprises a second open reading frame encoding a mutant PrfA protein.

32 Claims, 17 Drawing Sheets

Specification includes a Sequence Listing.

(51) Int. Cl.
*C07K 14/195* (2006.01)
*C12N 1/36* (2006.01)
*C07K 14/005* (2006.01)
*C12N 7/00* (2006.01)

(52) U.S. Cl.
CPC .............. *C07K 14/195* (2013.01); *C12N 1/36* (2013.01); *C12N 7/00* (2013.01); *A61K 2039/522* (2013.01); *A61K 2039/523* (2013.01); *A61K 2039/572* (2013.01); *A61K 2039/585* (2013.01); *C07K 2319/55* (2013.01); *C12N 2710/20034* (2013.01); *C12N 2710/20051* (2013.01)

(56) References Cited

U.S. PATENT DOCUMENTS

| | | |
|---|---|---|
| 6,099,848 A | 8/2000 | Frankel et al. |
| 6,504,020 B1 | 1/2003 | Frankel et al. |
| 6,565,852 B1 | 5/2003 | Paterson |
| 6,635,749 B2 | 10/2003 | Frankel et al. |
| 6,767,542 B2 | 7/2004 | Paterson et al. |
| 6,855,320 B2 | 2/2005 | Paterson et al. |
| 7,135,188 B2 | 11/2006 | Paterson |
| 7,488,487 B2 | 2/2009 | Frankel et al. |
| 7,588,930 B2 | 9/2009 | Paterson et al. |
| 7,635,479 B2 | 12/2009 | Paterson et al. |
| 7,655,238 B2 | 2/2010 | Paterson et al. |
| 7,662,396 B2 * | 2/2010 | Paterson .............. A61K 38/164 424/185.1 |
| 7,700,344 B2 | 4/2010 | Paterson et al. |
| 7,794,729 B2 | 9/2010 | Paterson et al. |
| 7,820,180 B2 | 10/2010 | Paterson et al. |
| 7,855,064 B2 | 12/2010 | Paterson et al. |
| 7,858,097 B2 | 12/2010 | Paterson et al. |
| 8,114,414 B2 | 2/2012 | Paterson et al. |
| 8,241,636 B2 | 8/2012 | Paterson et al. |
| 8,268,326 B2 | 9/2012 | Paterson et al. |
| 8,337,861 B2 | 12/2012 | Paterson et al. |
| 8,771,702 B2 | 7/2014 | Paterson et al. |
| 8,778,329 B2 | 7/2014 | Seavey et al. |
| 8,791,237 B2 | 7/2014 | Paterson et al. |
| 8,906,664 B2 | 12/2014 | Paterson et al. |
| 8,956,621 B2 | 2/2015 | Paterson et al. |
| 9,012,141 B2 | 4/2015 | Paterson et al. |
| 9,017,660 B2 | 4/2015 | Shahabi et al. |
| 9,084,747 B2 | 7/2015 | Shahabi et al. |
| 9,226,958 B2 | 1/2016 | Harn et al. |
| 9,408,898 B2 | 8/2016 | Seavey et al. |
| 9,463,227 B2 | 10/2016 | Rothman et al. |
| 9,492,527 B2 | 11/2016 | Paterson et al. |
| 9,499,602 B2 | 11/2016 | Paterson et al. |
| 9,549,973 B2 | 1/2017 | Paterson et al. |
| 9,644,212 B2 | 5/2017 | Maciag et al. |
| 9,650,639 B2 | 5/2017 | Maciag et al. |
| 9,700,608 B2 | 7/2017 | Paterson et al. |
| 9,919,038 B2 | 3/2018 | Seavey et al. |
| 9,943,590 B2 | 4/2018 | Harn et al. |
| 9,981,024 B2 | 5/2018 | Seavey et al. |
| 10,010,593 B2 | 7/2018 | Paterson |
| 10,016,617 B2 | 7/2018 | Mason et al. |
| 2002/0025323 A1 | 2/2002 | Paterson et al. |
| 2002/0028206 A1 | 3/2002 | Paterson |
| 2002/0136737 A1 | 9/2002 | Frankel et al. |
| 2003/0202985 A1 | 10/2003 | Paterson |
| 2005/0048081 A1 | 3/2005 | Frankel et al. |
| 2005/0118184 A1 | 6/2005 | Paterson et al. |
| 2005/0129715 A1 * | 6/2005 | Paterson .............. C07K 14/005 424/234.1 |
| 2006/0093582 A1 | 5/2006 | Paterson et al. |
| 2006/0104991 A1 | 5/2006 | Paterson et al. |
| 2006/0204516 A1 | 9/2006 | Paterson et al. |
| 2006/0205067 A1 | 9/2006 | Paterson et al. |
| 2006/0210540 A1 | 9/2006 | Paterson et al. |
| 2006/0233835 A1 | 10/2006 | Paterson et al. |
| 2006/0269561 A1 | 11/2006 | Paterson et al. |
| 2007/0003567 A1 | 1/2007 | Paterson et al. |
| 2007/0253976 A1 | 11/2007 | Paterson et al. |
| 2007/0264279 A1 * | 11/2007 | Gravekamp ....... A61K 39/0011 424/190.1 |
| 2008/0131456 A1 | 6/2008 | Paterson et al. |
| 2009/0081248 A1 | 3/2009 | Paterson et al. |
| 2009/0081250 A1 | 3/2009 | Paterson et al. |
| 2009/0186051 A1 | 7/2009 | Paterson et al. |
| 2009/0202587 A1 | 8/2009 | Paterson et al. |
| 2010/0189739 A1 | 7/2010 | Frankel et al. |
| 2010/0291140 A1 * | 11/2010 | Paterson ............. A61K 39/0011 424/200.1 |
| 2011/0129499 A1 | 6/2011 | Maciag et al. |
| 2011/0142791 A1 | 6/2011 | Shahabi et al. |
| 2011/0305724 A1 | 12/2011 | Paterson et al. |
| 2012/0014984 A1 | 1/2012 | Shahabi et al. |
| 2012/0114685 A1 | 5/2012 | Sewell |
| 2012/0135033 A1 | 5/2012 | Wallecha |
| 2012/0177678 A1 | 7/2012 | Paterson et al. |
| 2013/0259891 A1 | 10/2013 | Harn et al. |
| 2014/0199258 A1 | 7/2014 | Rothman |
| 2014/0234370 A1 | 8/2014 | Shahabi |
| 2014/0248304 A1 | 9/2014 | Paterson et al. |
| 2014/0314708 A1 | 10/2014 | Maciag et al. |
| 2014/0335120 A1 | 11/2014 | Maciag et al. |
| 2015/0079034 A1 | 3/2015 | Seavey et al. |
| 2015/0098964 A1 | 4/2015 | Singh et al. |
| 2015/0125480 A1 | 5/2015 | Paterson et al. |
| 2015/0196628 A1 | 7/2015 | Mason et al. |
| 2015/0238584 A1 | 8/2015 | Shahabi et al. |
| 2015/0297702 A1 | 10/2015 | Shahabi |
| 2015/0335721 A1 | 11/2015 | Paterson et al. |
| 2015/0343047 A1 | 12/2015 | Paterson et al. |
| 2015/0366955 A9 | 12/2015 | Shahabi et al. |
| 2016/0022814 A1 | 1/2016 | Petit et al. |
| 2016/0024173 A1 | 1/2016 | Paterson et al. |
| 2016/0158331 A1 | 6/2016 | Paterson et al. |
| 2016/0206716 A1 | 7/2016 | Seavey et al. |
| 2016/0220652 A1 | 8/2016 | Petit et al. |
| 2016/0228530 A1 | 8/2016 | Paterson |
| 2016/0256538 A1 | 9/2016 | Harn et al. |
| 2016/0324903 A1 | 11/2016 | Rothman et al. |
| 2016/0361401 A1 | 12/2016 | Shahabi et al. |
| 2016/0367650 A1 | 12/2016 | Paterson |
| 2017/0028045 A1 | 2/2017 | Paterson et al. |
| 2017/0049867 A1 | 2/2017 | Seavey et al. |
| 2017/0080064 A1 | 3/2017 | Petit et al. |
| 2017/0100469 A1 | 4/2017 | Paterson et al. |
| 2017/0106072 A1 | 4/2017 | Petit |
| 2017/0204361 A1 | 7/2017 | Eapen et al. |
| 2017/0246273 A1 | 8/2017 | Wallecha et al. |
| 2017/0281691 A1 | 10/2017 | Paterson et al. |
| 2017/0368157 A1 | 12/2017 | Khleif et al. |
| 2018/0064765 A1 | 3/2018 | Petit et al. |
| 2018/0104284 A1 | 4/2018 | Wallecha et al. |
| 2018/0153974 A1 | 6/2018 | Petit et al. |

FOREIGN PATENT DOCUMENTS

| | | |
|---|---|---|
| WO | WO 2001/072329 A1 | 10/2001 |
| WO | WO 2004/062597 A2 | 7/2004 |
| WO | WO 2006/017856 A2 | 2/2006 |
| WO | WO 2006/036550 A2 | 4/2006 |
| WO | WO 2007/106476 A2 | 9/2007 |
| WO | WO 2007/130455 A2 | 11/2007 |
| WO | WO 2008/079172 A2 | 9/2008 |
| WO | WO 2008/109155 A2 | 9/2008 |
| WO | WO 2008/130551 A2 | 10/2008 |

(56) References Cited

FOREIGN PATENT DOCUMENTS

| | | | |
|---|---|---|---|
| WO | WO 2008/140812 A2 | | 11/2008 |
| WO | WO 2009/143167 A2 | | 11/2009 |
| WO | WO 2010/008782 A1 | | 1/2010 |
| WO | WO 2010/040135 A1 | | 4/2010 |
| WO | WO 2010/102140 A1 | | 9/2010 |
| WO | WO 2011/060260 A2 | | 5/2011 |
| WO | WO 2011/100754 A1 | | 8/2011 |
| WO | WO 2012/125551 | * | 9/2012 |
| WO | WO 2012/138377 A2 | | 10/2012 |
| WO | WO 2013/025925 A1 | | 2/2013 |
| WO | WO 2013/138337 A1 | | 9/2013 |
| WO | WO 2015/126921 A1 | | 8/2015 |
| WO | WO 2015/130810 A2 | | 9/2015 |
| WO | WO 2015/134722 A2 | | 9/2015 |
| WO | WO 2015/164121 A1 | | 9/2015 |
| WO | WO 2015/167748 A1 | | 11/2015 |
| WO | WO 2016/011320 A1 | | 1/2016 |
| WO | WO 2016/011353 A1 | | 1/2016 |
| WO | WO 2016/011357 A1 | | 1/2016 |
| WO | WO 2016/011362 A1 | | 1/2016 |
| WO | WO 2016/061182 A1 | | 4/2016 |
| WO | WO 2016/061277 A1 | | 4/2016 |
| WO | WO 2016/100924 A1 | | 6/2016 |
| WO | WO 2016/100929 A1 | | 6/2016 |
| WO | WO 2016/126876 A2 | | 8/2016 |
| WO | WO 2016/126878 A2 | | 8/2016 |
| WO | WO 2016/141121 A1 | | 9/2016 |
| WO | WO 2016/154412 A2 | | 9/2016 |
| WO | WO 2016/183361 A1 | | 11/2016 |
| WO | WO 2016/191545 A1 | | 12/2016 |
| WO | WO 2016/207859 A1 | | 12/2016 |
| WO | WO 2017/048714 A1 | | 3/2017 |
| WO | WO 2017/048850 A1 | | 3/2017 |
| WO | WO 2017/049218 A2 | | 3/2017 |
| WO | WO 2017/066706 A1 | | 4/2017 |
| WO | WO 2017/085691 A1 | | 5/2017 |
| WO | WO 2017/106754 A2 | | 6/2017 |
| WO | WO 2017/132547 A1 | | 8/2017 |
| WO | WO 2018/009461 A1 | | 1/2018 |
| WO | WO 2018/085854 A1 | | 5/2018 |
| WO | WO 2018/102584 A1 | | 6/2018 |
| WO | WO 2018/102585 A1 | | 6/2018 |
| WO | WO 2018/129306 A1 | | 7/2018 |

OTHER PUBLICATIONS

"Advaxis to Report 12-Month Survival from Its Phase 2 Study of ADXS-HPV in Women with Recurrent/Refractory Cervical Cancer", Advaxis, Inc., press release, 3 pages, (2013). [Author Unknown].

Brockstedt et al., "Promises and Challenges for the development of Listeria monocytogenes-based immunotherapies", Expert Review of Vaccines, 7(7):1069-1084, doi: 10.1586/14760584.7.7.1069, (2008).

Gunn et al., "Two Listeria monocytogenes vaccine vectors that express different molecular forms of human papilloma virus-16 (HPV-16) E7 induce qualitatively different T cell immunity that correlates with their ability to induce regression of established tumors immortalized by HPV-16," The Journal of Immunology, The American Association of Immunologists, 167(11):6471-6479, (2001).

Maciag et al., "The first clinical use of a live-attenuated Listeria monocytogenes vaccine: A Phase I safety study of Lm-LLO-E7 in patients with advanced carcinoma of the cervix," Vaccine, 27(30):3975-3983, doi: 10.1016/j.vaccine.2009.04.041, (2009).

Vega et al., "New Listeria monocytogenes prfA* mutants, transcriptional properties of PrfA* proteins and structure-function of the virulence regulator PrfA", Molecular Microbiology, 52(6):1553-1565, doi: 10.1111/j.1365-2958.2004.04052.x, (2004).

Verch et al., "Listeria monocytogenes-based antibiotic resistance gene-free antigen delivery system applicable to other bacterial vectors and DNA vaccines", Infection and Immunity, American Society for Microbiology, 72(11):6418-6425, doi: 10.1128/IAI.72.11.6418-6425.2004, (2004).

Wallecha et al. "Lm-LLO-Based Immunotherapies and HPV-Associated Disease," Journal of Oncology, 2012:1-10, Article ID 542851, doi: 10.1155/2012/54285, (2012). [Received Aug. 5, 2011; Accepted Oct. 9, 2011].

EPO Application No. 15782800.5 (Published as EP3134510A1),Supplementary European Search Report and European Search Opinion dated Mar. 23, 2018.

WIPO Application No. PCT/US2015/025690, PCT International Preliminary Report on Patentability dated Oct. 25, 2016.

WIPO Application No. PCT/US2015/025690, PCT International Search Report dated Jul. 24, 2015.

WIPO Application No. PCT/US2015/025690, PCT Written Opinion of the International Searching Authority dated Jul. 24, 2015.

* cited by examiner

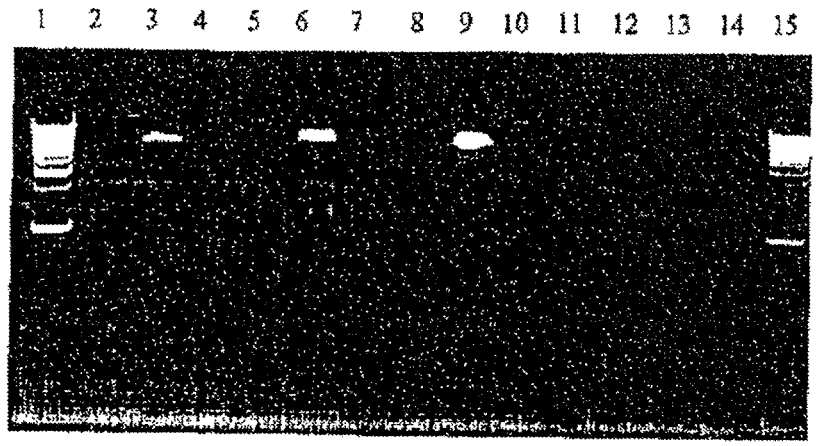

| Lane | Sample | Lane | Sample |
|---|---|---|---|
| 1 | 1Kb ladder | 9 | LB B, generation 5 |
| 2 | 100ng reference pGG55 | 10 | LB A, generation 9 |
| 3 | LB A, generation 5 | 11 | LB B, generation 14 |
| 4 | LB A, generation 9 | 12 | LB B, generation 19* |
| 5 | LB A, generation 14 | 13 | LB B, generation 24* |
| 6 | LB A, generation 19 | 14 | LB B, generation 29* |
| 7 | LB A, generation 24 | 15 | 1Kb ladder |
| 8 | LB A, generation 29 | | |

* Residual ethanol remaining in sample, therefore the majority of the sample did not load into the well, resulting in a less intense plasmid band

Figure 9A

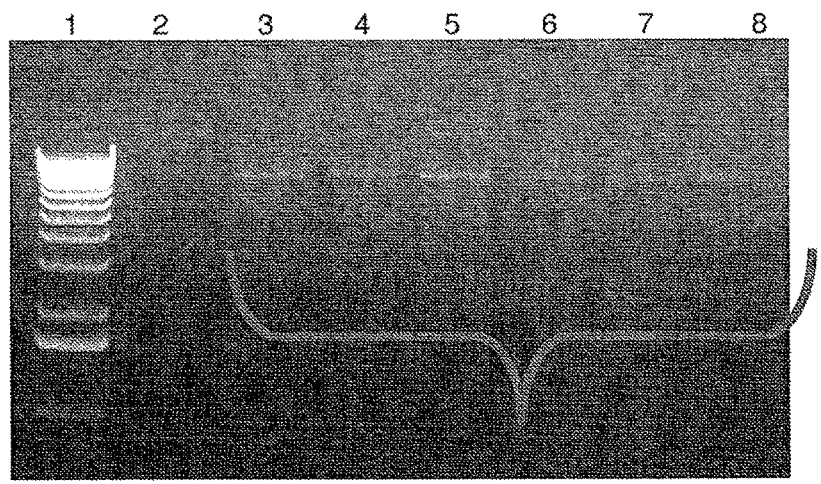

Lane Sample

| Lane | Sample | Lane | Sample |
|---|---|---|---|
| 1 | 1Kb ladder | 5 | TB, generation 21 |
| 2 | 100ng reference pGG55 | 6 | TB, generation 28 |
| 3 | TB, generation 7 | 7 | TB, generation 35 |
| 4 | TB, generation 14 | 8 | TB, generation 42 |

Figure 9B

```
                                ADW451 →
Lovaxin_C_pGG55      CCAAACCTACAAAAACAAGTTTCATACAGCCTAGCTAAATTTAATGTTT
Reference_10403S_pHA CCAAACCTACAAAAACAAGTTTCATACAGCCTAGCTAAATTTAATGATT
                                                    ADW452 →
                     ************************************    **

Lovaxin_C_pGG55      TTTCGATTAACGGGAAGCTTGGCTCTATTTGCGGTCAACTTTTAATCCTG
Reference_10403S_pHA TTTCGATTAACGGGAAGCTTGGCTCTATTTGCGGTCAACTTTTAATCCTG
                     *************************************************

Lovaxin_C_pGG55      ACCTATGTGTATGGTAAAGAAACTCCTGATGGCATCAAGATTACACTGGA
Reference_10403S_pHA ACCTATGTGTATGGTAAAGAAACTCCTGATGGCATCAAGATTACACTGGA
                     *************************************************

Lovaxin_C_pGG55      TAATTTAACAATGCAGGAGTTAGGAGATATTCAAGTGGCATCCACATAGCT
Reference_10403S_pHA TAATTTAACAATGCAGGAGTTAGGAGATATTCAAGTGGCATCCACATAGCT
                     *************************************************

Lovaxin_C_pGG55      CAGCTGTTAGAGAATTATTTCCAAATTAAAGCAAGAGAAAAGTTATCGTG
Reference_10403S_pHA CAGCTGTTAGAGAATTATTTCCAAATTAAAGCAAGAGAAAAGTTATCGTG
                     *************************************************

Lovaxin_C_pGG55      TATAAAAATTCATGCTTTTTATGTACAAAATCGTGATTATCTCAAAAGATA
Reference_10403S_pHA TATAAAAATTCATGCTTTTTATGTACAAAATCGTGATTATCTCAAAAGATA
                     *************************************************

Lovaxin_C_pGG55      TGCCCCTAAATTAGATGATGTTTTATTAGCATGTCCTGCTACTGGG
Reference_10403S_pHA TGCCCCTAAATTAGATGATGTTTTATTAGCATGTCCTGCTACTGGG
                                                              ←ADW453
                     **********************************************

Lovaxin_C_pGG55      GAAAATTAAATTAA  (SEQ ID NO: 35)
Reference_10403S_pHA GAAAATTAAATTAA  (SEQ ID NO: 36)
                     **************
```

Figure 13

1. 5 ng of pGG55 D133V;
2. 1 ng of pGG55 D133V;
3. 0.2 ng of pGG55 D133V;
4. 5 ng of pGG55 wild-type;
5. 1 ng of pGG55 wild-type;
6. 0.2 ng of pGG55 wild-type;

1) 5 ng of pGG55 D133V;
2) 1 ng of pGG55 D133V;
3) 0.2 ng of pGG55 D133V;
4) 5 ng of pGG55 wild-type;
5) 1 ng of pGG55 wild-type;
6) 0.2 ng of pGG55 wild-type;

1. 1 ng of pGG55 D133V
2. 1 ng of pGG55 wild-type
3. 100 pg of pGG55 wild-type ($10^{-1}$)
4. 10 pg of pGG55 wild-type ($10^{-2}$)
5. 1 pg of pGG55 wild-type ($10^{-3}$)
6. 100 fg of pGG55 wild-type ($10^{-4}$)
7. 10 fg of pGG55 wild-type ($10^{-5}$)
8. 1 fg of pGG55 wild-type ($10^{-6}$)

1. 5 ng of pGG55 D133V
2. 5 ng of pGG55 wild-type
3. 500 pg of pGG55 wild-type ($10^{-1}$)
4. 50 pg of pGG55 wild-type ($10^{-2}$)
5. 5 pg of pGG55 wild-type ($10^{-3}$)
6. 500 fg of pGG55 wild-type ($10^{-4}$)
7. 50 fg of pGG55 wild-type ($10^{-5}$)
8. 5 fg of pGG55 wild-type ($10^{-6}$)

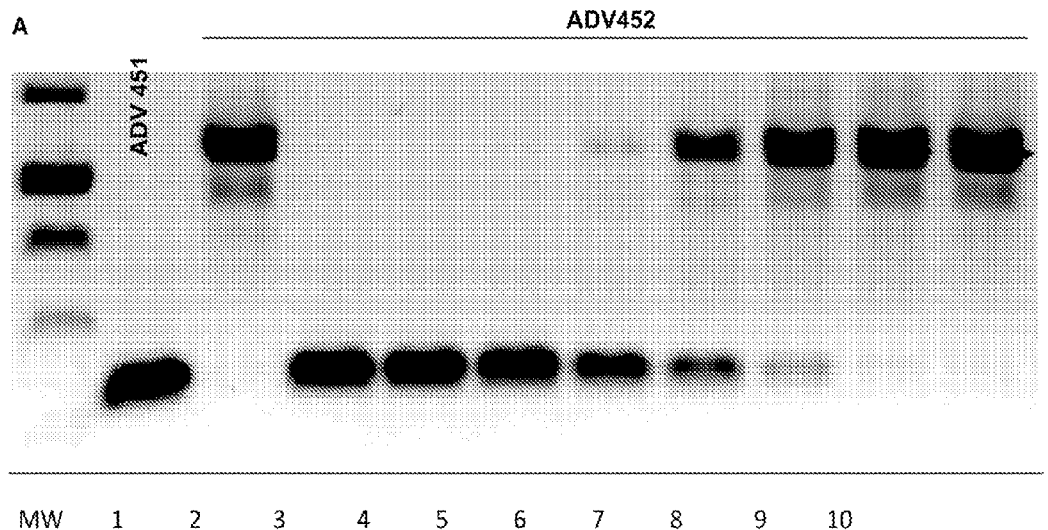
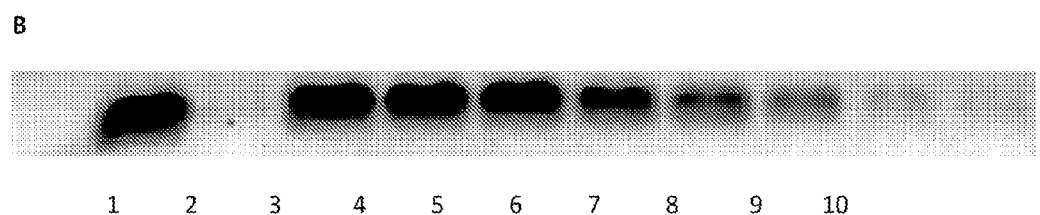
1) 1 ng of pGG55 D133V only
2) 1 ng of pGG55 D133V only
3) 1 ng of pGG55 D133V + 1 ng of pGG55 wild-type prfA
4) 1 ng of pGG55 D133V + 100 pg of pGG55 wild-type prfA
6) 1 ng of pGG55 D133V + 1 pg of pGG55 wild-type prfA
7) 1 ng of pGG55 D133V + 100 fg of pGG55 wild-type prfA
8) 1 ng of pGG55 D133V + 10 fg of pGG55 wild-type prfA
9) 1 ng of pGG55 D133V + 1 fg of pGG55 wild-type prfA
Figure 22

RECOMBINANT *LISTERIA* VACCINE STRAINS AND METHODS OF PRODUCING THE SAME

CROSS REFERENCE TO RELATED APPLICATIONS

This application is a US national stage of PCT/US2015/025690 filed Apr. 14, 2015, which claims priority from and the benefit of U.S. 61/983,732 filed Apr. 24, 2014 all of which are incorporated herein by reference.

REFERENCE TO SEQUENCE LISTING

This application includes an electronic sequence listing in a file named 486546_SEQLST.txt, created on Oct. 24, 2016 and containing 34,240 bytes, which is hereby incorporated by reference in its entirety for all purposes.

FIELD OF INVENTION

The present invention provides methods of treating, protecting against, and inducing an immune response against a tumor or cancer, comprising the step of administering to a subject a recombinant *Listeria* strain comprising a nucleic acid encoding a mutant PrfA protein that partially restores PrfA function.

BACKGROUND OF THE INVENTION

Persistent infection with high-oncogenic risk human papillomavirus (HR-HPV) types is recognized as a necessary, but not sufficient, cause of invasive carcinoma of the cervix (ICC) [1-3]. HPVs 16 and 18 are the most prevalent types in malignant lesions, accounting for over 70% of ICC and over 50% of high-grade precursor lesions. The HR-HPV E6 and E7 proteins are consistently expressed in dysplasias and carcinomas, disrupting the cell cycle regulatory proteins p53 and pRb, respectively. The obligatory expression of E6 and E7 by both dysplastic and invasive malignant lesions, as well as the viral origin of these proteins, make them excellent targets for HPV therapeutic vaccines.

*Listeria monocytogenes* (Lm) is a food-borne gram-positive bacterium that can occasionally cause disease in humans, in particular elderly individuals, newborns, pregnant women and immunocompromised individuals. In addition to strongly activating innate immunity and inducing a cytokine response that enhances antigen-presenting cell (APC) function, Lm has the ability to replicate in the cytosol of APCs after escaping from the phagolysosome, mainly through the action of the listeriolysin O (LLO) protein. This unique intracellular life cycle allows antigens secreted by Lm to be processed and presented in the context of both MHC class I and II molecules, resulting in potent cytotoxic $CD8^+$ and Th1 $CD4^+$ T-cell-mediated immune responses. Lm has been extensively investigated as a vector for cancer immunotherapy in pre-clinical models Immunization of mice with Lm-LLO-E7 induces regression of established tumors expressing E7 and confers long-term protection. The therapeutic efficacy of Lm-LLO-E7 correlates with its ability to induce E7-specific CTLs that infiltrate the tumor site, mature dendritic cells, reduce the number of intratumoral regulatory $CD4^+$ $CD25^+$ T cells and inhibit tumor angiogenesis.

Lm has also a number of inherent advantages as a vaccine vector. The bacterium grows very efficiently in vitro without special requirements and it lacks LPS, which is a major toxicity factor in gram-negative bacteria, such as *Salmonella*. Genetically attenuated Lm vectors also offer additional safety as they can be readily eliminated with antibiotics, in case of serious adverse effects and unlike some viral vectors, no integration of genetic material into the host genome occurs. However, there is always great concern about the safety of a live bacterial vaccine such as Lm, especially regarding its mechanism of attenuation.

The PrfA protein controls the expression of a regulon comprising essential virulence genes required by Lm to colonize its vertebrate hosts; hence the prfA mutation strongly impairs PrfA ability to activate expression of PrfA-dependent virulence genes. The present invention addresses this concern by providing a prfA mutant *Listeria* that carries a mutant prfA (D133V) gene in the pGG55 plasmid that restores partial PrfA function.

SUMMARY OF THE INVENTION

In one embodiment, the present invention relates to a recombinant *Listeria* strain, said recombinant *Listeria* strain comprising a recombinant nucleic acid, said nucleic acid comprising a first open reading frame encoding a recombinant polypeptide comprising a first an N-terminal fragment of an LLO protein fused to a heterologous antigen or fragment thereof, and wherein said recombinant nucleic acid further comprises a second open reading frame encoding a mutant PrfA protein.

In one embodiment, the present invention relates to a recombinant *Listeria* strain, said recombinant *Listeria* strain comprising a recombinant nucleic acid, said nucleic acid comprising a first open reading frame encoding a recombinant polypeptide comprising a first an N-terminal fragment of an LLO protein fused to a heterologous antigen or fragment thereof, wherein said recombinant nucleic acid further comprises a second open reading frame encoding a mutant PrfA protein, and wherein said *Listeria* comprises a genomic mutation or deletion in the prfA gene. In another embodiment, the mutant PrfA protein encoded by said second open reading frame complements said genomic mutation or deletion in said *Listeria* strain's PrfA protein. In another embodiment, the mutant PrfA protein encoded by said second open reading frame restores partial PrfA function in said *Listeria* strain.

In one embodiment, the present invention relates to a method for inducing an immune response against a tumor or a cancer in a subject, the method comprising the step of administering to said subject a recombinant *Listeria* strain comprising a recombinant nucleic acid, said nucleic acid comprising a first open reading frame encoding a recombinant polypeptide comprising an N-terminal fragment of an LLO protein fused to a heterologous antigen or fragment thereof, is, wherein said recombinant nucleic acid further comprises a second open reading frame encoding a mutant PrfA protein, thereby inducing an immune response against a tumor or a cancer. In another embodiment, the recombinant *Listeria* strain comprises a genomic mutation or deletion in the prfA gene.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 9A shows plasmid isolation throughout LB stability study. FIG. 9B shows plasmid isolation throughout TB stability study.

FIG. 13. Representation of the location of the ADV451, 452 and 453 primers and the segment of the prfA gene amplified in the reaction.

FIG. 22. Analysis of the D133V prfA mutation in the Lm-LLO-E7. A, Original image used for densitometry; B, Image was digitally enhanced to facilitate the visualization of the low density bands.

Figure 1:
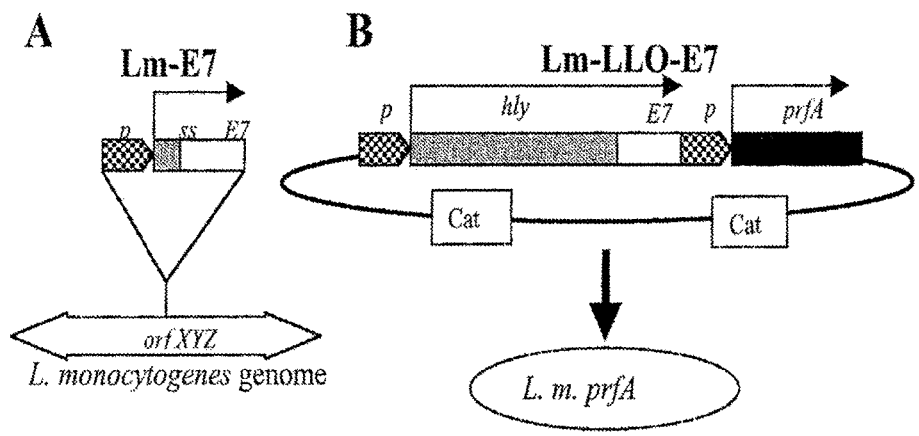
FIG. 1. Lm-E7 and Lm-LLO-E7 use different expression systems to express and secrete E7. Lm-E7 was generated by introducing a gene cassette into the orfZ domain of the *L. monocytogenes* genome (A). The hly promoter drives expression of the hly signal sequence and the first five amino acids (AA) of LLO followed by HPV-16 E7. B), Lm-LLO-E7 was generated by transforming the prfA-strain XFL-7 with the plasmid pGG-55. pGG-55 has the hly promoter driving expression of a nonhemolytic fusion of LLO-E7. pGG-55 also contains the prfA gene to select for retention of the plasmid by XFL-7 in vivo.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

The present invention provides, in one embodiment, a recombinant *Listeria* strain, said recombinant *Listeria* strain comprising a recombinant nucleic acid, said nucleic acid comprising a first open reading frame encoding a recombinant polypeptide comprising a first an N-terminal fragment of an LLO protein fused to a heterologous antigen or fragment thereof, wherein said recombinant nucleic acid further comprises a second open reading frame encoding a mutant PrfA protein, and wherein said *Listeria* comprises a genomic mutation or deletion in the prfA gene. In another embodiment, the mutant PrfA protein encoded by said second open reading frame complements said genomic mutation or deletion in said *Listeria* strain's prfA gene. In another embodiment, the mutant PrfA protein encoded by said second open reading frame restores partial PrfA function in said *Listeria* strain. In one embodiment, the mutant PrfA protein encoded by said second open reading frame comprises a point mutation in position 133. In another embodiment, the mutation on residue 133 of the PrfA amino acid sequence is from amino acid D or Asp or Aspartate (or Aspartic acid) to amino acid V or Val or Valine.

The present invention further provides immunogenic compositions comprising a recombinant *Listeria* strain provided herein and methods of using the same, including methods of treating, protecting against, and inducing an immune response against a disease, where in some embodiments, the disease is a tumor or cancer.

The present invention also provides methods for inducing an anti-disease cytotoxic T-cell (CTL) response in a subject and treating disorders, and symptoms associated with said disease comprising administering a recombinant *Listeria* strain provided herein, wherein in some embodiments the disease is a tumor or a cancer.

In another embodiment, a recombinant *Listeria* provided herein is an attenuated *Listeria*. "Attenuation" and "attenuated" may encompass a bacterium, virus, parasite, infectious organism, prion, tumor cell, gene in the infectious organism, and the like, that is modified to reduce toxicity to a host. The host can be a human or animal host, or an organ, tissue, or cell. The bacterium, to give a non-limiting example, can be attenuated to reduce binding to a host cell, to reduce spread from one host cell to another host cell, to reduce extracellular growth, or to reduce intracellular growth in a host cell. Attenuation can be assessed by measuring, e.g., an indicum or indicia of toxicity, the LD50, the rate of clearance from an organ, or the competitive index (see, e.g., Auerbuch, et al. (2001) Infect Immunity 69:5953-5957). Generally, an attenuation results an increase in the $LD_{50}$ and/or an increase in the rate of clearance by at least 25%; more generally by at least 50%; most generally by at least 100% (2-fold); normally by at least 5-fold; more normally by at least 10-fold; most normally by at least 50-fold; often by at least 100-fold; more often by at least 500-fold; and most often by at least 1000-fold; usually by at least 5000-fold; more usually by at least 10,000-fold; and most usually by at least 50,000-fold; and most often by at least 100,000-fold.

It will be well appreciated by a skilled artisan that the term "Attenuated gene" may encompass a gene that mediates toxicity, pathology, or virulence, to a host, growth within the host, or survival within the host, where the gene is mutated in a way that mitigates, reduces, or eliminates the toxicity, pathology, or virulence. The reduction or elimination can be assessed by comparing the virulence or toxicity mediated by the mutated gene with that mediated by the non-mutated (or parent) gene. "Mutated gene" encompasses deletions, point mutations, and frameshift mutations in regulatory regions of the gene, coding regions of the gene, non-coding regions of the gene, or any combination thereof.

In one embodiment, provided herein is a method for inducing an immune response against a tumor or a cancer in a subject, the method comprising the step of administering to said subject a composition comprising a recombinant *Listeria* strain provided herein, thereby inducing an immune response against a tumor or a cancer.

In one embodiment, the present invention provides a method of treating a tumor or cancer in a subject, comprising the step of administering to the subject a composition comprising a recombinant *Listeria* strain provided herein. In another embodiment, the present invention provides a method of protecting a subject against a tumor or cancer, comprising the step of administering to the subject the recombinant *Listeria* strain provided herein. In another embodiment, the recombinant *Listeria* strain expresses the recombinant polypeptide. In another embodiment, the recombinant *Listeria* strain comprises a plasmid that encodes the recombinant polypeptide. In another embodiment, the recombinant *Listeria* strain comprises a genomic mutation or deletion in the prfA gene.

In one embodiment, the methods provided herein further comprise the step of boosting a subject with a composition comprising a recombinant *Listeria* strain of the present invention. In another embodiment, the method further comprises the step of boosting the subject with an immunogenic composition comprising a heterologous antigen or fragment thereof provided herein. In another embodiment, the method further comprises the step of boosting the subject with an immunogenic composition that directs a cell of the subject to express the heterologous antigen. In another embodiment, the cell is a tumor cell. In another embodiment, the cell is an antigen-presenting cell. In another embodiment, the method further comprises the step of boosting the subject with a vaccine comprising a recombinant *Listeria* strain of the present invention.

In one embodiment, the fragment thereof in the context of LLO proteins and ActA proteins provided herein refer to a peptide or polypeptide comprising an amino acid sequence of at least 5 contiguous amino acid residues of the LLO or ActA proteins. In another embodiment, the term refers to a peptide or polypeptide comprising an amino acid sequence of at least of at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, at least 250 contiguous amino acid residues of the amino acid sequence, at least 300 contiguous amino acid residues, at least 350 contiguous amino acid residues of, at least 400 contiguous amino acid residues, or at least 450 contiguous amino acid residues of an LLO or ActA protein or polypeptide.

In another embodiment, a "fragment" is a functional fragment that comprises a biological activity (e.g. to elicit an immune response against a heterologous antigen expressed by a tumor cell, either when administered alone or when administered in the context of a fusion protein as further described herein. In another embodiment, the fragment is functional in a non-fused form.

The present invention, in certain embodiments, provides codon optimization of a nucleic acid heterologous to *Listeria*, or of a nucleic acid endogenous to *Listeria*. The optimal codons utilized by *L. monocytogenes* for each amino acid are shown US Patent Publication 2007/0207170, which is hereby incorporated by reference herein. A nucleic acid is codon-optimized if at least one codon in the nucleic acid is replaced with a codon that is more frequently used by *L. monocytogenes* for that amino acid than the codon in the original sequence.

An N-terminal LLO protein fragment and heterologous antigen provided herein are, in one embodiment, fused directly to one another. In another embodiment, the genes encoding the N-terminal LLO protein fragment and the heterologous antigen are fused directly to one another. In another embodiment, the N-terminal LLO protein fragment and the heterologous antigen are attached via a linker peptide. In another embodiment, the N-terminal LLO protein fragment and the heterologous antigen are attached via a heterologous peptide. In another embodiment, the N-terminal LLO protein fragment is N-terminal to the heterologous antigen. In another embodiment, the N-terminal LLO protein fragment is the N-terminal-most portion of the fusion protein. Each possibility represents a separate embodiment of the present invention.

As provided herein, recombinant *Listeria* strains expressing LLO-antigen fusions induce anti-tumor immunity (Example 1), elicit antigen-specific T cell proliferation (Example 2), generate antigen-specific, and tumor-infiltrating T cells (Example 3).

In another embodiment, the present invention provides a method of treating a tumor or cancer in a subject, comprising the step of administering to the subject a recombinant *Listeria* strain, the recombinant *Listeria* strain comprising a recombinant polypeptide comprising an N-terminal fragment of an LLO protein and an HPV E7 antigen, whereby the recombinant *Listeria* strain induces an immune response against the E7 antigen, thereby treating a tumor or cancer in a subject. In another embodiment, the recombinant *Listeria* strain expresses the recombinant polypeptide. In another embodiment, the recombinant *Listeria* strain comprises a plasmid that encodes the recombinant polypeptide. Each possibility represents a separate embodiment of the present invention.

In one embodiment, the terms "recombinant polypeptide" and "fusion protein" are used interchangeably herein.

In another embodiment, the present invention provides a method of protecting a subject against a tumor or cancer, comprising the step of administering to the subject a recombinant *Listeria* strain, the recombinant *Listeria* strain comprising a recombinant polypeptide comprising an N-terminal fragment of an LLO protein and an HPV E7 antigen, whereby the recombinant *Listeria* strain induces an immune response against the E7 antigen, thereby protecting a subject against a tumor or cancer. In another embodiment, the recombinant *Listeria* strain expresses the recombinant polypeptide. In another embodiment, the recombinant *Listeria* strain comprises a plasmid that encodes the recombinant polypeptide. Each possibility represents a separate embodiment of the present invention.

In another embodiment, the present invention provides a method for inducing an immune response against a tumor or cancer in a subject, comprising the step of administering to the subject a recombinant *Listeria* strain, the recombinant *Listeria* strain comprising a recombinant polypeptide comprising an N-terminal fragment of an LLO protein and an HPV E7 antigen, thereby inducing an immune response against a tumor or cancer in a subject. In another embodiment, the recombinant *Listeria* strain expresses the recombinant polypeptide. In another embodiment, the recombinant *Listeria* strain comprises a plasmid that encodes the recombinant polypeptide. Each possibility represents a separate embodiment of the present invention.

In another embodiment, the present invention provides a method of treating a tumor or cancer in a subject, comprising the step of administering to the subject a recombinant *Listeria* strain, the recombinant *Listeria* strain comprising a recombinant polypeptide comprising an N-terminal fragment of an ActA protein and heterologous antigen, whereby the recombinant *Listeria* strain induces an immune response against the heterologous antigen, thereby treating a tumor or cancer in a subject. In another embodiment, the recombinant *Listeria* strain expresses the recombinant polypeptide. In another embodiment, the recombinant *Listeria* strain comprises a plasmid that encodes the recombinant polypeptide. Each possibility represents a separate embodiment of the present invention.

In another embodiment, the present invention provides a method of protecting a subject against a tumor or cancer, comprising the step of administering to the subject a recombinant *Listeria* strain, the recombinant *Listeria* strain comprising a recombinant polypeptide comprising an N-terminal fragment of an ActA protein and a heterologous antigen, whereby the recombinant *Listeria* strain induces an immune response against the heterologous antigen, thereby protecting a subject against a tumor or cancer. In another embodiment, the recombinant *Listeria* strain expresses the recombinant polypeptide. In another embodiment, the recombinant *Listeria* strain comprises a plasmid that encodes the recombinant polypeptide. Each possibility represents a separate embodiment of the present invention.

In another embodiment, the present invention provides a method for inducing an immune response against a tumor or cancer in a subject, comprising the step of administering to the subject a recombinant *Listeria* strain, the recombinant *Listeria* strain comprising a recombinant polypeptide comprising an N-terminal fragment of an heterologous protein and a heterologous antigen, thereby inducing an immune response against a tumor or cancer in a subject. In another embodiment, the recombinant *Listeria* strain expresses the recombinant polypeptide. In another embodiment, the recombinant *Listeria* strain comprises a plasmid that encodes the recombinant polypeptide. Each possibility represents a separate embodiment of the present invention.

The N-terminal ActA protein fragment and the heterologous antigen are, in another embodiment, fused directly to one another. In another embodiment, the genes encoding the N-terminal ActA protein fragment and heterologous antigen are fused directly to one another. In another embodiment, the N-terminal ActA protein fragment and heterologous antigen are attached via a linker peptide. In another embodiment, the N-terminal ActA protein fragment and heterologous antigen are attached via a heterologous peptide. In another embodiment, the N-terminal ActA protein fragment is N-terminal to the heterologous antigen. In another embodiment, the N-terminal ActA protein fragment is the N-terminal-most portion of the fusion protein. Each possibility represents a separate embodiment of the present invention.

In another embodiment, the present invention provides a method of inducing an immune response against a tumor or cancer in a subject, comprising the step of administering to the subject a recombinant *Listeria* strain, the recombinant *Listeria* strain comprising a recombinant polypeptide comprising a PEST amino acid sequence-containing peptide and a heterologous antigen, whereby the recombinant *Listeria* strain induces an immune response against the heterologous antigen, thereby treating a tumor or cancer in a subject. In another embodiment, the recombinant *Listeria* strain expresses the recombinant polypeptide. In another embodiment, the recombinant *Listeria* strain comprises a plasmid that encodes the recombinant polypeptide. In another embodiment, the method protects a subject against a tumor or cancer. In another embodiment, the method treats a tumor or cancer in said subject.

The PEST amino acid sequence-containing peptide and heterologous antigen are, in another embodiment, fused directly to one another. In another embodiment, the genes encoding the PEST amino acid sequence-containing peptide and heterologous antigen are fused directly to one another. In another embodiment, the PEST amino acid sequence-containing peptide and heterologous antigen are attached via a linker peptide. In another embodiment, the PEST amino acid sequence-containing peptide and heterologous antigen are attached via a heterologous peptide. In another embodiment, the PEST amino acid sequence-containing peptide is N-terminal to the heterologous antigen. In another embodiment, the PEST amino acid sequence-containing peptide is the N-terminal-most portion of the fusion protein. Each possibility represents a separate embodiment of the present invention.

In another embodiment, the present invention provides a method for vaccinating a subject against an HPV, comprising the step of administering to the subject a prfA mutant recombinant *Listeria* strain provided herein, wherein the *Listeria* expresses an HPV antigen and wherein the *Listeria* comprises a plasmid that expresses a mutant PrfA protein. In another embodiment, the recombinant *Listeria* strain expresses a recombinant polypeptide comprising said HPV antigen. In another embodiment, the recombinant *Listeria* strain comprises a plasmid that encodes the recombinant polypeptide. Each possibility represents a separate embodiment of the invention.

In one embodiment, provided herein is a method of increasing a ratio of T effector cells to regulatory T cells (Tregs) in the spleen and tumor microenvironments of a subject, comprising administering the immunogenic composition provided herein. In another embodiment, increasing a ratio of T effector cells to regulatory T cells (Tregs) in the spleen and tumor microenvironments in a subject allows for a more profound anti-tumor response in the subject.

In one embodiment, a mutant PrfA protein provided herein comprises a D133V amino acid mutation. In another embodiment, the mutant PrfA protein consists of a D133V amino acid mutation. In another embodiment, a nucleic acid comprising an open reading frame encoding a mutant PrfA protein provided herein is in a plasmid in said recombinant *Listeria*. In another embodiment, the plasmid comprising a nucleic acid encoding a mutant PrfA protein provided herein is an integrative plasmid. In another embodiment, the plasmid comprising a nucleic acid encoding a mutant PrfA protein provided herein is an episomal or extrachromosomal plasmid.

In one embodiment, a prfA mutant recombinant *Listeria* provided herein comprises a partial deletion in or a complete deletion of the chromosomal prfA gene. In another embodiment, the prfA mutant *Listeria* comprises a loss-of-function mutation in the prfA gene.

In one embodiment, a mutant PrfA protein provided herein complements a genomic deletion, inactivation or mutation in the prfA gene in a recombinant *Listeria*. In another embodiment, a mutant PrfA protein provided herein complements a genomic deletion, inactivation or mutation in the prfA gene in the recombinant *Listeria* provided herein. In another embodiment, a mutant PrfA protein provided herein restores partial prfA function in a recombinant *Listeria* comprising a genomic deletion, inactivation or mutation of the prfA gene. In another embodiment, a mutant PrfA protein provided herein restores a loss-of PrfA function mutation in a recombinant *Listeria*.

In one embodiment, a wild-type PrfA protein is encoded by the following wild-type nucleic acid sequence set forth in SEQ ID NO: 31.

```
                                                        (SEQ ID NO: 31)
  1 atgaacgctc aagcagaaga attcaaaaaa tatttagaaa ctaacgggat aaaaccaaaa 61 caatttcata aaaaagaact tattttttaac caatgggatc cacaagaata ttgtatttttt 121 ctatatgatg gtatcacaaa gctcacgagt attagcgaga acgggaccat catgaattta 181 caatactaca aaggggcttt cgttataatg tctggcttta ttgatacaga aacatcggtt 241 ggctattata atttagaagt cattagcgag caggctaccg catacgttat caaaataaac 301 gaactaaaag aactactgag caaaaatctt acgcactttt tctatgtttt ccaaacccta 361 caaaaacaag tttcatacag cctagctaaa tttaatgatt tttcgattaa cgggaagctt 421 ggctctattt gcggtcaact tttaatcctg acctatgtgt atggtaaaga aactcctgat 481 ggcatcaaga ttacactgga taatttaaca atgcaggagt taggatattc aagtggcatc 541 gcacatagct cagctgttag cagaattatt tccaaattaa agcaagagaa agttatcgtg 601 tataaaaatt catgctttta tgtacaaaat cttgattatc tcaaaagata tgcccctaaa 661 ttagatgaat ggttttattt agcatgtcct gctacttggg gaaaattaaa ttaa
```

In one embodiment, a wild-type PrfA protein comprises an amino acid sequence set forth in SEQ ID NO: 32.

```
                                        (SEQ ID NO: 32)
M N A Q A E E F K K Y L E T N G I K P K Q F H K K E

L I F N Q W D P Q E Y C I F L Y D G I T K L T S I S

E N G T I M N L Q Y Y K G A F V I M S G F I D T E T

S V G Y Y N L E V I S E Q A T A Y V I K I N E L K E

L L S K N L T H F F Y V F Q T L Q K Q V S Y S L A K

F N D F S I N G K L G S I C G Q L L I L T Y V V G K

E T P D G I K I T L D N L T M Q E L G Y S S G I A H
```

-continued

S S A V S R I I S K L K Q E K V I V Y K N S C F Y V

Q N L D Y L K R Y A P K L D E W F Y L A C P A T W G

K L N.

In one embodiment, a nucleic acid sequence encoding a mutant prfA sequence is set forth in SEQ ID NO: 33.

(SEQ ID NO: 33)

```
  1 atgaacgctc aagcagaaga attcaaaaaa tatttagaaa ctaacgggat aaaaccaaaa 61 caatttcata aaaaagaact tatttttaac caatgggatc cacaagaata ttgtattttt 121 ctatatgatg gtatcacaaa gctcacgagt attagcgaga acgggaccat catgaattta 181 caatactaca aagggcttt cgttataatg tctggcttta ttgatacaga aacatcggtt 241 ggctattata atttagaagt cattagcgag caggctaccg catacgttat caaaataaac 301 gaactaaaag aactactgag caaaaatctt acgcactttt tctatgtttt ccaaacccta 361 caaaaacaag tttcatacag cctagctaaa tttaatgttt tttcgattaa cgggaagctt 421 ggctctattt gcggtcaact tttaatcctg acctatgtgt atggtaaaga aactcctgat 481 ggcatcaaga ttacactgga taatttaaca atgcaggagt taggatattc aagtggcatc 541 gcacatagct cagctgttag cagaattatt tccaaattaa agcaagagaa agttatcgtg 601 tataaaaatt catgcttta tgtacaaaat cgtgattatc tcaaaagata tgcccctaaa 661 ttagatgaat ggttttattt agcatgtcct gctacttggg gaaaattaaa ttaa
```

In one embodiment, a mutant PrfA protein provided herein comprises an amino acid sequence set forth in SEQ ID NO: 34.

M N A Q A E E F K K Y L E T N G I K P K Q F H K K E L I F N Q W D P Q E Y C I F L Y D G I T K L T S I S E N G T I M N L Q Y Y K G A F V I M S G F I D T E T S V G Y Y N L E V I S E Q A T A Y V I K I N E L K E L L S K N L T H F F Y V F Q T L Q K Q V S Y S L A K F N V F S I N G K L G S I C G Q L L I L T Y V Y G K E T P D G I K I T L D N L T M Q E L G Y S S G I A H S S A V S R I I S K L K Q E K V I V Y K N S C F Y V Q N R D Y L K R Y A P K L D E W F Y L A C P A T W G K L N (SEQ ID NO: 34). In another embodiment, SEQ ID NO: 34 represents a mutant PrfA protein comprising a D133V mutation. In another embodiment, a mutant PrfA protein is homologous to SEQ ID NO: 34 and comprises a D133V mutation. In another embodiment, a mutant PrfA protein is at least 90% homologous with SEQ ID NO: 34 and comprises a D133V mutation. In another embodiment, a mutant PrfA protein is at least 85% homologous with SEQ ID NO: 34, and comprises a D133V mutation.

In another embodiment, the subject is at risk for developing an HPV-mediated carcinogenesis (e.g. a cervical, head and neck or anal cancer). In another embodiment, the subject is HPV-positive.

In another embodiment, the subject exhibits cervical intraepithelial neoplasia. In another embodiment, the subject exhibits a squamous intraepithelial lesion. In another embodiment, the subject exhibits a dysplasia in the cervix.

The HPV that is the target of methods of the present invention is, in another embodiment, an HPV 16. In another embodiment, the HPV is an HPV-18. In another embodiment, the HPV is selected from HPV-16 and HPV-18. In another embodiment, the HPV is an HPV-31. In another embodiment, the HPV is an HPV-35. In another embodiment, the HPV is an HPV-39. In another embodiment, the HPV is an HPV-45. In another embodiment, the HPV is an HPV-51. In another embodiment, the HPV is an HPV-52. In another embodiment, the HPV is an HPV-58. In another embodiment, the HPV is a high-risk HPV type. In another embodiment, the HPV is a mucosal HPV type. Each possibility represents a separate embodiment of the present invention.

In another embodiment, the present invention provides a method of vaccinating a subject against an antigen of interest, the method comprising the step of intravenously administering to the subject an immunogenic composition, comprising a fusion of an immunogenic peptide to the antigen of interest, wherein the immunogenic peptide is selected from (a) an N-terminal fragment of an LLO protein; (b) an ActA protein or N-terminal fragment thereof; and (c) a PEST amino acid sequence-containing peptide, thereby vaccinating a subject against an antigen of interest.

In another embodiment, the present invention provides a method of vaccinating a subject against an antigen of interest, the method comprising the step of administering intravenously to the subject a recombinant *Listeria* strain comprising a recombinant polypeptide, the recombinant polypeptide comprising an immunogenic peptide fused to the antigen of interest, wherein the immunogenic peptide is selected from (a) an N-terminal fragment of an LLO protein; (b) an ActA protein or N-terminal fragment thereof; and (c) a PEST amino acid sequence-containing peptide, thereby vaccinating a subject against an antigen of interest.

In another embodiment, the present invention provides a method of inducing a CTL response in a subject against an antigen of interest, the method comprising the step of administering to the subject a recombinant *Listeria* strain comprising or expressing the antigen of interest, thereby inducing a CTL response in a subject against an antigen of interest. In another embodiment, the step of administering is intravenous or oral administration. Each possibility represents a separate embodiment of the present invention.

As provided herein, recombinant *Listeria* strains expressing LLO-antigen fusions induce anti-tumor immunity (Example 1), elicit antigen-specific T cell proliferation (Example 2), generate antigen-specific, and tumor-infiltrating T cells (Example 3). Thus, vaccines of the present invention are efficacious at inducing immune responses against HPV antigens E7 and E6.

In another embodiment, the present invention provides a method for inducing a regression of a cancer in a subject, comprising the step of administering to the subject a composition comprising a recombinant *Listeria* strain provided herein.

In another embodiment, the present invention provides a method for reducing an incidence of relapse of a cancer in a subject, comprising the step of administering to the subject a composition comprising a recombinant *Listeria* strain provided herein.

In another embodiment, the present invention provides a method for suppressing a formation of a tumor in a subject, comprising the step of administering to the subject a composition comprising recombinant *Listeria* strain provided herein.

In another embodiment, the present invention provides a method for inducing a remission of a cancer in a subject, comprising the step of administering to the subject a composition comprising a recombinant *Listeria* strain provided herein.

In another embodiment, the present invention provides a method for impeding a growth of a tumor in a subject, comprising the step of administering to the subject a composition comprising a recombinant *Listeria* strain provided herein.

In another embodiment, the present invention provides a method for reducing a size of a tumor in a subject, comprising the step of administering to the subject a composition comprising a recombinant *Listeria* strain provided herein.

In one embodiment, a disease is an infectious disease, an autoimmune disease, a respiratory disease, a pre-cancerous condition or a cancer.

It will be well appreciated by the skilled artisan that the term "pre-cancerous condition" may encompass dysplasias, preneoplastic nodules; macroregenerative nodules (MRN); low-grade dysplastic nodules (LG-DN); high-grade dysplastic nodules (HG-DN); biliary epithelial dysplasia; foci of altered hepatocytes (FAH); nodules of altered hepatocytes (NAH); chromosomal imbalances; aberrant activation of telomerase; re-expression of the catalytic subunit of telomerase; expression of endothelial cell markers such as CD31, CD34, and BNH9 (see, e.g., Terracciano and Tomillo (2003) Pathologica 95:71-82; Su and Bannasch (2003) Toxicol. Pathol. 31:126-133; Rocken and Carl-McGrath (2001) Dig. Dis. 19:269-278; Kotoula, et al. (2002) Liver 22:57-69; Frachon, et al. (2001) J. Hepatol. 34:850-857; Shimonishi, et al. (2000) J. Hepatobiliary Pancreat. Surg. 7:542-550; Nakanuma, et al. (2003) J. Hepatobiliary Pancreat. Surg. 10:265-281). Methods for diagnosing cancer and dysplasia are disclosed (see, e.g., Riegler (1996) Semin Gastrointest. Dis. 7:74-87; Benvegnu, et al. (1992) Liver 12:80-83; Giannini, et al. (1987) Hepatogastroenterol. 34:95-97; Anthony (1976) Cancer Res. 36:2579-2583).

In one embodiment, an infectious disease is one caused by, but not limited to, any one of the following pathogens: BCG/Tuberculosis, Malaria, *Plasmodium falciparum*, *plasmodium malariae*, *plasmodium vivax*, Rotavirus, Cholera, Diptheria-Tetanus, Pertussis, *Haemophilus influenzae*, Hepatitis B, Human papilloma virus, Influenza seasonal), Influenza A (H1N1) Pandemic, Measles and Rubella, Mumps, Meningococcus A+C, Oral Polio Vaccines, mono, bi and trivalent, Pneumococcal, Rabies, Tetanus Toxoid, Yellow Fever, *Bacillus anthracis* (anthrax), *Clostridium botulinum* toxin (botulism), *Yersinia pestis* (plague), Variola major (smallpox) and other related pox viruses, *Francisella tularensis* (tularemia), Viral hemorrhagic fevers, Arenaviruses (LCM, Junin virus, Machupo virus, Guanarito virus, Lassa Fever), Bunyaviruses (Hantaviruses, Rift Valley Fever), Flaviruses (Dengue), Filoviruses (Ebola, Marburg), *Burkholderia pseudomallei*, *Coxiella burnetii* (Q fever), *Brucella* species (brucellosis), *Burkholderia mallei* (glanders), *Chlamydia psittaci* (Psittacosis), Ricin toxin (from *Ricinus communis*), Epsilon toxin of *Clostridium perfringens*, *Staphylococcus* enterotoxin B, Typhus fever (*Rickettsia prowazekii*), other Rickettsias, Food- and Waterborne Pathogens, Bacteria (Diarrheagenic *E. coli*, Pathogenic Vibrios, *Shigella* species, *Salmonella* BCG/, *Campylobacter jejuni*, *Yersinia enterocolitica*), Viruses (Caliciviruses, Hepatitis A, West Nile Virus, LaCrosse, Calif. encephalitis, VEE, EEE, WEE, Japanese Encephalitis Virus, Kyasanur Forest Virus, Nipah virus, hantaviruses, Tickborne hemorrhagic fever viruses, Chikungunya virus, Crimean-Congo Hemorrhagic fever virus, Tickborne encephalitis viruses, Hepatitis B virus, Hepatitis C virus, Herpes Simplex virus (HSV), Human immunodeficiency virus (HIV), Human papillomavirus (HPV)), Protozoa (*Cryptosporidium parvum*, *Cyclospora cayatanensis*, *Giardia lamblia*, *Entamoeba histolytica*, *Toxoplasma*), Fungi (Microsporidia), Yellow fever, Tuberculosis, including drug-resistant TB, Rabies, Prions, Severe acute respiratory syndrome associated coronavirus (SARS-CoV), *Coccidioides posadasii*, *Coccidioides immitis*, *Bacterial vaginosis*, *Chlamydia trachomatis*, *Cytomegalovirus*, *Granuloma inguinale*, *Hemophilus ducreyi*, *Neisseria gonorrhea*, *Treponema pallidum*, *Trichomonas vaginalis*, or any other infectious disease known in the art that is not listed herein.

In another embodiment, the infectious disease is a livestock infectious disease. In another embodiment, livestock diseases can be transmitted to man and are called "zoonotic diseases." In another embodiment, these diseases include, but are not limited to, Foot and mouth disease, West Nile Virus, rabies, canine parvovirus, feline leukemia virus, equine influenza virus, infectious bovine rhinotracheitis (IBR), pseudorabies, classical swine fever (CSF), IBR, caused by bovine herpesvirus type 1 (BHV-1) infection of cattle, and pseudorabies (Aujeszky's disease) in pigs, toxoplasmosis, anthrax, vesicular stomatitis virus, *rhodococcus equi*, Tularemia, Plague (*Yersinia pestis*), *trichomonas*.

In another embodiment, the disease provided herein is a respiratory or inflammatory disease. In another embodiment, the respiratory or inflammatory disease is chronic obstructive pulmonary disease (COPD). In another embodiment, the disease is asthma.

In one embodiment, live attenuated *Listeria* strains are capable of alleviating asthma symptoms without co-administration of other therapeutic agents, such as anti-inflammatory agents or bronchodilators. In another embodiment, the methods provided herein further comprise the step of co-administering to a subject a live attenuated *Listeria* strain and one or more therapeutic agents. In another embodiment, the therapeutic agent is an anti-asthmatic agent. In another embodiment, the agent is an anti-inflammatory agent, a non-steroidal anti-inflammatory agent, an antibiotic, an anti-chlolinerginc agent, a bronchodilator, a corticosteroid, a short-acting beta-agonist, a long-acting beta-agonist, combination inhalers, an antihistamine, or combinations thereof.

In one embodiment, a disease is a cancer or a tumor. In one embodiment, the tumor is cancerous. In another embodiment, the cancer is breast cancer. In another embodiment, the cancer is a cervical cancer. In another embodiment, the cancer is a Her2 containing cancer. In another embodiment, the cancer is a melanoma. In another embodiment, the cancer is pancreatic cancer. In another embodiment, the cancer is ovarian cancer. In another embodiment, the cancer is gastric cancer. In another embodiment, the cancer is a carcinomatous lesion of the pancreas. In another embodiment, the cancer is pulmonary adenocarcinoma. In another embodiment, it is a glioblastoma multiforme. In another embodiment, the cancer is colorectal adenocarcinoma. In another embodiment, the cancer is pulmonary squamous adenocarcinoma. In another embodiment, the cancer is gastric adenocarcinoma. In another embodiment, the cancer is an ovarian surface epithelial neoplasm (e.g. a benign, proliferative or malignant variety thereof). In another embodiment, the cancer is an oral squamous cell carcinoma. In another embodiment, the cancer is non-small-cell lung carcinoma. In another embodiment, the cancer is an endometrial carcinoma. In another embodiment, the cancer is a bladder cancer. In another embodiment, the cancer is a head and neck cancer. In another embodiment, the cancer is a prostate carcinoma. In another embodiment, the cancer is oropharyngeal cancer. In another embodiment, the cancer is lung cancer. In another embodiment, the cancer is anal cancer. In another embodiment, the cancer is colorectal cancer. In another embodiment, the cancer is esophageal cancer. The cervical tumor targeted by methods of the present invention is, in another embodiment, a squamous cell carcinoma. In another embodiment, the cervical tumor is an adenocarcinoma. In another embodiment, the cervical tumor is an adenosquamous carcinoma. In another embodiment, the cervical tumor is a small cell carcinoma. In another embodiment, the cervical tumor is any other type of cervical tumor known in the art.

A cervical tumor targeted by methods of the present invention is, in one embodiment, a squamous cell carcinoma. In another embodiment, the cervical tumor is an adenocarcinoma. In another embodiment, the cervical tumor is an adenosquamous carcinoma. In another embodiment, the cervical tumor is a small cell carcinoma. In another embodiment, the cervical tumor is any other type of cervical tumor known in the art. Each possibility represents a separate embodiment of the present invention.

In one embodiment, the terms "tumor antigen" "antigenic polypeptide," or "foreign antigen" are used interchangeably herein and include tumor antigens, tumor-associated antigens, angiogenic antigens, or infectious disease antigens. In another embodiment, an antigen provided herein is a self-antigen that is present in the host but the host does not elicit an immune response against it because of immunologic tolerance.

In one embodiment, the antigen is Human Papilloma Virus-E7 (HPV-E7) antigen, which in one embodiment, is from HPV16 (in one embodiment, GenBank Accession No. AAD33253) and in another embodiment, from HPV18 (in one embodiment, GenBank Accession No. P06788). In another embodiment, the antigenic polypeptide is HPV-E6, which in one embodiment, is from HPV16 (in one embodiment, GenBank Accession No. AAD33252, AAM51854, AAM51853, or AAB67615) and in another embodiment, from HPV18 (in one embodiment, GenBank Accession No. P06463). In another embodiment, the antigenic polypeptide is a Her/2-neu antigen. In another embodiment, the antigenic polypeptide is Prostate Specific Antigen (PSA) (in one embodiment, GenBank Accession No. CAD30844, CAD54617, AAA58802, or NP_001639). In another embodiment, the antigenic polypeptide is Stratum Corneum Chymotryptic Enzyme (SCCE) antigen (in one embodiment, GenBank Accession No. AAK69652, AAK69624, AAG33360, AAF01139, or AAC37551). In another embodiment, the antigenic polypeptide is Wilms tumor antigen 1, which in another embodiment is WT-1 Telomerase (GenBank Accession. No. P49952, P22561, NP_659032, CAC39220.2, or EAW68222.1). In another embodiment, the antigenic polypeptide is hTERT or Telomerase (GenBank Accession. No. NM003219 (variant 1), NM198255 (variant 2), NM 198253 (variant 3), or NM 198254 (variant 4). In another embodiment, the antigenic polypeptide is Proteinase 3 (in one embodiment, GenBank Accession No. M29142, M75154, M96839, X55668, NM 00277, M96628 or X56606). In another embodiment, the antigenic polypeptide is Tyrosinase Related Protein 2 (TRP2) (in one embodiment, GenBank Accession No. NP_001913, ABI73976, AAP33051, or Q95119). In another embodiment, the antigenic polypeptide is High Molecular Weight Melanoma Associated Antigen (HMW-MAA) (in one embodiment, GenBank Accession No. NP_001888, AAI28111, or AAQ62842). In another embodiment, the antigenic polypeptide is Testisin (in one embodiment, GenBank Accession No. AAF79020, AAF79019, AAG02255, AAK29360, AAD41588, or NP_659206). In another embodiment, the antigenic polypeptide is NY-ESO-1 antigen (in one embodiment, GenBank Accession No. CAA05908, P78358, AAB49693, or NP_640343). In another embodiment, the antigenic polypeptide is PSCA (in one embodiment, GenBank Accession No. AAH65183, NP_005663, NP_082492, 043653, or CAB97347). In another embodiment, the antigenic polypeptide is Interleukin (IL) 13 Receptor alpha (in one embodiment, GenBank Accession No. NP_000631, NP_001551, NP_032382, NP_598751, NP_001003075, or NP_999506). In another embodiment, the antigenic polypeptide is Carbonic anhydrase IX (CAIX) (in one embodiment, GenBank Accession No. CAI13455, CAI10985, EAW58359, NP_001207, NP_647466, or NP_001101426). In another embodiment, the antigenic polypeptide is carcinoembryonic antigen (CEA) (in one embodiment, GenBank Accession No. AAA66186, CAA79884, CAA66955, AAA51966, AAD15250, or AAA51970.). In another embodiment, the antigenic polypeptide is MAGE-A (in one embodiment, GenBank Accession No. NP_786885, NP_786884, NP_005352, NP_004979, NP_005358, or NP_005353). In another embodiment, the antigenic polypeptide is survivin (in one embodiment, GenBank Accession No. AAC51660, AAY15202, ABF60110, NP_001003019, or NP_001082350). In another embodiment, the antigenic polypeptide is GP100 (in one embodiment, GenBank Accession No. AAC60634, YP_655861, or AAB31176). In another embodiment, the antigenic polypeptide is any other antigenic polypeptide known in the art. In another embodiment, the antigenic peptide of the compositions and methods of the present invention comprise an immunogenic portion of the antigenic polypeptide. Each possibility represents a separate embodiment of the present invention.

In another embodiment, the antigen is telomerase (TERT). In another embodiment, the antigen is LMP-1. In another embodiment, the antigen is p53. In another embodiment, the antigen is mesothelin. In another embodiment, the antigen is EGFRVIII. In another embodiment, the antigen is carboxic anhydrase IX (CAIX). In another embodiment, the antigen is PSMA. In another embodiment, the antigen is HMW-MAA. In another embodiment, the antigen is HIV-1 Gag. In another embodiment, the antigen is Tyrosinase related protein 2. In another embodiment, the antigen is selected from Her-2, HIV-1 Gag, LMP-1, p53, PSMA, carcinoembryonic antigen (CEA), LMP-1,kallikrein-related peptidase 3 (KLK3), KLK9, Muc, Tyrosinase related protein 2, Muc1, FAP, IL-13R alpha 2, PSA (prostate-specific antigen), gp-100, heat-shock protein 70 (HSP-70), beta-HCG, EGFR-III, Granulocyte colony-stimulating factor (G-CSF), Angiogenin, Angiopoietin-1, Del-1, Fibroblast growth factors: acidic (aFGF) or basic (bFGF), Follistatin, Granulocyte colony-stimulating factor (G-CSF), Hepatocyte growth factor (HGF)/scatter factor (SF), Interleukin-8 (IL-8), Leptin, Midkine, Placental growth factor, Platelet-derived endothelial cell growth factor (PD-ECGF), Platelet-derived growth factor-BB (PDGF-BB), Pleiotrophin (PTN), Progranulin, Proliferin, Transforming growth factor-alpha (TGF-alpha), Transforming growth factor-beta (TGF-beta), Tumor necrosis factor-alpha (TNF-alpha), Vascular endothelial growth factor (VEGF)/vascular permeability factor (VPF), VEGFR, VEGFR2 (KDR/FLK-1) or a fragment thereof, FLK-1 or an epitope thereof, FLK-E1, FLK-E2, FLK-I1, endoglin or a fragment thereof, Neuropilin 1 (NRP-1), Angiopoietin 1 (Ang1), Tie2, Platelet-derived growth factor (PDGF), Platelet-derived growth factor receptor (PDGFR), Transforming growth factor-beta (TGF-β), endoglin, TGF-β receptors, monocyte chemotactic protein-1 (MCP-1), VE-cadherin, CD31, ephrin, ICAM-1, V-CAM-1, VAP-1, E-selectin, plasminogen activators, plasminogen activator inhibitor-1, Nitric oxide synthase (NOS), COX-2, AC133, or Id1/Id3, Angiopoietin 3, Angiopoietin 4, Angiopoietin 6, CD105, EDG, HHT1, ORW, ORW1 or a TGFbeta co-receptor, or a combination thereof. In another embodiment, the antigen is a chimeric Her2/neu antigen as disclosed in US Patent Application Publication No. 2011/0142791, which is incorporated by reference herein in its entirety. The use of fragments of antigens provided herein is also encompassed by the present invention.

In another embodiment, the tumor antigen provided herein is a tumor-associated antigen, which in one embodiment, is one of the following tumor antigens: a MAGE (Melanoma-Associated Antigen E) protein, e.g. MAGE 1, MAGE 2, MAGE 3, MAGE 4, a tyrosinase; a mutant ras protein; a mutant p53 protein; p97 melanoma antigen, a ras peptide or p53 peptide associated with advanced cancers; the HPV 16/18 antigens associated with cervical cancers, KLH antigen associated with breast carcinoma, CEA (carcinoembryonic antigen) associated with colorectal cancer, a MART1 antigen associated with melanoma, or the PSA antigen associated with prostate cancer. In another embodiment, the antigen for the compositions and methods provided herein are melanoma-associated antigens, which in one embodiment are TRP-2, MAGE-1, MAGE-3, gp-100, tyrosinase, HSP-70, beta-HCG, or a combination thereof. It is to be understood that a skilled artisan would be able to use any heterologous antigen not mentioned herein but known in the art for use in the methods and compositions provided herein. It is also to be understood that the present invention provides, but is not limited by, an attenuated *Listeria* comprising a nucleic acid that encodes at least one of the antigens disclosed herein. The present invention encompasses nucleic acids encoding mutants, muteins, splice variants, fragments, truncated variants, soluble variants, extracellular domains, intracellular domains, mature sequences, and the like, of the disclosed antigens. Provided are nucleic acids encoding epitopes, oligo- and polypeptides of these antigens. Also provided are codon optimized embodiments, that is, optimized for expression in *Listeria*. The cited references, GenBank Acc. Nos., and the nucleic acids, peptides, and polypeptides disclosed herein, are all incorporated herein by reference in their entirety. In another embodiment, the selected nucleic acid sequence can encode a full length or a truncated gene, a fusion or tagged gene, and can be a cDNA, a genomic DNA, or a DNA fragment, preferably, a cDNA. It can be mutated or otherwise modified as desired. These modifications include codon optimizations to optimize codon usage in the selected host cell or bacteria, i.e. *Listeria*. The selected sequence can also encode a secreted, cytoplasmic, nuclear, membrane bound or cell surface polypeptide.

In one embodiment, vascular endothelial growth factor (VEGF) is an important signaling protein involved in both vasculogenesis (the formation of the embryonic circulatory system) and angiogenesis (the growth of blood vessels from pre-existing vasculature). In one embodiment, VEGF activity is restricted mainly to cells of the vascular endothelium, although it does have effects on a limited number of other cell types (e.g. stimulation monocyte/macrophage migration). In vitro, VEGF has been shown to stimulate endothelial cell mitogenesis and cell migration. VEGF also enhances microvascular permeability and is sometimes referred to as vascular permeability factor.

In one embodiment, all of the members of the VEGF family stimulate cellular responses by binding to tyrosine kinase receptors (the VEGFRs) on the cell surface, causing them to dimerize and become activated through transphosphorylation. The VEGF receptors have an extracellular portion consisting of 7 immunoglobulin-like domains, a single transmembrane spanning region and an intracellular portion containing a split tyrosine-kinase domain.

In one embodiment, VEGF-A is a VEGFR-2 (KDR/Flk-1) ligand as well as a VEGFR-1 (Flt-1) ligand. In one embodiment, VEGFR-mediates almost all of the known cellular responses to VEGF. The function of VEGFR-1 is less well defined, although it is thought to modulate VEGFR-2 signaling, in one embodiment, via sequestration of VEGF from VEGFR-2 binding, which in one embodiment, is particularly important during vasculogenesis in the embryo. In one embodiment, VEGF-C and VEGF-D are ligands of the VEGFR-3 receptor, which in one embodiment, mediates lymphangiogenesis.

In one embodiment, the antigen of the present invention is a VEGF receptor or a fragment thereof, which in one embodiment, is a VEGFR-2 and, in another embodiment, a VEGFR-1, and, in another embodiment, VEGFR-3.

In one embodiment, vascular Endothelial Growth Factor Receptor 2 (VEGFR2) is highly expressed on activated endothelial cells (ECs) and participates in the formation of new blood vessels. In one embodiment, VEGFR2 binds all 5 isoforms of VEGF. In one embodiment, signaling of VEGF through VEGFR2 on ECs induces proliferation, migration, and eventual differentiation. In one embodiment, the mouse homologue of VEGFR2 is the fetal liver kinase gene-1 (Flk-1), which is a strong therapeutic target, and has important roles in tumor growth, invasion, and metastasis. In one embodiment, VEGFR2 is also referred to as kinase insert domain receptor (a type III receptor tyrosine kinase) (KDR), cluster of differentiation 309 (CD309), FLK1, Ly73, Krd-1, VEGFR, VEGFR-2, or 6130401C07.

In other embodiments, the antigen is derived from a fungal pathogen, bacteria, parasite, helminth, or viruses. In other embodiments, the antigen is selected from tetanus toxoid, hemagglutinin molecules from influenza virus, diphtheria toxoid, HIV gp120, HIV gag protein, IgA protease, insulin peptide B, *Spongospora subterranea* antigen, vibriose antigens, *Salmonella* antigens, pneumococcus antigens, respiratory syncytial virus antigens, *Haemophilus influenza* outer membrane proteins, *Helicobacter* pylori urease, *Neisseria meningitidis* pilins, *N. gonorrhoeae* pilins, the melanoma-associated antigens (TRP-2, MAGE-1, MAGE-3, gp-100, tyrosinase, MART-1, HSP-70, beta-HCG), human papilloma virus antigens E1 and E2 from type HPV-16, -18, -31, -33, -35 or -45 human papilloma viruses, the tumor antigens CEA, the ras protein, mutated or otherwise, the p53 protein, mutated or otherwise, Mud, or pSA.

In other embodiments, the antigen is associated with one of the following diseases; cholera, diphtheria, *Haemophilus*, hepatitis A, hepatitis B, influenza, measles, meningitis, mumps, pertussis, small pox, pneumococcal pneumonia, polio, rabies, rubella, tetanus, tuberculosis, typhoid, Varicella-zoster, whooping cough3 yellow fever, the immunogens and antigens from Addison's disease, allergies, anaphylaxis, Bruton's syndrome, cancer, including solid and blood borne tumors, eczema, Hashimoto's thyroiditis, polymyositis, dermatomyositis, type 1 diabetes mellitus, acquired immune deficiency syndrome, transplant rejection, such as kidney, heart, pancreas, lung, bone, and liver transplants, Graves' disease, polyendocrine autoimmune disease, hepatitis, microscopic polyarteritis, polyarteritis nodosa, pemphigus, primary biliary cirrhosis, pernicious anemia, coeliac disease, antibody-mediated nephritis, glomerulonephritis, rheumatic diseases, systemic lupus erthematosus, rheumatoid arthritis, seronegative spondylarthritides, rhinitis, sjogren's syndrome, systemic sclerosis, sclerosing cholangitis, Wegener's granulomatosis, dermatitis herpetiformis, psoriasis, vitiligo, multiple sclerosis, encephalomyelitis, Guillain-Barre syndrome, myasthenia gravis, Lambert-Eaton syndrome, sclera, episclera, uveitis, chronic mucocutaneous candidiasis, urticaria, transient hypogammaglobulinemia of infancy, myeloma, X-linked hyper IgM syndrome, Wiskott-Aldrich syndrome, ataxia telangiectasia, autoimmune hemolytic anemia, autoimmune thrombocytopenia, autoimmune neutropenia, Waldenstrom's macroglobulinemia, amyloidosis, chronic lymphocytic leukemia, non-Hodgkin's lymphoma, malarial circumsporozite protein, microbial antigens, viral antigens, autoantigens, and lesteriosis.

In another embodiment, an HPV E6 antigen is utilized instead of or in addition to an E7 antigen in a method of the present invention for treating, protecting against, or inducing an immune response against a cervical cancer.

In another embodiment, an ActA protein fragment is utilized instead of or in addition to an LLO fragment in a method of the present invention for treating, protecting against, or inducing an immune response against a cervical cancer.

In another embodiment, a PEST amino acid sequence-containing protein fragment is utilized instead of or in addition to an LLO fragment in a method of the present invention for treating, protecting against, or inducing an immune response against a cervical cancer.

In another embodiment, the present invention provides a method for inducing an anti-E7 cytotoxic T cell (CTL) response in a subject, comprising the step of administering to the subject a recombinant *Listeria* strain, the recombinant *Listeria* strain comprising a recombinant polypeptide comprising an N-terminal fragment of an LLO protein and an HPV E7 antigen, thereby inducing an anti-E7 CTL response in a subject. In another embodiment, the recombinant *Listeria* strain comprises a plasmid that encodes the recombinant polypeptide. In another embodiment, the method further comprises the step of boosting the subject with a recombinant *Listeria* strain of the present invention. In another embodiment, the method further comprises the step of boosting the subject with an immunogenic composition comprising an E7 antigen. In another embodiment, the method further comprises the step of boosting the subject with an immunogenic composition that directs a cell of the subject to express an E7 antigen. In another embodiment, the CTL response is capable of therapeutic efficacy against an HPV-mediated disease, disorder, or symptom. In another embodiment, the CTL response is capable of prophylactic efficacy against an HPV-mediated disease, disorder, or symptom. Each possibility represents a separate embodiment of the present invention.

In another embodiment, the present invention provides a method of treating or ameliorating an HPV-mediated disease, disorder, or symptom in a subject, comprising the step of administering to the subject a recombinant *Listeria* strain, the recombinant *Listeria* strain comprising a recombinant polypeptide comprising an N-terminal fragment of an LLO protein and an HPV E7 antigen, whereby the recombinant *Listeria* strain induces an immune response against the E7 antigen, thereby treating or ameliorating an HPV-mediated disease, disorder, or symptom in a subject. In another embodiment, the subject is a human subject. In another embodiment, the subject is a non-human mammal. In another embodiment, the subject is any other type of subject known in the art. Each possibility represents a separate embodiment of the present invention.

In another embodiment, the HPV-mediated disease, disorder, or symptom is genital warts. In another embodiment, the HPV-mediated disease, disorder, or symptom is non-genital warts. In another embodiment, the HPV-mediated disease, disorder, or symptom is a respiratory papilloma. In another embodiment, the HPV-mediated disease, disorder, or symptom is any other HPV-mediated disease, disorder, or symptom known in the art. Each possibility represents a separate embodiment of the present invention.

The antigen of methods and compositions of the present invention is, in another embodiment, an HPV E7 protein. In another embodiment, the antigen is an HPV E6 protein. In another embodiment, the antigen is any other HPV protein known in the art. Each possibility represents a separate embodiment of the present invention.

"E7 antigen" refers, in another embodiment, to an E7 protein. In another embodiment, the term refers to an E7 fragment. In another embodiment, the term refers to an E7 peptide. In another embodiment, the term refers to any other type of E7 antigen known in the art. Each possibility represents a separate embodiment of the present invention.

The E7 protein of methods and compositions of the present invention is, in another embodiment, an HPV 16 E7 protein. In another embodiment, the E7 protein is an HPV-18 E7 protein. In another embodiment, the E7 protein is an HPV-31 E7 protein. In another embodiment, the E7 protein is an HPV-35 E7 protein. In another embodiment, the E7 protein is an HPV-39 E7 protein. In another embodiment, the E7 protein is an HPV-45 E7 protein. In another embodiment, the E7 protein is an HPV-51 E7 protein. In another embodiment, the E7 protein is an HPV-52 E7 protein. In another embodiment, the E7 protein is an HPV-58 E7 protein. In another embodiment, the E7 protein is an E7 protein of a high-risk HPV type. In another embodiment, the E7 protein is an E7 protein of a mucosal HPV type. Each possibility represents a separate embodiment of the present invention.

"E6 antigen" refers, in another embodiment, to an E6 protein. In another embodiment, the term refers to an E6 fragment. In another embodiment, the term refers to an E6 peptide. In another embodiment, the term refers to any other type of E6 antigen known in the art. Each possibility represents a separate embodiment of the present invention.

The E6 protein of methods and compositions of the present invention is, in another embodiment, an HPV 16 E6 protein. In another embodiment, the E6 protein is an HPV-18 E6 protein. In another embodiment, the E6 protein is an HPV-31 E6 protein. In another embodiment, the E6 protein is an HPV-35 E6 protein. In another embodiment, the E6 protein is an HPV-39 E6 protein. In another embodiment, the E6 protein is an HPV-45 E6 protein. In another embodiment, the E6 protein is an HPV-51 E6 protein. In another embodiment, the E6 protein is an HPV-52 E6 protein. In another embodiment, the E6 protein is an HPV-58 E6 protein. In another embodiment, the E6 protein is an E6 protein of a high-risk HPV type. In another embodiment, the E6 protein is an E6 protein of a mucosal HPV type. Each possibility represents a separate embodiment of the present invention.

In one embodiment, combinations of the E6 and E7 antigens are contemplated to fall within the scope of a "heterologous antigen" provided herein.

The immune response induced by methods and compositions of the present invention is, in another embodiment, a T cell response. In another embodiment, the immune response comprises a cytotoxic T cell response. In another embodiment, the immune response comprises a T cell response. In another embodiment, the response is a CD8$^+$ T cell response. In another embodiment, the response comprises a CD8$^+$ T cell response. Each possibility represents a separate embodiment of the present invention.

The N-terminal LLO protein fragment of methods and compositions of the present invention comprises, in another embodiment, SEQ ID No: 2. In another embodiment, the fragment comprises an LLO signal peptide. In another embodiment, the fragment comprises SEQ ID No: 2. In another embodiment, the fragment consists approximately of SEQ ID No: 2. In another embodiment, the fragment consists essentially of SEQ ID No: 2. In another embodiment, the fragment corresponds to SEQ ID No: 2. In another embodiment, the fragment is homologous to SEQ ID No: 2. In another embodiment, the fragment is homologous to a fragment of SEQ ID No: 2. The ΔLLO used in some of the Examples was 416 AA long (exclusive of the signal sequence), as 88 residues from the amino terminus which is inclusive of the activation domain containing cysteine 484 were truncated. It will be clear to those skilled in the art that any ΔLLO without the activation domain, and in particular without cysteine 484, are suitable for methods and compositions of the present invention. In another embodiment, fusion of an E7 and/or E6 antigen to any ΔLLO, including a PEST amino acid AA sequence, SEQ ID NO: 1, enhances cell mediated and anti-tumor immunity of the antigen. Each possibility represents a separate embodiment of the present invention.

The LLO protein utilized to construct vaccines of the present invention has, in another embodiment, the sequence: MKKIMLVFITLILVSLPIAQQTEAKDASAFNKENSISS-MAPPASPPASPKTPIEKKHADE IDKYIQGLDYNKN-NVLVYHGDAVTNVPPRKGYKDGNEYIVVEKKKK-SINQNNADIQ VVNAISSLTYPGALVKANSELVEN-QPDVLPVKRDSLTLSIDLPGMTNQDNKIVVKNA TKSNVNNAVNTLVERWNEKYAQAYPNVSAKIDYDD-EMAYSESQLIAKFGTAFKAV NNSLNVNFGAISEGK-MQEEVISFKQIYYNVNVNEPTRPSRFFGKAVT-KEQLQALGVN AENPPAYISSVAYGRQVYLKLSTNS-HSTKVKAAFDAAVSGKSVSGDVELTNIIKNSSF KAVI-YGGSAKDEVQIIDGNLGDLRDILKKGATFNRETPGV-PIAYTTNFLKDNELAVIK NNSEYIETTSKAYTDG-KINIDHSGGYVAQFNISWDEVNYDPEGNEIVQHKN-WSENNK SKLAHFTSSIYLPGNARNINVYAKECT-GLAWEWWRTVIDDRNLPLVKNRNISIWGTT LYP-KYSNKVDNPIE (GenBank Accession No. P13128; SEQ ID NO: 3; nucleic acid sequence is set forth in GenBank Accession No. X15127). The first 25 AA of the proprotein corresponding to this sequence are the signal sequence and are cleaved from LLO when it is secreted by the bacterium. Thus, in this embodiment, the full length active LLO protein is 504 residues long. In another embodiment, a full length LLO protein has an amino acid sequence of any full length wild-type LLO protein known in the art. In another embodiment, SEQ ID NO: 3 is used as the source of the LLO fragment incorporated in a vaccine of the present invention. Each possibility represents a separate embodiment of the present invention.

In another embodiment, the N-terminal fragment of an LLO protein utilized in compositions and methods of the present invention has the sequence:

```
                                             (SEQ ID NO: 2)
MKKIMLVFITLILVSLPIAQQTEAKDASAFNKENSISSVAPPASPPASPK

TPIEKKHADEIDKYIQGLDYNKNNVLVYHGDAVTNVPPRKGYKDGNEYIV

VEKKKKSINQNNADIQVVNAISSLTYPGALVKANSELVENQPDVLPVKRD

SLTLSIDLPGMTNQDNKIVVKNATKSNVNNAVNTLVERWNEKYAQAYSNV

SAKIDYDDEMAYSESQLIAKFGTAFKAVNNSLNVNFGAISEGKMQEEVIS

FKQIYYNVNVNEPTRPSRFFGKAVTKEQLQALGVNAENPPAYISSVAYGR

QVYLKLSTNSHSTKVKAAFDAAVSGKSVSGDVELTNIIKNSSFKAVIYGG

SAKDEVQIIDGNLGDLRDILKKGATFNRETPGVPIAYTTNFLKDNELAVI

KNNSEYIETTSKAYTDGKINIDHSGGYVAQFNISWDEVNYD.
```

In another embodiment, the LLO fragment has the sequence:

```
                                             (SEQ ID NO: 4)
MKKIMLVFITLILVSLPIAQQTEAKDASAFNKENSISSVAPPASPPASPK

TPIEKKHADEIDKYIQGLDYNKNNVLVYHGDAVTNVPPRKGYKDGNEYIV

VEKKKKSINQNNADIQVVNAISSLTYPGALVKANSELVENQPDVLPVKRD

SLTLSIDLPGMTNQDNKIVVKNATKSNVNNAVNTLVERWNEKYAQAYSNV

SAKIDYDDEMAYSESQLIAKFGTAFKAVNNSLNVNFGAISEGKMQEEVIS

FKQIYYNVNVNEPTRPSRFFGKAVTKEQLQALGVNAENPPAYISSVAYGR

QVYLKLSTNSHSTKVKAAFDAAVSGKSVSGDVELTNIIKNSSFKAVIYGG

SAKDEVQIIDGNLGDLRDILKKGATFNRETPGVPIAYTTNFLKDNELAVI

KNNSEYIETTSKAYTD.
```

In one embodiment, "Listeriolysin O protein," or "LLO protein," refer to a wild-type LLO protein unless stated to be a fragment of the same. In another embodiment, "truncated LLO" or "ΔLLO" refers to a fragment of LLO that comprises the PEST amino acid domain. In another embodiment, the terms refer to an LLO fragment that comprises a PEST sequence. In another embodiment, the terms refer to an LLO fragment that comprises a putative PEST sequence.

In another embodiment, the terms refer to an LLO fragment that does not contain the activation domain at the carboxy terminus and does not include cysteine 484. In another embodiment, the terms refer to an LLO fragment that is not hemolytic. In another embodiment, the LLO fragment is rendered non-hemolytic by deletion or mutation of the activation domain. In another embodiment, the LLO fragment is rendered non-hemolytic by deletion or mutation of cysteine 484. In another embodiment, the LLO fragment is rendered non-hemolytic by deletion or mutation at another location. Each possibility represents a separate embodiment of the present invention.

In another embodiment, the LLO fragment consists of about the first 441 AA of a wild-type LLO protein. In another embodiment, the LLO fragment consists of about the first 420 AA of LLO. In another embodiment, the LLO fragment is a non-hemolytic form of the LLO protein.

In another embodiment, the LLO fragment contains residues of a homologous LLO protein that correspond to one of the above AA ranges. The residue numbers need not, in another embodiment, correspond exactly with the residue numbers enumerated above; e.g. if the homologous LLO protein has an insertion or deletion, relative to an LLO protein utilized herein, then the residue numbers can be adjusted accordingly.

In another embodiment, the LLO fragment is any other LLO fragment known in the art. Each possibility represents a separate embodiment of the present invention.

In another embodiment, the recombinant polypeptide of methods of the present invention is expressed by the recombinant *Listeria* strain. In another embodiment, the expression is mediated by a nucleotide molecule carried by the recombinant *Listeria* strain.

In another embodiment, the recombinant *Listeria* strain expresses the recombinant polypeptide by means of a plasmid that encodes the recombinant polypeptide. In another embodiment, the plasmid comprises a gene encoding a bacterial transcription factor. In another embodiment, the plasmid encodes a *Listeria* transcription factor. In another embodiment, the transcription factor is PrfA. In another embodiment, the PrfA is a mutant PrfA. In another embodiment, the PrfA contains a D133V amino acid mutation. In another embodiment, the transcription factor is any other transcription factor known in the art. In another embodiment, the mutant PrfA encoded by said plasmid complements a genomic prfA mutation, deletion or inactivation in said *Listeria*. In another embodiment, the mutant PrfA encoded by said plasmid restores partial PrfA function in said *Listeria* having a genomic prfA mutation, deletion or inactivation. Each possibility represents a separate embodiment of the present invention.

In another embodiment, a plasmid comprised by a recombinant *Listeria* provided herein comprises an open reading frame encoding a metabolic enzyme. In another embodiment, the plasmid comprises a third open reading frame encoding a metabolic enzyme. In another embodiment, the metabolic enzyme is a bacterial metabolic enzyme. In another embodiment, the metabolic enzyme is a Listerial metabolic enzyme. In another embodiment, the metabolic enzyme is an amino acid metabolism enzyme. In another embodiment, the amino acid metabolism gene is involved in a cell wall synthesis pathway. In another embodiment, the metabolic enzyme is the product of a D-amino acid aminotransferase gene (dat). In another embodiment, the metabolic enzyme is the product of an alanine racemase gene (dal). In another embodiment, the metabolic enzyme is any other metabolic enzyme known in the art. In another embodiment, the plasmid carries an open reading frame encoding a dal protein. In another embodiment, the plasmid carries an open reading frame encoding a dat protein. In another embodiment, the plasmid carries an open reading frame encoding a dal and dat protein. In another embodiment, when the plasmid carries an open reading frame encoding a dal and/or dat protein, it is to complement a dal/dat mutation in a recombinant *Listeria* strain. Hence, dal/dat recombinant *Listerias* are also envisioned for use in the present invention. In another embodiment, the recombinant *Listeria* provided herein comprises a dal/dat mutation in addition to any other mutation further described herein. Each possibility represents a separate embodiment of the present invention.

In another embodiment, a *Listeria* strain provided herein is deficient in an AA metabolism enzyme. In another embodiment, the *Listeria* strain is deficient in a D-glutamic acid synthase gene. In another embodiment, the *Listeria* strain is deficient in the dat gene. In another embodiment, the *Listeria* strain is deficient in the dal gene. In another embodiment, the *Listeria* strain is deficient in the dga gene. In another embodiment, the *Listeria* strain is deficient in a gene involved in the synthesis of diaminopimelic acid (DAP). In another embodiment, the *Listeria* strain is deficient in a gene involved in the synthesis of Cysteine synthase A (CysK). In another embodiment, the gene is vitamin-B12 independent methionine synthase. In another embodiment, the gene is trpA. In another embodiment, the gene is trpB. In another embodiment, the gene is trpE. In another embodiment, the gene is asnB. In another embodiment, the gene is gltD. In another embodiment, the gene is gltB. In another embodiment, the gene is leuA. In another embodiment, the gene is argG. In another embodiment, the gene is thrC. In another embodiment, the *Listeria* strain is deficient in one or more of the genes described hereinabove.

In another embodiment, a *Listeria* strain provided herein is deficient in a synthase gene. In another embodiment, the gene is an AA synthesis gene. In another embodiment, the gene is folP. In another embodiment, the gene is dihydrouridine synthase family protein. In another embodiment, the gene is ispD. In another embodiment, the gene is ispF. In another embodiment, the gene is phosphoenolpyruvate synthase. In another embodiment, the gene is hisF. In another embodiment, the gene is hisH. In another embodiment, the gene is fliI. In another embodiment, the gene is ribosomal large subunit pseudouridine synthase. In another embodiment, the gene is ispD. In another embodiment, the gene is bifunctional GMP synthase/glutamine amidotransferase protein. In another embodiment, the gene is cobS. In another embodiment, the gene is cobB. In another embodiment, the gene is cbiD. In another embodiment, the gene is uroporphyrin-III C-methyltransferase/uroporphyrinogen-III synthase. In another embodiment, the gene is cobQ. In another embodiment, the gene is uppS. In another embodiment, the gene is truB. In another embodiment, the gene is dxs. In another embodiment, the gene is mvaS. In another embodiment, the gene is dapA. In another embodiment, the gene is ispG. In another embodiment, the gene is folC. In another embodiment, the gene is citrate synthase. In another embodiment, the gene is argJ. In another embodiment, the gene is 3-deoxy-7-phosphoheptulonate synthase. In another embodiment, the gene is indole-3-glycerol-phosphate synthase. In another embodiment, the gene is anthranilate synthase/glutamine amidotransferase component. In another embodiment, the gene is menB. In another embodiment, the gene is menaquinone-specific isochorismate synthase. In another embodiment, the gene is phosphoribosylformylglycinamidine synthase I or II. In another embodiment, the gene is phosphoribosylaminoimidazole-succinocarboxamide synthase. In another embodiment, the gene is carB. In another embodiment, the gene is carA. In another embodiment, the gene is thyA. In another embodiment, the gene is mgsA. In another embodiment, the gene is aroB. In another embodiment, the gene is hepB. In another embodiment, the gene is rluB. In another embodiment, the gene is ilvB. In another embodiment, the gene is ilvN. In another embodiment, the gene is alsS. In another embodiment, the gene is fabF. In another embodiment, the gene is fabH. In another embodiment, the gene is pseudouridine synthase. In another embodiment, the gene is pyrG. In another embodiment, the gene is truA. In another embodiment, the gene is pabB. In another embodiment, the gene is an atp synthase gene (e.g. atpC, atpD-2, aptG, atpA-2, etc).

In another embodiment, the gene is phoP. In another embodiment, the gene is aroA. In another embodiment, the gene is aroC. In another embodiment, the gene is aroD. In another embodiment, the gene is plcB.

In another embodiment, a Listeria strain provided herein is deficient in a peptide transporter. In another embodiment, the gene is ABC transporter/ATP-binding/permease protein. In another embodiment, the gene is oligopeptide ABC transporter/oligopeptide-binding protein. In another embodiment, the gene is oligopeptide ABC transporter/permease protein. In another embodiment, the gene is zinc ABC transporter/zinc-binding protein. In another embodiment, the gene is sugar ABC transporter. In another embodiment, the gene is phosphate transporter. In another embodiment, the gene is ZIP zinc transporter. In another embodiment, the gene is drug resistance transporter of the EmrB/QacA family. In another embodiment, the gene is sulfate transporter. In another embodiment, the gene is proton-dependent oligopeptide transporter. In another embodiment, the gene is magnesium transporter. In another embodiment, the gene is formate/nitrite transporter. In another embodiment, the gene is spermidine/putrescine ABC transporter. In another embodiment, the gene is Na/Pi-cotransporter. In another embodiment, the gene is sugar phosphate transporter. In another embodiment, the gene is glutamine ABC transporter. In another embodiment, the gene is major facilitator family transporter. In another embodiment, the gene is glycine betaine/L-proline ABC transporter. In another embodiment, the gene is molybdenum ABC transporter. In another embodiment, the gene is techoic acid ABC transporter. In another embodiment, the gene is cobalt ABC transporter. In another embodiment, the gene is ammonium transporter. In another embodiment, the gene is amino acid ABC transporter. In another embodiment, the gene is cell division ABC transporter. In another embodiment, the gene is manganese ABC transporter. In another embodiment, the gene is iron compound ABC transporter. In another embodiment, the gene is maltose/maltodextrin ABC transporter. In another embodiment, the gene is drug resistance transporter of the Bcr/CflA family. In another embodiment, the gene is a subunit of one of the above proteins.

In one embodiment, provided herein is a nucleic acid molecule that is used to transform the Listeria in order to arrive at a recombinant Listeria. In another embodiment, the nucleic acid provided herein used to transform *Listeria* lacks a virulence gene. In another embodiment, the nucleic acid molecule is integrated into the *Listeria* genome and carries a non-functional virulence gene. In another embodiment, the virulence gene is mutated in the recombinant *Listeria*. In yet another embodiment, the nucleic acid molecule is used to inactivate the endogenous gene present in the *Listeria* genome. In yet another embodiment, the virulence gene is an actA gene, an inlA gene, and inlB gene, an inlC gene, inlJ gene, a plbC gene, a bsh gene, or a prfA gene. It is to be understood by a skilled artisan, that the virulence gene can be any gene known in the art to be associated with virulence in the recombinant *Listeria*.

In one embodiment, a live attenuated *Listeria* provided herein is a recombinant *Listeria*. In another embodiment, a recombinant *Listeria* provided herein comprises a mutation of a genomic intemalin C (inlC) gene. In another embodiment, the recombinant *Listeria* comprises a mutation or a deletion of a genomic actA gene and a genomic internalin C gene. In one embodiment, translocation of *Listeria* to adjacent cells is inhibited by the deletion of the actA gene and/or the inlC gene, which are involved in the process, thereby resulting in unexpectedly high levels of attenuation with increased immunogenicity and utility as a strain backbone. Each possibility represents a separate embodiment of the present invention.

It will be appreciated by a skilled artisan that the term "attenuation," may encompass a diminution in the ability of the bacterium to cause disease in an animal. In other words, for example the pathogenic characteristics of the attenuated *Listeria* strain have been lessened compared with wild-type *Listeria*, although the attenuated *Listeria* is capable of growth and maintenance in culture. Using as an example the intravenous inoculation of Balb/c mice with an attenuated *Listeria*, the lethal dose at which 50% of inoculated animals survive ($LD_{50}$) is preferably increased above the $LD_{50}$ of wild-type *Listeria* by at least about 10-fold, more preferably by at least about 100-fold, more preferably at least about 1,000 fold, even more preferably at least about 10,000 fold, and most preferably at least about 100,000-fold. An attenuated strain of *Listeria* is thus one which does not kill an animal to which it is administered, or is one which kills the animal only when the number of bacteria administered is vastly greater than the number of wild type non-attenuated bacteria which would be required to kill the same animal. An attenuated bacterium should also be construed to mean one which is incapable of replication in the general environment because the nutrient required for its growth is not present therein. Thus, the bacterium is limited to replication in a controlled environment wherein the required nutrient is provided. The attenuated strains of the present invention are therefore environmentally safe in that they are incapable of uncontrolled replication.

In yet another embodiment, a *Listeria* strain provided herein is an inlA mutant, an inlB mutant, an inlC mutant, an inlJ mutant, prfA mutant, actA mutant, a dal/dat mutant, a prfA mutant, a plcB deletion mutant, or a double mutant lacking both plcA and plcB. In another embodiment, the *Listeria* comprises a deletion or mutation of these genes individually or in combination. In another embodiment, the *Listeria* provided herein lack each one of genes. In another embodiment, the *Listeria* provided herein lack at least one and up to ten of any gene provided herein, including the actA, prfA, and dal/dat genes. In another embodiment, the prfA mutant is a D133V PrfA mutant.

In one embodiment, the metabolic gene, the virulence gene, etc. is lacking in a chromosome of the *Listeria* strain. In another embodiment, the metabolic gene, virulence gene, etc. is lacking in the chromosome and in any episomal genetic element of the *Listeria* strain. In another embodiment, the metabolic gene, virulence gene, etc. is lacking in the genome of the virulence strain. In one embodiment, the virulence gene is mutated in the chromosome. In another embodiment, the virulence gene is deleted from the chromosome. In another embodiment, the metabolic gene, the virulence gene, etc. is mutated in a chromosome of the *Listeria* strain. In another embodiment, the metabolic gene, virulence gene, etc. is mutated in the chromosome and in any episomal genetic element of the *Listeria* strain. In another embodiment, the metabolic gene, virulence gene, etc. is mutated in the genome of the virulence strain. In another embodiment, the virulence gene is deleted from the chromosome. Each possibility represents a separate embodiment of the present invention.

In one embodiment, a recombinant *Listeria* strain provided herein is attenuated. In another embodiment, the recombinant *Listeria* lacks the actA virulence gene. In another embodiment, the recombinant *Listeria* lacks the prfA virulence gene. In another embodiment, the recombinant *Listeria* lacks the inlB gene. In another embodiment, the recombinant *Listeria* lacks both, the actA and inlB genes. In another embodiment, the recombinant *Listeria* strain provided herein comprises an inactivating mutation of the endogenous actA gene. In another embodiment, the recombinant *Listeria* strain provided herein comprises an inactivating mutation of the endogenous inlB gene. In another embodiment, the recombinant *Listeria* strain provided herein comprises an inactivating mutation of the endogenous inlC gene. In another embodiment, the recombinant *Listeria* strain provided herein comprises an inactivating mutation of the endogenous actA and inlB genes. In another embodiment, the recombinant *Listeria* strain provided herein comprises an inactivating mutation of the endogenous actA and inlC genes. In another embodiment, the recombinant *Listeria* strain provided herein comprises an inactivating mutation of the endogenous actA, inlB, and inlC genes. In another embodiment, the recombinant *Listeria* strain provided herein comprises an inactivating mutation of the endogenous actA, inlB, and inlC genes. In another embodiment, the recombinant *Listeria* strain provided herein comprises an inactivating mutation of the endogenous actA, inlB, and inlC genes. In another embodiment, the recombinant *Listeria* strain provided herein comprises an inactivating mutation in any single gene or combination of the following genes: actA, dal, dat, inlB, inlC, prfA, plcA, plcB.

It will be appreciated by a skilled artisan that the term "mutation" and grammatical equivalents thereof, include any type of mutation or modification to the sequence (nucleic acid or amino acid sequence), and includes a deletion mutation, a truncation, an inactivation, a disruption, or a translocation. These types of mutations are readily known in the art.

In one embodiment, in order to select for auxotrophic bacteria comprising a plasmid encoding a metabolic enzyme or a complementing gene provided herein, transformed auxotrophic bacteria are grown on a media that will select for expression of the amino acid metabolism gene or the complementing gene. In another embodiment, a bacteria auxotrophic for D-glutamic acid synthesis is transformed with a plasmid comprising a gene for D-glutamic acid synthesis, and the auxotrophic bacteria will grow in the absence of D-glutamic acid, whereas auxotrophic bacteria that have not been transformed with the plasmid, or are not expressing the plasmid encoding a protein for D-glutamic acid synthesis, will not grow. In another embodiment, a bacterium auxotrophic for D-alanine synthesis will grow in the absence of D-alanine when transformed and expressing the plasmid of the present invention if the plasmid comprises an isolated nucleic acid encoding an amino acid metabolism enzyme for D-alanine synthesis. Such methods for making appropriate media comprising or lacking necessary growth factors, supplements, amino acids, vitamins, antibiotics, and the like are well known in the art, and are available commercially (Becton-Dickinson, Franklin Lakes, N.J.).

In another embodiment, once the auxotrophic bacteria comprising the plasmid of the present invention have been selected on appropriate media, the bacteria are propagated in the presence of a selective pressure. Such propagation comprises growing the bacteria in media without the auxotrophic factor. The presence of the plasmid expressing an amino acid metabolism enzyme in the auxotrophic bacteria ensures that the plasmid will replicate along with the bacteria, thus continually selecting for bacteria harboring the plasmid. The skilled artisan, when equipped with the present disclosure and methods herein will be readily able to scale-up the production of the *Listeria* vaccine vector by adjusting the volume of the media in which the auxotrophic bacteria comprising the plasmid are growing.

The skilled artisan will appreciate that, in another embodiment, other auxotroph strains and complementation systems are adopted for the use with this invention.

In one embodiment, a recombinant *Listeria* strain provided herein expresses a recombinant polypeptide. In another embodiment, a recombinant *Listeria* strain comprises a plasmid that encodes a recombinant polypeptide. In another embodiment, a recombinant nucleic acid provided herein is in a plasmid in the recombinant *Listeria* strain provided herein. In another embodiment, the plasmid is an episomal plasmid that does not integrate into the recombinant *Listeria* strain's chromosome. In another embodiment, the plasmid is an integrative plasmid that integrates into the *Listeria* strain's chromosome. In another embodiment, the plasmid is a multicopy plasmid. In another embodiment, the recombinant *Listeria* strain is administered to the human subject at a dose of $1\times10^9$-$3.31\times10^{10}$ CFU. In another embodiment, the dose is $5$-$500\times10^8$ CFU. In another embodiment, the dose is $7$-$500\times10^8$ CFU. In another embodiment, the dose is $10$-$500\times10^8$ CFU. In another embodiment, the dose is $20$-$500\times10^8$ CFU. In another embodiment, the dose is $30$-$500\times10^8$ CFU. In another embodiment, the dose is $50$-$500\times10^8$ CFU. In another embodiment, the dose is $70$-$500\times10^8$ CFU. In another embodiment, the dose is $100$-$500\times10^8$ CFU. In another embodiment, the dose is $150$-$500\times10^8$ CFU. In another embodiment, the dose is $5$-$300\times10^8$ CFU. In another embodiment, the dose is $5$-$200\times10^8$ CFU. In another embodiment, the dose is $5$-$150\times10^8$ CFU. In another embodiment, the dose is $5$-$100\times10^8$ CFU. In another embodiment, the dose is $5$-$70\times10^8$ CFU. In another embodiment, the dose is $5$-$50\times10^8$ CFU. In another embodiment, the dose is $5$-$30\times10^8$ CFU. In another embodiment, the dose is $5$-$20\times10^8$ CFU. In another embodiment, the dose is $1$-$30\times10^9$ CFU. In another embodiment, the dose is $1$-$20\times10^9$ CFU. In another embodiment, the dose is $2$-$30\times10^9$ CFU. In another embodiment, the dose is $1$-$10\times10^9$ CFU. In another embodiment, the dose is $2$-$10\times10^9$ CFU. In another embodiment, the dose is $3$-$10\times10^9$ CFU. In another embodiment, the dose is $2$-$7\times10^9$ CFU. In another embodiment, the dose is $2$-$5\times10^9$ CFU. In another embodiment, the dose is $3$-$5\times10^9$ CFU.

In another embodiment, the dose is $1\times10^7$ organisms. In another embodiment, the dose is $1\times10^8$ organisms. In another embodiment, the dose is $1\times10^9$ organisms. In another embodiment, the dose is $1.5\times10^9$ organisms. In another embodiment, the dose is $2\times10^9$ organisms. In another embodiment, the dose is $3\times10^9$ organisms. In another embodiment, the dose is $4\times10^9$ organisms. In another embodiment, the dose is $5\times10^9$ organisms. In another embodiment, the dose is $6\times10^9$ organisms. In another embodiment, the dose is $7\times10^9$ organisms. In another embodiment, the dose is $8\times10^9$ organisms. In another embodiment, the dose is $10\times10^9$ organisms. In another embodiment, the dose is $1.5\times10^{10}$ organisms. In another embodiment, the dose is $2\times10^{10}$ organisms. In another embodiment, the dose is $2.5\times10^{10}$ organisms. In another embodiment, the dose is $3\times10^{10}$ organisms. In another embodiment, the dose is $3.3\times10^{10}$ organisms. In another embodiment, the dose is $4\times10^{10}$ organisms. In another embodiment, the dose is $5\times10^{10}$ organisms. Each dose and range of doses represents a separate embodiment of the present invention.

In one embodiment, repeat administrations (doses) of compositions of this invention may be undertaken immediately following the first course of treatment or after an interval of days, weeks or months to achieve tumor regression. In another embodiment, repeat doses may be undertaken immediately following the first course of treatment or after an interval of days, weeks or months to achieve suppression of tumor growth. Assessment may be determined by any of the techniques known in the art, including diagnostic methods such as imaging techniques, analysis of serum tumor markers, biopsy, or the presence, absence or amelioration of tumor associated symptoms.

It will be appreciated by the skilled artisan that the term "Boosting" may encompass administering an immunogenic composition or recombinant *Listeria* strain dose to a subject. In another embodiment, of methods of the present invention, 2 boosts (or a total of 3 inoculations) are administered. In another embodiment, 3 boosts are administered. In another embodiment, 4 boosts are administered. In another embodiment, 5 boosts are administered. In another embodiment, 6 boosts are administered. In another embodiment, more than 6 boosts are administered. Each possibility represents a separate embodiment of the present invention.

In one embodiment, a method of present invention further comprises the step of boosting the human subject with a recombinant *Listeria* strain of the present invention. In another embodiment, the recombinant *Listeria* strain used in the booster inoculation is the same as the strain used in the initial "priming" inoculation. In another embodiment, the booster strain is different from the priming strain. In another embodiment, the same doses are used in the priming and boosting inoculations. In another embodiment, a larger dose is used in the booster. In another embodiment, a smaller dose is used in the booster. In another embodiment, the methods of the present invention further comprise the step of administering to the subject a booster vaccination. In one embodiment, the booster vaccination follows a single priming vaccination. In another embodiment, a single booster vaccination is administered after the priming vaccinations. In another embodiment, two booster vaccinations are administered after the priming vaccinations. In another embodiment, three booster vaccinations are administered after the priming vaccinations. In one embodiment, the period between a prime and a boost strain is experimentally determined by the skilled artisan. In another embodiment, the period between a prime and a boost strain is from 1 day and up to 1 week, in another embodiment it is up to 2 weeks, in another embodiment, it is up to 3 weeks, in another embodiment, it is up to 4 weeks, in another embodiment, it is up to 5 weeks, in another embodiment it is up to 6-8 weeks, in yet another embodiment, the boost strain is administered up to 8-12 weeks after the prime strain. Each possibility represents a separate embodiment of the present invention.

In another embodiment, a method of present invention further comprises the step of inoculating the human subject with an immunogenic composition comprising the E7 antigen. In another embodiment, the immunogenic composition comprises a recombinant E7 protein or fragment thereof. In another embodiment, the immunogenic composition comprises a nucleotide molecule expressing a recombinant E7 protein or fragment thereof. In another embodiment, the non-Listerial inoculation is administered after the Listerial inoculation. In another embodiment, the non-Listerial inoculation is administered before the Listerial inoculation. Each possibility represents a separate embodiment of the present invention.

The recombinant *Listeria* strain of methods and compositions of the present invention is, in another embodiment, a recombinant *Listeria monocytogenes* strain. In another embodiment, the *Listeria* strain is a recombinant *Listeria seeligeri* strain. In another embodiment, the *Listeria* strain is a recombinant *Listeria grayi* strain. In another embodiment, the *Listeria* strain is a recombinant *Listeria ivanovii* strain. In another embodiment, the *Listeria* strain is a recombinant *Listeria murrayi* strain. In another embodiment, the *Listeria* strain is a recombinant *Listeria welshimeri* strain. In another embodiment, the *Listeria* strain is a recombinant strain of any other *Listeria* species known in the art. Each possibility represents a separate embodiment of the present invention.

The present invention provides a number of Listerial species and strains for making or engineering an attenuated *Listeria* of the present invention. In one embodiment, the *Listeria* strain is *L. monocytogenes* 10403S wild type (see Bishop and Hinrichs (1987) J. Immunol. 139: 2005-2009; Lauer, et al. (2002) J. Bact. 184: 4177-4186.) In another embodiment, the *Listeria* strain is *L. monocytogenes* DP-L4056 (phage cured) (see Lauer, et al. (2002) J. Bact. 184: 4177-4186). In another embodiment, the *Listeria* strain is *L. monocytogenes* DP-L4027, which is phage cured and deleted in the hly gene (see Lauer, et al. (2002) J. Bact. 184: 4177-4186; Jones and Portnoy (1994) Infect. Immunity 65: 5608-5613.). In another embodiment, the *Listeria* strain is *L. monocytogenes* DP-L4029, which is phage cured, deleted in ActA (see Lauer, et al. (2002) J. Bact. 184: 4177-4186; Skoble, et al. (2000) J. Cell Biol. 150: 527-538). In another embodiment, the *Listeria* strain is *L. monocytogenes* DP-L4042 (delta PEST) (see Brockstedt, et al. (2004) Proc. Natl. Acad. Sci. USA 101: 13832-13837; supporting information). In another embodiment, the *Listeria* strain is *L. monocytogenes* DP-L4097 (LLO-44A) (see Brockstedt, et al. (2004) Proc. Natl. Acad. Sci. USA 101: 13832-13837; supporting information). In another embodiment, the *Listeria* strain is *L. monocytogenes* DP-L4364 (delta lplA; lipoate protein ligase) (see Brockstedt, et al. (2004) Proc. Natl. Acad. Sci. USA 101: 13832-13837; supporting information). In another embodiment, the *Listeria* strain is *L. monocytogenes* DP-L4405 (delta inlA) (see Brockstedt, et al. (2004) Proc. Natl. Acad. Sci. USA 101: 13832-13837; supporting information). In another embodiment, the *Listeria* strain is *L. monocytogenes* DP-L4406 (delta inlB) (see Brockstedt, et al. (2004) Proc. Natl. Acad. Sci. USA 101: 13832-13837; supporting information). In another embodiment, the *Listeria* strain is *L. monocytogenes* CS-L0001 (delta ActA-delta inlB) (see Brockstedt, et al. (2004) Proc. Natl. Acad. Sci. USA 101: 13832-13837; supporting information). In another embodiment, the *Listeria* strain is *L. monocytogenes* CS-L0002 (delta ActA-delta lplA) (see Brockstedt, et al. (2004) Proc. Natl. Acad. Sci. USA 101: 13832-13837; supporting information). In another embodiment, the *Listeria* strain is *L. monocytogenes* CS-L0003 (L461T-delta lplA) (see Brockstedt, et al. (2004) Proc. Natl. Acad. Sci. USA 101: 13832-13837; supporting information). In another embodiment, the *Listeria* strain is *L. monocytogenes* DP-L4038 (delta ActA-LLO L461T) (see Brockstedt, et al. (2004) Proc. Natl. Acad. Sci. USA 101: 13832-13837; supporting information). In another embodiment, the *Listeria* strain is *L. monocytogenes* DP-L4384 (S44A-LLO L461T) (see Brockstedt, et al. (2004) Proc. Natl. Acad. Sci.

USA 101: 13832-13837; supporting information). In another embodiment, the *Listeria* strain is *L. monocytogenes*. Mutation in lipoate protein (see O'Riordan, et al. (2003) Science 302: 462-464). In another embodiment, the *Listeria* strain is *L. monocytogenes* DP-L4017 (10403S hly (L461T), having a point mutation in hemolysin gene (see U.S. Provisional Pat. Appl. Ser. No. 60/490,089 filed Jul. 24, 2003). In another embodiment, the *Listeria* strain is *L. monocytogenes* EGD (see GenBank Acc. No. AL591824). In another embodiment, the *Listeria* strain is *L. monocytogenes* EGD-e (see GenB ank Acc. No. NC_003210. ATCC Acc. No. BAA-679). In another embodiment, the *Listeria* strain is *L. monocytogenes* DP-L4029 deleted in uvrAB (see U.S. Provisional Pat. Appl. Ser. No. 60/541,515 filed Feb. 2, 2004; U.S. Provisional Pat. Appl. Ser. No. 60/490,080 filed Jul. 24, 2003). In another embodiment, the *Listeria* strain is *L. monocytogenes* ActA-/inlB-double mutant (see ATCC Acc. No. PTA-5562). In another embodiment, the *Listeria* strain is *L. monocytogenes* lplA mutant or hly mutant (see U.S. Pat. Applic. No. 20040013690 of Portnoy, et. al). In another embodiment, the *Listeria* strain is *L. monocytogenes* DAL/DAT double mutant. (see U.S. Pat. Applic. No. 20050048081 of Frankel and Portnoy. The present invention encompasses reagents and methods that comprise the above Listerial strains, as well as these strains that are modified, e.g., by a plasmid and/or by genomic integration, to contain a nucleic acid encoding one of, or any combination of, the following genes: hly (LLO; listeriolysin); iap (p60); inlA; inlB; inlC; dal (alanine racemase); dat (D-amino acid aminotransferase); plcA; plcB; actA; or any nucleic acid that mediates growth, spread, breakdown of a single walled vesicle, breakdown of a double walled vesicle, binding to a host cell, uptake by a host cell. The present invention is not to be limited by the particular strains disclosed above.

In another embodiment, a recombinant *Listeria* strain of the present invention has been passaged through an animal host. In another embodiment, the passaging maximizes efficacy of the strain as a vaccine vector. In another embodiment, the passaging stabilizes the immunogenicity of the *Listeria* strain. In another embodiment, the passaging stabilizes the virulence of the *Listeria* strain. In another embodiment, the passaging increases the immunogenicity of the *Listeria* strain. In another embodiment, the passaging increases the virulence of the *Listeria* strain. In another embodiment, the passaging removes unstable sub-strains of the *Listeria* strain. In another embodiment, the passaging reduces the prevalence of unstable sub-strains of the *Listeria* strain. In another embodiment, the *Listeria* strain contains a genomic insertion of the gene encoding the antigen-containing recombinant peptide. In another embodiment, the *Listeria* strain carries a plasmid comprising the gene encoding the antigen-containing recombinant peptide. In another embodiment, the passaging is performed as described herein (e.g. in Example 12). In another embodiment, the passaging is performed by any other method known in the art. Each possibility represents a separate embodiment of the present invention.

In another embodiment, the recombinant *Listeria* strain utilized in methods of the present invention has been stored in a frozen cell bank. In another embodiment, the recombinant *Listeria* strain has been stored in a lyophilized condition. Each possibility represents a separate embodiment of the present invention.

In another embodiment, the cell bank of methods and compositions of the present invention is a master cell bank. In another embodiment, the cell bank is a working cell bank.

In another embodiment, the cell bank is Good Manufacturing Practice (GMP) cell bank. In another embodiment, the cell bank is intended for production of clinical-grade material. In another embodiment, the cell bank conforms to regulatory practices for human use. In another embodiment, the cell bank is any other type of cell bank known in the art. Each possibility represents a separate embodiment of the present invention.

"Good Manufacturing Practices" are defined, in another embodiment, by (21 CFR 210-211) of the United States Code of Federal Regulations. In another embodiment, "Good Manufacturing Practices" are defined by other standards for production of clinical-grade material or for human consumption; e.g. standards of a country other than the United States. Each possibility represents a separate embodiment of the present invention.

In another embodiment, a recombinant *Listeria* strain utilized in methods of the present invention is from a batch of vaccine doses.

In another embodiment, a recombinant *Listeria* strain utilized in methods of the present invention is from a frozen or lyophilized stock produced by methods provided in U.S. Pat. No. 8,114,414, which is incorporated by reference herein.

In another embodiment, a peptide of the present invention is a fusion peptide. In another embodiment, "fusion peptide" refers to a peptide or polypeptide comprising 2 or more proteins linked together by peptide bonds or other chemical bonds. In another embodiment, the proteins are linked together directly by a peptide or other chemical bond. In another embodiment, the proteins are linked together with 1 or more AA (e.g. a "spacer") between the 2 or more proteins. Each possibility represents a separate embodiment of the present invention.

In another embodiment, a vaccine of the present invention further comprises an adjuvant. The adjuvant utilized in methods and compositions of the present invention is, in another embodiment, a granulocyte/macrophage colony-stimulating factor (GM-CSF) protein. In another embodiment, the adjuvant comprises a GM-CSF protein. In another embodiment, the adjuvant is a nucleotide molecule encoding GM-CSF. In another embodiment, the adjuvant comprises a nucleotide molecule encoding GM-CSF. In another embodiment, the adjuvant is saponin QS21. In another embodiment, the adjuvant comprises saponin QS21. In another embodiment, the adjuvant is monophosphoryl lipid A. In another embodiment, the adjuvant comprises monophosphoryl lipid A. In another embodiment, the adjuvant is SBAS2. In another embodiment, the adjuvant comprises SBAS2. In another embodiment, the adjuvant is an unmethylated CpG-containing oligonucleotide. In another embodiment, the adjuvant comprises an unmethylated CpG-containing oligonucleotide. In another embodiment, the adjuvant is an immune-stimulating cytokine. In another embodiment, the adjuvant comprises an immune-stimulating cytokine. In another embodiment, the adjuvant is a nucleotide molecule encoding an immune-stimulating cytokine. In another embodiment, the adjuvant comprises a nucleotide molecule encoding an immune-stimulating cytokine. In another embodiment, the adjuvant is or comprises a quill glycoside. In another embodiment, the adjuvant is or comprises a bacterial mitogen. In another embodiment, the adjuvant is or comprises a bacterial toxin. In another embodiment, the adjuvant is or comprises any other adjuvant known in the art. Each possibility represents a separate embodiment of the present invention.

In another embodiment, a nucleotide of the present invention is operably linked to a promoter/regulatory sequence that drives expression of the encoded peptide in the *Listeria* strain. Promoter/regulatory sequences useful for driving constitutive expression of a gene are well known in the art and include, but are not limited to, for example, the $P_{hlyA}$, $P_{ActA}$, and p60 promoters of *Listeria*, the *Streptococcus* bac promoter, the *Streptomyces griseus* sgiA promoter, and the *B. thuringiensis* phaZ promoter. In another embodiment, inducible and tissue specific expression of the nucleic acid encoding a peptide of the present invention is accomplished by placing the nucleic acid encoding the peptide under the control of an inducible or tissue specific promoter/regulatory sequence. Examples of tissue specific or inducible promoter/regulatory sequences which are useful for his purpose include, but are not limited to the MMTV LTR inducible promoter, and the SV40 late enhancer/promoter. In another embodiment, a promoter that is induced in response to inducing agents such as metals, glucocorticoids, and the like, is utilized. Thus, it will be appreciated that the invention includes the use of any promoter/regulatory sequence, which is either known or unknown, and which is capable of driving expression of the desired protein operably linked thereto.

An N-terminal fragment of an ActA protein utilized in methods and compositions of the present invention has, in another embodiment, the sequence set forth in SEQ ID NO: 5. MRAMMVVFITANCITINPDIIFAATDSEDSSLNT-DEWEEEKTEEQPSEVNTGPRYETAR EVSSRDIKE-LEKSNKVRNTNKADLIAMLKEKAEKGPNINNNNSE-QTENAAINEEASG ADRPAIQVERRHPGLPSDSAAEIK-KRRKAIASSDSELESLTYPDKPTKVNKKKVAKES VADASESDLDSSMQSADESSPQPLKANQQPFFPK-VFKKIKDAGKWVRDKIDENPEVK KAIVDKSA-GLIDQLLTKKKSEEVNASDFPPPPTDEELRLALPETP-MLLGFNAPATSEPS SFEFPPPPTDEELRLALPET-PMLLGFNAPATSEPSSFEFPPPPTEDELEHRETASSLDS SF TRGDLASLRNAINRHSQNFSDFPPIPTEEELNGRG-GRP. In another embodiment, the ActA fragment comprises the sequence set forth in SEQ ID NO: 5. In another embodiment, the ActA fragment is any other ActA fragment known in the art. Each possibility represents a separate embodiment of the present invention.

In another embodiment, the recombinant nucleotide encoding a fragment of an ActA protein comprises the sequence set forth in SEQ ID NO: 6: Atgcgtgcgatgatggtg-gttttcattactgccaattgcattacgattaaccccgacataatatttgcagcgaca-gatagcgaagattcta gtctaaacacagatgaatgggaagaagaaaaaca-gaagagcaaccaagcgaggtaaatacgggaccaagatacgaaactgcacg tgaagtaagttcacgtgatattaaagaactagaaaaatcgaataaagt-gagaaatacgaacaaagcagacctaatagcaatgttgaaag aaaaagca-gaaaaaggtccaaatatcaataataacaacagtgaacaaactgagaatgcggc-tataaatgaagaggcttcaggagccg accgaccagctatacaagtggagc-gtcgtcatccaggattgccatcggatagcgcagcggaaattaaaaaaa-gaaggaaagccatag catcatcggatagtgagatgaaagccttacttatccgga-taaaccaacaaaagtaaataagaaaaaagtggcgaaagagtcagttgcg gat-gatctgaaagtgacttagattctagcatgcagtcagcagatgagtatcaccacaac-ctttaaaagcaaaccaacaaccattntccc taaagtatttaaaaaaataaaagatg-cggggaaatgggtacgtgataaaatcgacgaaaatcctgaagtaaagaaagc-gattgttgata aaagtgcagggttaattgaccaattattaaccaaaaagaaaagt-gaagaggtaaatgatcggacttcccgccaccacctacggatgaa gagt-taagacttgattgccagagacaccaatgatcttggttttaatgctcctgctacatcag-aaccgagctcattcgaatttccaccacca cctacggatgaagagttaagacttgat-tgccagagacgccaatgatcttggttttaatgctcctgctacatcggaac-cgagctcgttcga atttccaccgcctccaacagaagatgaactagaaatcatc-cggggaaacagcatcctcgctagattctagttttacaagagggatttagct agtttgagaaatgctattaatcgccatagtcaaaatttctctgatttcccaccaatcccaacagaagaagagttgaacgggagaggcggt agacca. In another embodiment, the recombinant nucleotide has the sequence set forth in SEQ ID NO: 6. In another embodiment, the recombinant nucleotide comprises any other sequence that encodes a fragment of an ActA protein. Each possibility represents a separate embodiment of the present invention.

In another embodiment of the methods and compositions of the present invention, a PEST amino acid AA sequence is fused to the E7 or E6 antigen. As provided herein, recombinant *Listeria* strains expressing PEST amino acid sequence-antigen fusions induce anti-tumor immunity (Example 3) and generate antigen-specific, tumor-infiltrating T cells (Example 4). Further, enhanced cell mediated immunity was demonstrated for fusion proteins comprising an antigen and LLO containing the PEST amino acid AA sequence KENSISSMAPPASPPASPKTPIEKKHADEIDK (SEQ ID NO: 1).

Thus, fusion of an antigen to other LM PEST amino acid sequences and PEST amino acid sequences derived from other prokaryotic organisms will also enhance immunogenicity of the antigen. The PEST amino acid AA sequence has, in another embodiment, a sequence selected from SEQ ID NO: 7-12. In another embodiment, the PEST amino acid sequence is a PEST amino acid sequence from the LM ActA protein. In another embodiment, the PEST amino acid sequence is KTEEQPSEVNTGPR (SEQ ID NO: 7), KAS-VTDTSEGDLDSSMQSADESTPQPLK (SEQ ID NO: 8), KNEEVNASDFPPPPTDEELR (SEQ ID NO: 9), or RGGIPTSEEFSSLNSGDFTDDENSETTEEEIDR (SEQ ID NO: 10). In another embodiment, the PEST amino acid sequence is from Streptolysin 0 protein of *Streptococcus* sp. In another embodiment, the PEST amino acid sequence is from *Streptococcus pyogenes* Streptolysin 0, e.g. KQN-TASTETTTTNEQPK (SEQ ID NO: 11) at AA 35-51. In another embodiment, the PEST amino acid sequence is from *Streptococcus equisimilis* Streptolysin 0, e.g. KQNTAN-TETTTTNEQPK (SEQ ID NO: 12) at AA 38-54. In another embodiment, the PEST amino acid sequence is another PEST amino acid AA sequence derived from a prokaryotic organism. In another embodiment, the PEST amino acid sequence is any other PEST amino acid sequence known in the art. Each possibility represents a separate embodiment of the present invention.

PEST amino acid sequences of other prokaryotic organism can be identified in accordance with methods such as described by, for example Rechsteiner and Rogers (1996, Trends Biochem. Sci. 21:267-271) for LM. Alternatively, PEST amino acid AA sequences from other prokaryotic organisms can also be identified based by this method. Other prokaryotic organisms wherein PEST amino acid AA sequences would be expected to include, but are not limited to, other *Listeria* species. In another embodiment, the PEST amino acid sequence is embedded within the antigenic protein. Thus, in another embodiment, "fusion" refers to an antigenic protein comprising both the antigen and either i) an N-terminal LLO protein (tLLO), ii) an N-terminal ActA protein or iii) a PEST amino acid sequence either linked at one end of the antigen or embedded within the antigen.

In another embodiment, a PEST amino acid sequence is identified using any other method or algorithm known in the art, e.g the CaSPredictor (Garay-Malpartida H M, Occhiucci J M, Alves J, Belizario J E. Bioinformatics. 2005 June; 21 Suppl 1:i169-76). In another embodiment, the following method is used:

A PEST index is calculated for each 30-35 AA stretch by assigning a value of 1 to the amino acids Ser, Thr, Pro, Glu, Asp, Asn, or Gln. The coefficient value (CV) for each of the PEST residue is 1 and for each of the other AA (non-PEST) is 0.

Each method for identifying a PEST amino acid sequence represents a separate embodiment of the present invention.

In another embodiment, the LLO protein, ActA protein, or fragment thereof of the present invention need not be that which is set forth exactly in the sequences set forth herein, but rather other alterations, modifications, or changes can be made that retain the functional characteristics of an LLO or ActA protein fused to an antigen as set forth elsewhere herein. In another embodiment, the present invention utilizes an analog of an LLO protein, ActA protein, or fragment thereof. Analogs differ, in another embodiment, from naturally occurring proteins or peptides by conservative AA sequence differences or by modifications which do not affect sequence, or by both.

In another embodiment, either a whole E7 protein or a fragment thereof is fused to a LLO protein, ActA protein, or PEST amino acid sequence-containing peptide to generate a recombinant peptide of methods of the present invention. The E7 protein that is utilized (either whole or as the source of the fragments) has, in another embodiment, the sequence MHGDTPTLHEYMLDLQPETTDLYCYEQLNDSSEEE-DEIDGPAGQAEPDRAHY NIVTFCCKCDSTLRL-CVQSTHVDIRTLEDLLMGTLGIVCPICSQKP (SEQ ID No: 13). In another embodiment, the E7 protein is a homologue of SEQ ID No: 13. In another embodiment, the E7 protein is a variant of SEQ ID No: 13. In another embodiment, the E7 protein is an isomer of SEQ ID No: 13. In another embodiment, the E7 protein is a fragment of SEQ ID No: 13. In another embodiment, the E7 protein is a fragment of a homologue of SEQ ID No: 13. In another embodiment, the E7 protein is a fragment of a variant of SEQ ID No: 13. In another embodiment, the E7 protein is a fragment of an isomer of SEQ ID No: 13. Each possibility represents a separate embodiment of the present invention.

In another embodiment, the sequence of the E7 protein is: MHGPKATLQDIVLHLEPQNEIPVDLLCHEQLSD-SEEENDEIDGVNHQHLPARR AEPQRHTMLCMCCK-CEARIELVVESSADDLRAFQQLFLNTLSFVCPW-CASQQ (SEQ ID No: 14). In another embodiment, the E6 protein is a homologue of SEQ ID No: 14. In another embodiment, the E6 protein is a variant of SEQ ID No: 14. In another embodiment, the E6 protein is an isomer of SEQ ID No: 14. In another embodiment, the E6 protein is a fragment of SEQ ID No: 14. In another embodiment, the E6 protein is a fragment of a homologue of SEQ ID No: 14. In another embodiment, the E6 protein is a fragment of a variant of SEQ ID No: 14. In another embodiment, the E6 protein is a fragment of an isomer of SEQ ID No: 14. Each possibility represents a separate embodiment of the present invention.

In another embodiment, the E7 protein has a sequence set forth in one of the following GenBank entries: M24215, NC_004500, V01116, X62843, or M14119. In another embodiment, the E7 protein is a homologue of a sequence from one of the above GenBank entries. In another embodiment, the E7 protein is a variant of a sequence from one of the above GenBank entries. In another embodiment, the E7 protein is an isomer of a sequence from one of the above GenBank entries. In another embodiment, the E7 protein is a fragment of a sequence from one of the above GenBank entries. In another embodiment, the E7 protein is a fragment of a homologue of a sequence from one of the above GenBank entries. In another embodiment, the E7 protein is a fragment of a variant of a sequence from one of the above GenBank entries. In another embodiment, the E7 protein is a fragment of an isomer of a sequence from one of the above GenBank entries. Each possibility represents a separate embodiment of the present invention.

In another embodiment, either a whole E6 protein or a fragment thereof is fused to a LLO protein, ActA protein, or PEST amino acid sequence-containing peptide to generate a recombinant peptide of methods of the present invention. The E6 protein that is utilized (either whole or as the source of the fragments) has, in another embodiment, the sequence MHQKRTAMFQDPQERPRKLPQLCTELQTTIHDII-LECVYCKQQLLRREVYDFA FRDLCIVYRDGN-PYAVCDKCLKFYSKISEYRHYCYSLYGTTLEQQYNK-PLCDLLIRCI NCQKPLCPEEKQRHLDKKQRFHNIRG-RWTGRCMSCCRSSRTRRETQL (SEQ ID No: 15). In another embodiment, the E6 protein is a homologue of SEQ ID No: 15. In another embodiment, the E6 protein is a variant of SEQ ID No: 15. In another embodiment, the E6 protein is an isomer of SEQ ID No: 15. In another embodiment, the E6 protein is a fragment of SEQ ID No: 15. In another embodiment, the E6 protein is a fragment of a homologue of SEQ ID No: 15. In another embodiment, the E6 protein is a fragment of a variant of SEQ ID No: 15. In another embodiment, the E6 protein is a fragment of an isomer of SEQ ID No: 15. Each possibility represents a separate embodiment of the present invention.

In another embodiment, the sequence of the E6 protein is: MARFEDPTRRPYKLPDLCTELNTSLQDIEITCVY-CKTVLELTEVFEFAFKDLFV VYRDSIPHAACHKCID-FYSRIRELRHYSDSVYGDTLEKLTNTGLYNLLIRCL-RCQKPL NPAEKLRHLNEKRRFHNIAGHYRGQCH-SCCNRARQERLQRRRETQV (SEQ ID No: 16). In another embodiment, the E6 protein is a homologue of SEQ ID No: 16. In another embodiment, the E6 protein is a variant of SEQ ID No: 16. In another embodiment, the E6 protein is an isomer of SEQ ID No: 16. In another embodiment, the E6 protein is a fragment of SEQ ID No: 16. In another embodiment, the E6 protein is a fragment of a homologue of SEQ ID No: 16. In another embodiment, the E6 protein is a fragment of a variant of SEQ ID No: 16. In another embodiment, the E6 protein is a fragment of an isomer of SEQ ID No: 16. Each possibility represents a separate embodiment of the present invention.

In another embodiment, the E6 protein has a sequence set forth in one of the following GenBank entries: M24215, M14119, NC_004500, V01116, X62843, or M14119. In another embodiment, the E6 protein is a homologue of a sequence from one of the above GenBank entries. In another embodiment, the E6 protein is a variant of a sequence from one of the above GenBank entries. In another embodiment, the E6 protein is an isomer of a sequence from one of the above GenBank entries. In another embodiment, the E6 protein is a fragment of a sequence from one of the above GenBank entries. In another embodiment, the E6 protein is a fragment of a homologue of a sequence from one of the above GenBank entries. In another embodiment, the E6 protein is a fragment of a variant of a sequence from one of the above GenBank entries. In another embodiment, the E6 protein is a fragment of an isomer of a sequence from one of the above GenBank entries. Each possibility represents a separate embodiment of the present invention.

In another embodiment, "homology" refers to identity to an LLO sequence (e.g. to one of SEQ ID No: 2-4) of greater than 60%. In another embodiment, "homology" refers to identity to one of SEQ ID No: 2-4 of greater than 64%. In another embodiment, "homology" refers to identity to one of SEQ ID No: 2-4 of greater than 68%. In another embodiment, "homology" refers to identity to one of SEQ ID No: 2-4 of greater than 72%. In another embodiment, "homology" refers to identity to one of SEQ ID No: 2-4 of greater than 75%. In another embodiment, "homology" refers to identity to one of SEQ ID No: 2-4 of greater than 78%. In another embodiment, "homology" refers to identity to one of SEQ ID No: 2-4 of greater than 80%. In another embodiment, "homology" refers to identity to one of SEQ ID No: 2-4 of greater than 82%. In another embodiment, "homology" refers to identity to one of SEQ ID No: 2-4 of greater than 83%. In another embodiment, "homology" refers to identity to one of SEQ ID No: 2-4 of greater than 85%. In another embodiment, "homology" refers to identity to one of SEQ ID No: 2-4 of greater than 87%. In another embodiment, "homology" refers to identity to one of SEQ ID No: 2-4 of greater than 88%. In another embodiment, "homology" refers to identity to one of SEQ ID No: 2-4 of greater than 90%. In another embodiment, "homology" refers to identity to one of SEQ ID No: 2-4 of greater than 92%. In another embodiment, "homology" refers to identity to one of SEQ ID No: 2-4 of greater than 93%. In another embodiment, "homology" refers to identity to one of SEQ ID No: 2-4 of greater than 95%. In another embodiment, "homology" refers to identity to one of SEQ ID No: 2-4 of greater than 96%. In another embodiment, "homology" refers to identity to one of SEQ ID No: 2-4 of greater than 97%. In another embodiment, "homology" refers to identity to one of SEQ ID No: 2-4 of greater than 98%. In another embodiment, "homology" refers to identity to one of SEQ ID No: 2-4 of greater than 99%. In another embodiment, "homology" refers to identity to one of SEQ ID No: 2-4 of 100%. Each possibility represents a separate embodiment of the present invention.

In another embodiment, "homology" refers to identity to an E7 sequence (e.g. to one of SEQ ID No: 13-14) of greater than 60%. In another embodiment, "homology" refers to identity to one of SEQ ID No: 13-14 of greater than 62%. In another embodiment, "homology" refers to identity to one of SEQ ID No: 13-14 of greater than 64%. In another embodiment, "homology" refers to identity to one of SEQ ID No: 13-14 of greater than 68%. In another embodiment, "homology" refers to identity to one of SEQ ID No: 13-14 of greater than 72%. In another embodiment, "homology" refers to identity to one of SEQ ID No: 13-14 of greater than 75%. In another embodiment, "homology" refers to identity to one of SEQ ID No: 13-14 of greater than 78%. In another embodiment, "homology" refers to identity to one of SEQ ID No: 13-14 of greater than 80%. In another embodiment, "homology" refers to identity to one of SEQ ID No: 13-14 of greater than 82%. In another embodiment, "homology" refers to identity to one of SEQ ID No: 13-14 of greater than 83%. In another embodiment, "homology" refers to identity to one of SEQ ID No: 13-14 of greater than 85%. In another embodiment, "homology" refers to identity to one of SEQ ID No: 13-14 of greater than 87%. In another embodiment, "homology" refers to identity to one of SEQ ID No: 13-14 of greater than 88%. In another embodiment, "homology" refers to identity to one of SEQ ID No: 13-14 of greater than 90%. In another embodiment, "homology" refers to identity to one of SEQ ID No: 13-14 of greater than 92%. In another embodiment, "homology" refers to identity to one of SEQ ID No: 13-14 of greater than 93%. In another embodiment, "homology" refers to identity to one of SEQ ID No: 13-14 of greater than 95%. In another embodiment, "homology" refers to identity to one of SEQ ID No: 13-14 of greater than 96%. In another embodiment, "homology" refers to identity to one of SEQ ID No: 13-14 of greater than 97%. In another embodiment, "homology" refers to identity to one of SEQ ID No: 13-14 of greater than 98%. In another embodiment, "homology" refers to identity to one of SEQ ID No: 13-14 of greater than 99%. In another embodiment, "homology" refers to identity to one of SEQ ID No: 13-14 of 100%. Each possibility represents a separate embodiment of the present invention.

In another embodiment, "homology" refers to identity to an E6 sequence (e.g. to one of SEQ ID No: 15-16) of greater than 60%. In another embodiment, "homology" refers to identity to one of SEQ ID No: 15-16 of greater than 64%. In another embodiment, "homology" refers to identity to one of SEQ ID No: 15-16 of greater than 68%. In another embodiment, "homology" refers to identity to one of SEQ ID No: 15-16 of greater than 72%. In another embodiment, "homology" refers to identity to one of SEQ ID No: 15-16 of greater than 75%. In another embodiment, "homology" refers to identity to one of SEQ ID No: 15-16 of greater than 78%. In another embodiment, "homology" refers to identity to one of SEQ ID No: 15-16 of greater than 80%. In another embodiment, "homology" refers to identity to one of SEQ ID No: 15-16 of greater than 82%. In another embodiment, "homology" refers to identity to one of SEQ ID No: 15-16 of greater than 83%. In another embodiment, "homology" refers to identity to one of SEQ ID No: 15-16 of greater than 85%. In another embodiment, "homology" refers to identity to one of SEQ ID No: 15-16 of greater than 87%. In another embodiment, "homology" refers to identity to one of SEQ ID No: 15-16 of greater than 88%. In another embodiment, "homology" refers to identity to one of SEQ ID No: 15-16 of greater than 90%. In another embodiment, "homology" refers to identity to one of SEQ ID No: 15-16 of greater than 92%. In another embodiment, "homology" refers to identity to one of SEQ ID No: 15-16 of greater than 93%. In another embodiment, "homology" refers to identity to one of SEQ ID No: 15-16 of greater than 95%. In another embodiment, "homology" refers to identity to one of SEQ ID No: 15-16 of greater than 96%. In another embodiment, "homology" refers to identity to one of SEQ ID No: 15-16 of greater than 97%.

In another embodiment, "homology" refers to identity to one of SEQ ID No: 15-16 of greater than 98%. In another embodiment, "homology" refers to identity to one of SEQ ID No: 15-16 of greater than 99%. In another embodiment, "homology" refers to identity to one of SEQ ID No: 15-16 of 100%. Each possibility represents a separate embodiment of the present invention.

In another embodiment, "homology" refers to identity to a PEST amino acid sequence (e.g. to one of SEQ ID No: 1, and 7-12) or to an ActA sequence (e.g. to one of SEQ ID No: 5-6) of greater than 60%. In another embodiment, "homology" refers to identity to one of SEQ ID No: 1, and 7-12 or SEQ ID No: 5-6 of greater than 60%. In another embodiment, "homology" refers to identity to one of SEQ ID No: 1, and 7-12 or SEQ ID No: 5-6 of greater than 64%. In another embodiment, "homology" refers to identity to one of SEQ ID No: 1, and 7-12 or SEQ ID No: 5-6 of greater than 68%. In another embodiment, "homology" refers to identity to one of SEQ ID No: 1, and 7-12 or SEQ ID No: 5-6 of greater than 72%. In another embodiment, "homology" refers to identity to one of SEQ ID No: 1, and 7-12 or SEQ ID No: 5-6 of greater than 75%. In another embodiment, "homology" refers to identity to one of SEQ ID No: 1, and 7-12 or SEQ ID No: 5-6 of greater than 78%. In another embodiment, "homology" refers to identity to one of SEQ ID No: 1, and 7-12 or SEQ ID No: 5-6 of greater than 80%.

In another embodiment, "homology" refers to identity to one of SEQ ID No: 1, and 7-12 or SEQ ID No: 5-6 of greater than 82%. In another embodiment, "homology" refers to identity to one of SEQ ID No: 1, and 7-12 or SEQ ID No: 5-6 of greater than 83%. In another embodiment, "homology" refers to identity to one of SEQ ID No: 1, and 7-12 or SEQ ID No: 5-6 of greater than 85%. In another embodiment, "homology" refers to identity to one of SEQ ID No: 1, and 7-12 or SEQ ID No: 5-6 of greater than 87%. In another embodiment, "homology" refers to identity to one of SEQ ID No: 1, and 7-12 or SEQ ID No: 5-6 of greater than 88%. In another embodiment, "homology" refers to identity to one of SEQ ID No: 1, and 7-12 or SEQ ID No: 5-6 of greater than 90%. In another embodiment, "homology" refers to identity to one of SEQ ID No: 1, and 7-12 or SEQ ID No: 5-6 of greater than 92%. In another embodiment, "homology" refers to identity to one of SEQ ID No: 1, and 7-12 or SEQ ID No: 5-6 of greater than 93%. In another embodiment, "homology" refers to identity to one of SEQ ID No: 1, and 7-12 or SEQ ID No: 5-6 of greater than 95%. In another embodiment, "homology" refers to identity to one of SEQ ID No: 1, and 7-12 or SEQ ID No: 5-6 of greater than 96%. In another embodiment, "homology" refers to identity to one of SEQ ID No: 1, and 7-12 or SEQ ID No: 5-6 of greater than 97%. In another embodiment, "homology" refers to identity to one of SEQ ID No: 1, and 7-12 or SEQ ID No: 5-6 of greater than 98%. In another embodiment, "homology" refers to identity to one of SEQ ID No: 1, and 7-12 or SEQ ID No: 5-6 of greater than 99%. In another embodiment, "homology" refers to identity to one of SEQ ID No: 1, and 7-12 or SEQ ID No: 5-6 of 100%. Each possibility represents a separate embodiment of the present invention.

Protein and/or peptide homology for any AA sequence listed herein is determined, in one embodiment, by methods well described in the art, including immunoblot analysis, or via computer algorithm analysis of AA sequences, utilizing any of a number of software packages available, via established methods. Some of these packages include the FASTA, BLAST, MPsrch or Scanps packages, and employ, in other embodiments, the use of the Smith and Waterman algorithms, and/or global/local or BLOCKS alignments for analysis, for example. Each method of determining homology represents a separate embodiment of the present invention.

In another embodiment, the LLO protein, ActA protein, or fragment thereof is attached to the antigen by chemical conjugation. In another embodiment, glutaraldehyde is used for the conjugation. In another embodiment, the conjugation is performed using any suitable method known in the art. Each possibility represents another embodiment of the present invention.

In another embodiment, fusion proteins of the present invention are prepared by any suitable method, including, for example, cloning and restriction of appropriate sequences or direct chemical synthesis by methods discussed below. In another embodiment, subsequences are cloned and the appropriate subsequences cleaved using appropriate restriction enzymes. The fragments are then ligated, in another embodiment, to produce the desired DNA sequence. In another embodiment, DNA encoding the fusion protein is produced using DNA amplification methods, for example polymerase chain reaction (PCR). First, the segments of the native DNA on either side of the new terminus are amplified separately. The 5 end of the one amplified sequence encodes the peptide linker, while the 3' end of the other amplified sequence also encodes the peptide linker. Since the 5' end of the first fragment is complementary to the 3' end of the second fragment, the two fragments (after partial purification, e.g. on LMP agarose) can be used as an overlapping template in a third PCR reaction. The amplified sequence will contain codons, the segment on the carboxy side of the opening site (now forming the amino sequence), the linker, and the sequence on the amino side of the opening site (now forming the carboxyl sequence). The insert is then ligated into a plasmid.

In another embodiment, the LLO protein, ActA protein, or fragment thereof and the antigen, or fragment thereof are conjugated by a means known to those of skill in the art. In another embodiment, the antigen, or fragment thereof is conjugated, either directly or through a linker (spacer), to the ActA protein or LLO protein. In another embodiment, the chimeric molecule is recombinantly expressed as a single-chain fusion protein.

In another embodiment, a fusion peptide of the present invention is synthesized using standard chemical peptide synthesis techniques. In another embodiment, the chimeric molecule is synthesized as a single contiguous polypeptide. In another embodiment, the LLO protein, ActA protein, or fragment thereof; and the antigen, or fragment thereof are synthesized separately, then fused by condensation of the amino terminus of one molecule with the carboxyl terminus of the other molecule, thereby forming a peptide bond. In another embodiment, the ActA protein or LLO protein and antigen are each condensed with one end of a peptide spacer molecule, thereby forming a contiguous fusion protein.

In another embodiment, the peptides and proteins of the present invention are prepared by solid-phase peptide synthesis (SPPS) as described by Stewart et al. in Solid Phase Peptide Synthesis, 2nd Edition, 1984, Pierce Chemical Company, Rockford, Ill.; or as described by Bodanszky and Bodanszky (The Practice of Peptide Synthesis, 1984, Springer-Verlag, New York). In another embodiment, a suitably protected AA residue is attached through its carboxyl group to a derivatized, insoluble polymeric support, such as cross-linked polystyrene or polyamide resin. "Suitably protected" refers to the presence of protecting groups on both the alpha-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial AA, and couple thereto of the carboxyl end of the next AA in the sequence of the desired peptide. This AA is also suitably protected. The carboxyl of the incoming AA can be activated to react with the N-terminus of the support-bound AA by formation into a reactive group such as formation into a carbodiimide, a symmetric acid anhydride or an "active ester" group such as hydroxybenzotriazole or pentafluorophenly esters. The pharmaceutical compositions containing vaccines and compositions of the present invention are, in another embodiment, administered to a subject by any method known to a person skilled in the art, such as parenterally, paracancerally, transmucosally, transdermally, intramuscularly, intravenously, intra-dermally, subcutaneously, intra-peritonealy, intra-ventricularly, intra-cranially, intra-vaginally or intra-tumorally.

In another embodiment of the methods and compositions provided herein, the vaccines or compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In another embodiment of the present invention, the active ingredient is formulated in a capsule. In accordance with this embodiment, the compositions of the present invention comprise, in addition to the active compound and the inert carrier or diluent, a hard gelating capsule.

In another embodiment, the vaccines or compositions are administered by intravenous, intra-arterial, or intra-muscular injection of a liquid preparation. Suitable liquid formulations include solutions, suspensions, dispersions, emulsions, oils and the like. In one embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intra-muscularly and are thus formulated in a form suitable for intra-muscular administration.

It will be appreciated by a skilled artisan that the term "treating" may encompass both therapeutic treatment and prophylactic or preventative measures, wherein the object is to prevent or lessen the targeted pathologic condition or disorder as described herein. Thus, in one embodiment, treating may include directly affecting or curing, suppressing, inhibiting, preventing, reducing the severity of, delaying the onset of, reducing symptoms associated with the disease, disorder or condition, or a combination thereof. Thus, in one embodiment, "treating" may encompass inter alia delaying progression, expediting remission, inducing remission, augmenting remission, speeding recovery, increasing efficacy of or decreasing resistance to alternative therapeutics, or a combination thereof. In one embodiment, "preventing" or "impeding" may encompass, inter alia, delaying the onset of symptoms, preventing relapse to a disease, decreasing the number or frequency of relapse episodes, increasing latency between symptomatic episodes, or a combination thereof. In one embodiment, "suppressing" or "inhibiting", may encompass, inter alia, reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

In one embodiment, symptoms are primary, while in another embodiment, symptoms are secondary. In one embodiment, "primary" refers to a symptom that is a direct result of a particular disease or disorder, while in one embodiment, "secondary" refers to a symptom that is derived from or consequent to a primary cause. In one embodiment, the compounds for use in the present invention treat primary or secondary symptoms or secondary complications. In another embodiment, "symptoms" may be any manifestation of a disease or pathological condition.

In another embodiment, the present invention provides a kit comprising vaccine of the present invention, an applicator, and instructional material that describes use of the methods of the invention. Although model kits are described below, the contents of other useful kits will be apparent to the skilled artisan in light of the present disclosure. Each of these kits represents a separate embodiment of the present invention.

In one embodiment, the singular forms of words such as "a," "an," and "the," include their corresponding plural references unless the context clearly dictates otherwise.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub ranges as well as individual numerical values within that range. For example, description of a range such as from 1 to 6 should be considered to have specifically disclosed sub ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

It will be appreciated by a skilled artisan that the term "about" when used to modify a numerically defined parameter may encompass variation of the parameter in quantitative terms plus or minus 5%, or in another embodiment plus or minus 10%, or in another embodiment plus or minus 15%, or in another embodiment plus or minus 20% of stated numerical value for that parameter.

It is to be understood by the skilled artisan that the term "subject" can encompass a mammal including an adult human or a human child, teenager or adolescent in need of therapy for, or susceptible to, a condition or its sequelae, and also may include non-human mammals such as dogs, cats, pigs, cows, sheep, goats, horses, rats, and mice. It will also be appreciated that the term may encompass livestock. The term "subject" does not exclude an individual that is normal in all respects.

It will be appreciated by the skilled artisan that the term "mammal" for purposes of treatment refers to any animal classified as a mammal, including, but not limited to, humans, domestic and farm animals, and zoo, sports, or pet animals, such as canines, including dogs, and horses, cats, cattle, pigs, sheep, etc.

In the following examples, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention. Thus these examples should in no way be construed, as limiting the broad scope of the invention.

EXPERIMENTAL DETAILS SECTION

Example 1: LLO-Antigen Fusions Induce Anti-Tumor Immunity

Materials and Experimental Methods (Examples 1-2)

Cell Lines

The C57BL/6 syngeneic TC-1 tumor was immortalized with HPV-16 E6 and E7 and transformed with the c-Ha-ras oncogene. TC-1, provided by T. C. Wu (Johns Hopkins University School of Medicine, Baltimore, Md.) is a highly tumorigenic lung epithelial cell expressing low levels of with HPV-16 E6 and E7 and transformed with the c-Ha-ras oncogene. TC-1 was grown in RPMI 1640, 10% FCS, 2 mM L-glutamine, 100 U/ml penicillin, 100 μg/ml streptomycin, 100 μM nonessential amino acids, 1 mM sodium pyruvate, 50 micromolar (mcM) 2-ME, 400 microgram (mcg)/ml G418, and 10% National Collection Type Culture-109 medium at 37° with 10% $CO_2$. C3 is a mouse embryo cell from C57BL/6 mice immortalized with the complete genome of HPV 16 and transformed with pEJ-ras. EL-4/E7 is the thymoma EL-4 retrovirally transduced with E7.

*L. monocytogenes* Strains and Propagation

Figure 2:
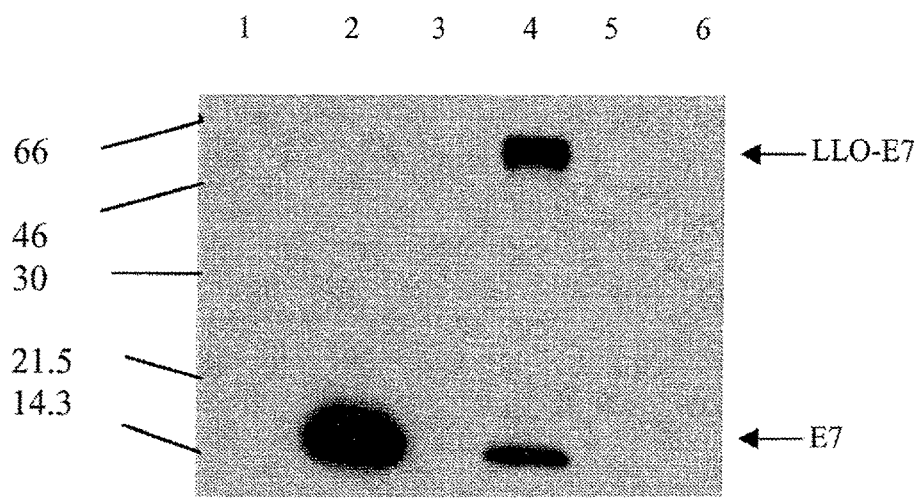
FIG. 2. Lm-E7 and Lm-LLO-E7 secrete E7. Lm-Gag (lane 1), Lm-E7 (lane 2), Lm-LLO-NP (lane 3), Lm-LLO-E7 (lane 4), XFL-7 (lane 5), and 10403S (lane 6) were grown overnight at 37° C. in Luria-Bertoni broth. Equivalent numbers of bacteria, as determined by OD at 600 nm absorbance, were pelleted and 18 ml of each supernatant was TCA precipitated. E7 expression was analyzed by Western blot. The blot was probed with an anti-E7 mAb, followed by HRP-conjugated anti-mouse (Amersham), then developed using ECL detection reagents.

*Listeria* strains used were Lm-LLO-E7 (hly-E7 fusion gene in an episomal expression system; FIG. 1A), Lm-E7 (single-copy E7 gene cassette integrated into *Listeria* genome), Lm-LLO-NP ("DP-L2028"; hly-NP fusion gene in an episomal expression system), and Lm-Gag ("ZY-18"; single-copy HIV-1 Gag gene cassette integrated into the chromosome). E7 was amplified by PCR using the primers 5'-GGCTCGAGCATGGAGATACACC-3 (SEQ ID No: 17; XhoI site is underlined) and 5'-GGGGACTAGTTTATGGTTTCTGAGAACA-3' (SEQ ID No: 18; SpeI site is underlined) and ligated into pCR2.1 (Invitrogen, San Diego, Calif.). E7 was excised from pCR2.1 by XhoI/SpeI digestion and ligated into pGG-55. The hly-E7 fusion gene and the pluripotential transcription factor prfA were cloned into pAM401, a multicopy shuttle plasmid (Wirth R et al, J Bacteriol, 165: 831, 1986), generating pGG-55. The hly promoter drives the expression of the first 441 AA of the hly gene product, (lacking the hemolytic C-terminus, referred to below as "ΔLLO," and having the sequence set forth in SEQ ID No: 25), which is joined by the XhoI site to the E7 gene, yielding a hly-E7 fusion gene that is transcribed and secreted as LLO-E7. Transformation of a prfA negative strain of *Listeria*, XFL-7 (provided by Dr. Hao Shen, University of Pennsylvania), with pGG-55 selected for the retention of the plasmid in vivo (FIGS. 1A-B). The hly promoter and gene fragment were generated using primers 5'-GGGGGCTAGCCCTCCTTTGATTAGTATATTC-3 (SEQ ID No: 19; NheI site is underlined) and 5'-CTCCCTCGAGATCATAATTTACTTCATC-3' (SEQ ID No: 20; Xhof site is underlined). The prfA gene was PCR amplified using primers 5'-GACTACAAGGACGATGAC-CGACAAGTGATAACCCGGGATCTAAATAAATC-CGTTT-3' (SEQ ID No: 27; XbaI site is underlined) and 5'-CCCGTCGACCAGCTCTTCTTGGTGAAG-3' (SEQ ID No: 21; SalI site is underlined). Lm-E7 was generated by introducing an expression cassette containing the hly promoter and signal sequence driving the expression and secretion of E7 into the orfZ domain of the LM genome. E7 was amplified by PCR using the primers 5'-GCGGATCCCATGGAGATACACCTAC-3' (SEQ ID No: 22; BamHI site is underlined) and 5'-GCTCTAGATTATGGTTTCTGAG-3' (SEQ ID No: 23; XbaI site is underlined). E7 was then ligated into the pZY-21 shuttle vector. LM strain 10403S was transformed with the resulting plasmid, pZY-21-E7, which includes an expression cassette inserted in the middle of a 1.6-kb sequence that corresponds to the orfX, Y, Z domain of the LM genome. The homology domain allows for insertion of the E7 gene cassette into the orfZ domain by homologous recombination. Clones were screened for integration of the E7 gene cassette into the orfZ domain. Bacteria were grown in brain heart infusion medium with (Lm-LLO-E7 and Lm-LLO-NP) or without (Lm-E7 and ZY-18) chloramphenicol (20 μg/ml). Bacteria were frozen in aliquots at −80° C. Expression was verified by Western blotting (FIG. 2).

Western Blotting

*Listeria* strains were grown in Luria-Bertoni medium at 37° C. and were harvested at the same optical density measured at 600 nm. The supernatants were TCA precipitated and resuspended in 1× sample buffer supplemented with 0.1 N NaOH. Identical amounts of each cell pellet or each TCA-precipitated supernatant were loaded on 4-20% Tris-glycine SDS-PAGE gels (NOVEX, San Diego, Calif.). The gels were transferred to polyvinylidene difluoride and probed with an anti-E7 monoclonal antibody (mAb) (Zymed Laboratories, South San Francisco, Calif.), then incubated with HRP-conjugated anti-mouse secondary Ab (Amersham Pharmacia Biotech, Little Chalfont, U.K.), developed with Amersham ECL detection reagents, and exposed to Hyperfilm (Amersham Pharmacia Biotech).

Measurement of Tumor Growth

Tumors were measured every other day with calipers spanning the shortest and longest surface diameters. The mean of these two measurements was plotted as the mean tumor diameter in millimeters against various time points. Mice were sacrificed when the tumor diameter reached 20 mm Tumor measurements for each time point are shown only for surviving mice.

Effects of *Listeria* Recombinants on Established Tumor Growth

Six- to 8-wk-old C57BL/6 mice (Charles River) received $2 \times 10^5$ TC-1 cells s.c. on the left flank. One week following tumor inoculation, the tumors had reached a palpable size of 4-5 mm in diameter. Groups of eight mice were then treated with 0.1 $LD_{50}$ i.p. Lm-LLO-E7 ($10^7$ CFU), Lm-E7 ($10^6$ CFU), Lm-LLO-NP ($10^7$ CFU), or Lm-Gag ($5 \times 10^5$ CFU) on days 7 and 14.

$^{51}$Cr Release Assay

C57BL/6 mice, 6-8 wk old, were immunized i.p. with 0.1$LD_{50}$ Lm-LLO-E7, Lm-E7, Lm-LLO-NP, or Lm-Gag. Ten days post-immunization, spleens were harvested. Splenocytes were established in culture with irradiated TC-1 cells (100:1, splenocytes:TC-1) as feeder cells; stimulated in vitro for 5 days, then used in a standard $^{51}$Cr release assay, using the following targets: EL-4, EL-4/E7, or EL-4 pulsed with E7 H-2b peptide (RAHYNIVTF). E:T cell ratios, performed in triplicate, were 80:1, 40:1, 20:1, 10:1, 5:1, and 2.5:1. Following a 4-h incubation at 37° C., cells were pelleted, and 50 μl supernatant was removed from each well. Samples were assayed with a Wallac 1450 scintillation counter (Gaithersburg, Md.). The percent specific lysis was determined as [(experimental counts per minute (cpm)−spontaneous cpm)/(total cpm−spontaneous cpm)]×100.

TC-1-Specific Proliferation

C57BL/6 mice were immunized with 0.1 $LD_{50}$ and boosted by i.p. injection 20 days later with 1 $LD_{50}$ Lm-LLO-E7, Lm-E7, Lm-LLO-NP, or Lm-Gag. Six days after boosting, spleens were harvested from immunized and naive mice. Splenocytes were established in culture at $5 \times 10^5$/well in flat-bottom 96-well plates with $2.5 \times 10^4$, $1.25 \times 10^4$, $6 \times 10^3$, or $3 \times 10^3$ irradiated TC-1 cells/well as a source of E7 Ag, or without TC-1 cells or with 10 μg/ml Con A. Cells were pulsed 45 h later with 0.5 μCi [$^3$H]thymidine/well. Plates were harvested 18 h later using a Tomtec harvester 96 (Orange, Conn.), and proliferation was assessed with a Wallac 1450 scintillation counter. The change in cpm was calculated as experimental cpm—no Ag cpm.

Flow Cytometric Analysis

C57BL/6 mice were immunized intravenously (i.v.) with 0.1 $LD_{50}$ Lm-LLO-E7 or Lm-E7 and boosted 30 days later. Three-color flow cytometry for CD8 (53-6.7, PE conjugated), CD62 ligand (CD62L; MEL-14, APC conjugated), and E7 H-2Db tetramer was performed using a FACSCalibur® flow cytometer with CellQuest® software (Becton Dickinson, Mountain View, Calif.). Splenocytes harvested 5 days after the boost were stained at room temperature (rt) with H-2Db tetramers loaded with the E7 peptide (RAHYNIVTF) or a control (HIV-Gag) peptide. Tetramers were used at a 1/200 dilution and were provided by Dr. Larry R. Pease (Mayo Clinic, Rochester, Minn.) and by the NIAID Tetramer Core Facility and the NIH AIDS Research and Reference Reagent Program. Tetramer, CD8, $CD62L^{low}$ cells were analyzed.

B16F0-Ova Experiment

24 C57BL/6 mice were inoculated with $5 \times 10^5$ B16F0-Ova cells. On days 3, 10 and 17, groups of 8 mice were immunized with 0.1 $LD_{50}$ Lm-OVA ($10^6$ cfu), Lm-LLO-OVA ($10^8$ cfu) and eight animals were left untreated.

Statistics

For comparisons of tumor diameters, mean and SD of tumor size for each group were determined, and statistical significance was determined by Student's t test. $p \leq 0.05$ was considered significant.

Results

Figure 3:
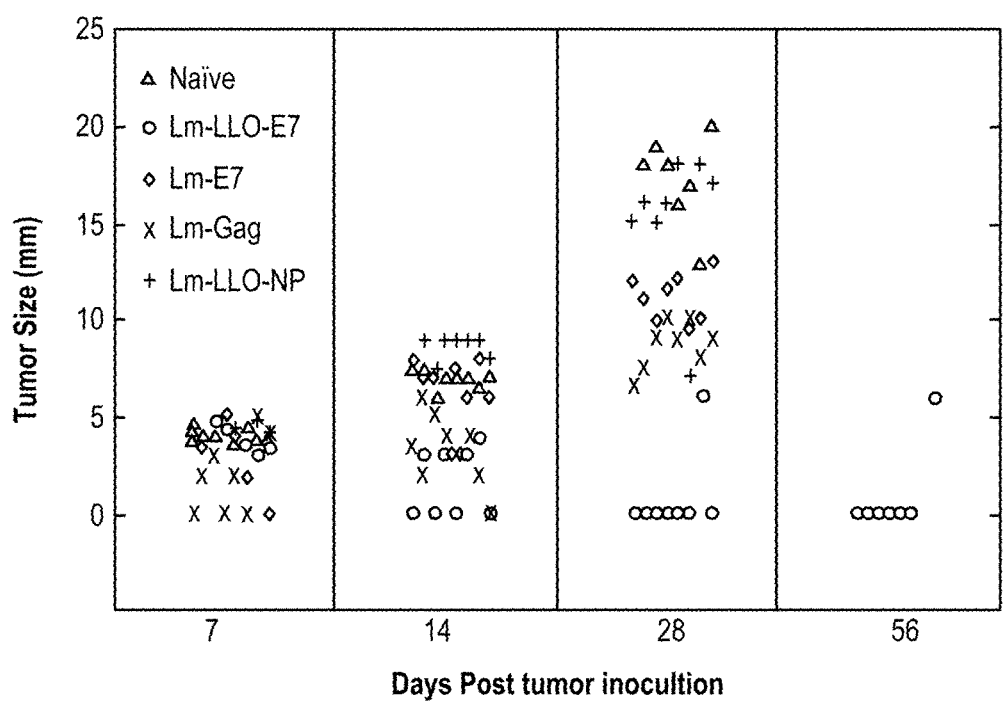
FIG. 3. Tumor immunotherapeutic efficacy of LLO-E7 fusions. Tumor size in millimeters in mice is shown at 7, 14, 21, 28 and 56 days post tumor-inoculation. Naive mice: open-circles; Lm-LLO-E7: filled circles; Lm-E7: squares; Lm-Gag: open diamonds; and Lm-LLO-NP: filled triangles.

Lm-E7 and Lm-LLO-E7 were compared for their abilities to impact on TC-1 growth. Subcutaneous tumors were established on the left flank of C57BL/6 mice. Seven days later tumors had reached a palpable size (4-5 mm). Mice were vaccinated on days 7 and 14 with 0.1 $LD_{50}$ Lm-E7, Lm-LLO-E7, or, as controls, Lm-Gag and Lm-LLO-NP. Lm-LLO-E7 induced complete regression of 75% of established TC-1 tumors, while tumor growth was controlled in the other 2 mice in the group (FIG. 3). By contrast, immunization with Lm-E7 and Lm-Gag did not induce tumor regression. This experiment was repeated multiple times, always with very similar results. In addition, similar results were achieved for Lm-LLO-E7 under different immunization protocols. In another experiment, a single immunization was able to cure mice of established 5 mm TC-1 tumors.

In other experiments, similar results were obtained with 2 other E7-expressing tumor cell lines: C3 and EL-4/E7. To confirm the efficacy of vaccination with Lm-LLO-E7, animals that had eliminated their tumors were re-challenged with TC-1 or EL-4/E7 tumor cells on day 60 or day 40, respectively. Animals immunized with Lm-LLO-E7 remained tumor free until termination of the experiment (day 124 in the case of TC-1 and day 54 for EL-4/E7).

Thus, expression of an antigen as a fusion protein with ΔLLO enhances the immunogenicity of the antigen.

Example 2: Lm-LLO-E7 Treatment Elicits TC-1 Specific Splenocyte Proliferation

Figure 4:
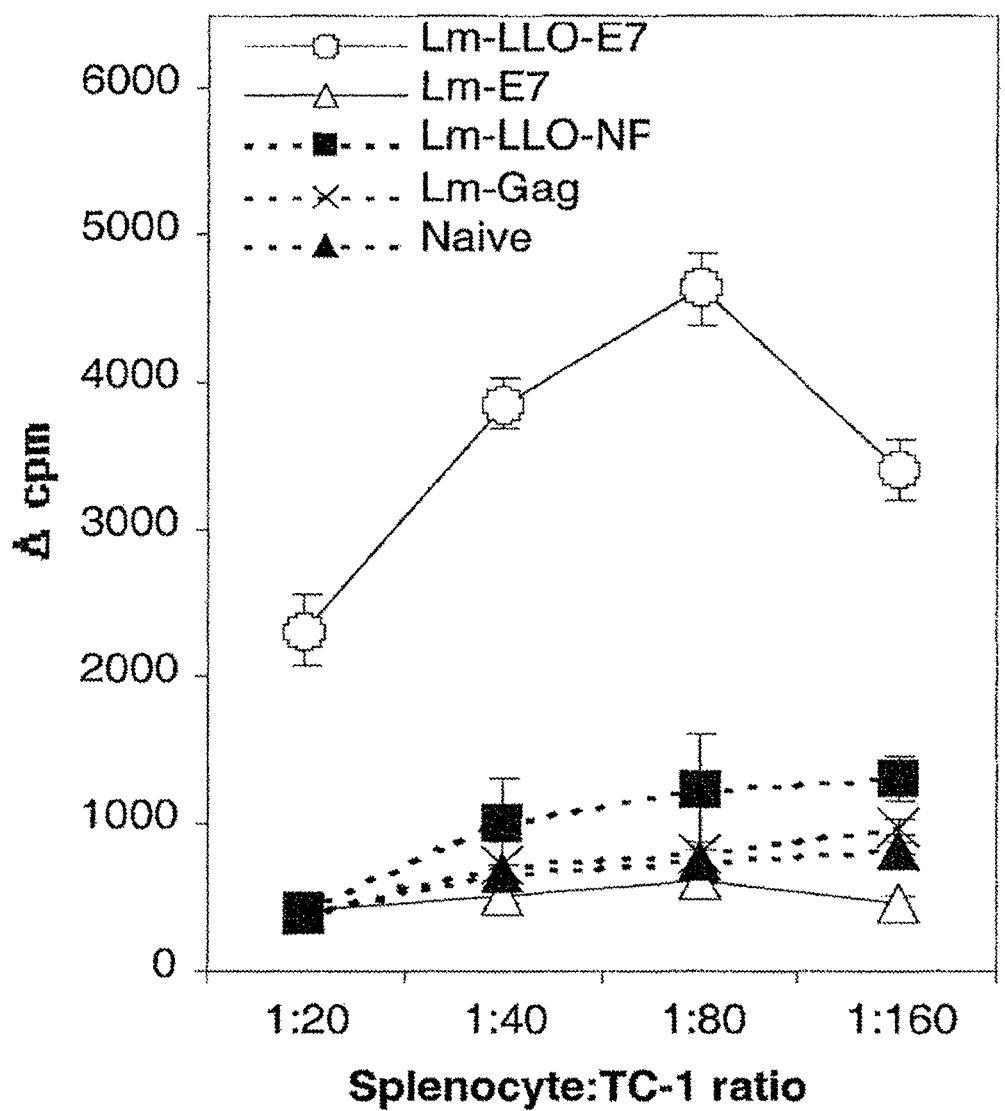
FIG. 4. Splenocytes from Lm-LLO-E7-immunized mice proliferate when exposed to TC-1 cells. C57BL/6 mice were immunized and boosted with Lm-LLO-E7, Lm-E7, or control rLm strains. Splenocytes were harvested 6 days after the boost and plated with irradiated TC-1 cells at the ratios shown. The cells were pulsed with $^3$H thymidine and harvested. Cpm is defined as (experimental cpm)−(no-TC-1 control).

To measure induction of T cells by Lm-E7 with Lm-LLO-E7, TC-1-specific proliferative responses, a measure of antigen-specific immunocompetence, were measured in immunized mice. Splenocytes from Lm-LLO-E7-immunized mice proliferated when exposed to irradiated TC-1 cells as a source of E7, at splenocyte: TC-1 ratios of 20:1, 40:1, 80:1, and 160:1 (FIG. 4). Conversely, splenocytes from Lm-E7 and rLm control-immunized mice exhibited only background levels of proliferation.

Example 3: Fusion of E7 to LLO, ActA, or a Pest Amino Acid Sequence Enhances E7-Specific Immunity and Generates Tumor-Infiltrating E7-Specific CD8+ Cells Materials and Experimental Methods 500 mcl (microliter) of MATRIGEL®, comprising 100 mcl of $2 \times 10^5$ TC-1 tumor cells in phosphate buffered saline (PBS) plus 400 mcl of MATRIGEL® (BD Biosciences, Franklin Lakes, N.J.) were implanted subcutaneously on the left flank of 12 C57BL/6 mice (n=3). Mice were immunized intraperitoneally on day 7, 14 and 21, and spleens and tumors were harvested on day 28. Tumor MATRIGELs were removed from the mice and incubated at 4° C. overnight in tubes containing 2 milliliters (ml) of RP 10 medium on ice. Tumors were minced with forceps, cut into 2 mm blocks, and incubated at 37° C. for 1 hour with 3 ml of enzyme mixture (0.2 mg/ml collagenase-P, 1 mg/ml DNAse-1 in PBS). The tissue suspension was filtered through nylon mesh and washed with 5% fetal bovine serum+0.05% of $NaN_3$ in PBS for tetramer and IFN-gamma staining.

Splenocytes and tumor cells were incubated with 1 micromole (mcm) E7 peptide for 5 hours in the presence of brefeldin A at $10^7$ cells/ml. Cells were washed twice and incubated in 50 mcl of anti-mouse Fc receptor supernatant (2.4 G2) for 1 hour or overnight at 4° C. Cells were stained for surface molecules CD8 and CD62L, permeabilized, fixed using the permeabilization kit Golgi-Stop® or Golgi-Plug® (Pharmingen, San Diego, Calif.), and stained for IFN-gamma. 500,000 events were acquired using two-laser flow cytometer FACSCalibur and analyzed using Cellquest Software (Becton Dickinson, Franklin Lakes, N.J.). Percentages of IFN-gamma secreting cells within the activated ($CD62L^{low}$) CD8+ T cells were calculated.

For tetramer staining, H-$2D^b$ tetramer was loaded with phycoerythrin (PE)-conjugated E7 peptide (RAHYNIVTF, SEQ ID NO: 24), stained at rt for 1 hour, and stained with anti-allophycocyanin (APC) conjugated MEL-14 (CD62L) and FITC-conjugated CD8+ at 4° C. for 30 mm Cells were analyzed comparing tetramer+CD8+ $CD62L^{low}$ cells in the spleen and in the tumor.

Results

To analyze the ability of Lm-ActA-E7 to enhance antigen specific immunity, mice were implanted with TC-1 tumor cells and immunized with either Lm-LLO-E7 ($1 \times 10^7$ CFU), Lm-E7 ($1 \times 10^6$ CFU), or Lm-ActA-E7 ($2 \times 10^8$ CFU), or were untreated (naïve). Tumors of mice from the Lm-LLO-E7 and Lm-ActA-E7 groups contained a higher percentage of IFN-gamma-secreting CD8+ T cells (FIG. 5A) and tetramer-specific CD8+ cells (FIG. 5B) than in Lm-E7 or naive mice.

Figure 6:
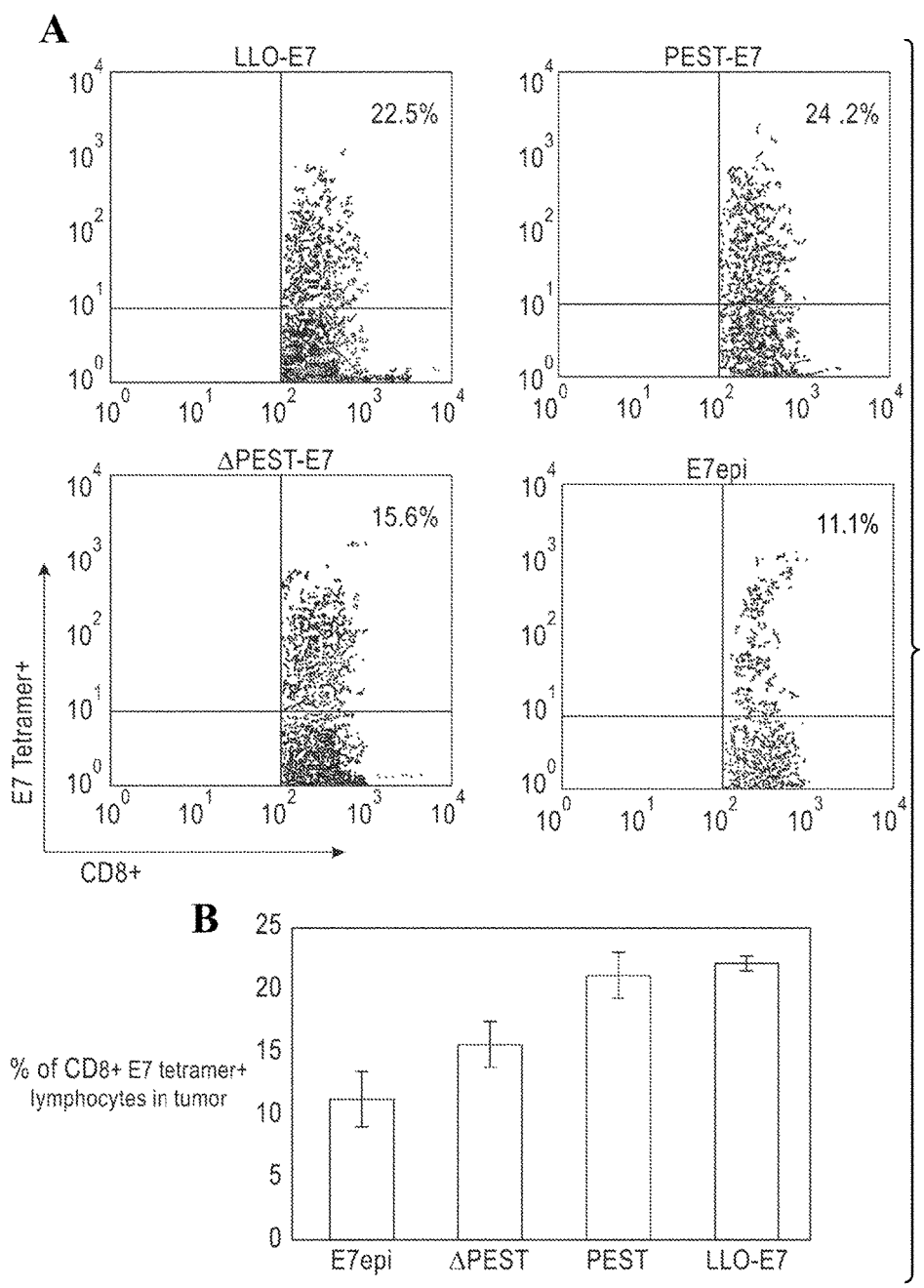
FIG. 6. *Listeria* constructs containing PEST regions induce a higher percentage of E7-specific lymphocytes within the tumor. A. representative data from 1 experiment. B. average and SE of data from all 3 experiments.

In another experiment, tumor-bearing mice were administered Lm-LLO-E7, Lm-PEST-E7, Lm-ΔPEST-E7, or Lm-E7epi, and levels of E7-specific lymphocytes within the tumor were measured. Mice were treated on days 7 and 14 with 0.1 $LD_{50}$ of the 4 vaccines. Tumors were harvested on day 21 and stained with antibodies to CD62L, CD8, and with the E7/Db tetramer. An increased percentage of tetramer-positive lymphocytes within the tumor were seen in mice vaccinated with Lm-LLO-E7 and Lm-PEST-E7 (FIG. 6A). This result was reproducible over three experiments (FIG. 6B).

Thus, Lm-LLO-E7, Lm-ActA-E7, and Lm-PEST-E7 are each efficacious at induction of tumor-infiltrating CD8+ T cells and tumor regression.

Example 4: Passaging of *Listeria* Vaccine Vectors Through Mice Elicits Increased Immune Responses to Heterologous and Endogenous Antigens Materials and Experimental Methods Bacterial Strains

*L. monocytogenes* strain 10403S, serotype 1 (ATCC, Manassas, Va.) was the wild type organism used in these studies and the parental strain of the constructs described below. Strain 10403S has an $LD_{50}$ of approximately $5 \times 10^4$ CFU when injected intraperitoneally into BALB/c mice. "Lm-Gag" is a recombinant LM strain containing a copy of the HIV-1 strain HXB (subtype B laboratory strain with a syncytia-forming phenotype) gag gene stably integrated into the Listerial chromosome using a modified shuttle vector pKSV7. Gag protein was expressed and secreted by the strain, as determined by Western blot. All strains were grown in brain-heart infusion (BHI) broth or agar plates (Difco Labs, Detroit, Mich.).

Bacterial Culture

Bacteria from a single clone expressing the passenger antigen and/or fusion protein were selected and cultured in BHI broth overnight. Aliquots of this culture were frozen at −70° C. with no additives. From this stock, cultures were grown to 0.1-0.2 O.D. at 600 nm, and aliquots were again frozen at −70° C. with no additives. To prepare cloned bacterial pools, the above procedure was used, but after each passage a number of bacterial clones were selected and checked for expression of the target antigen, as described herein. Clones in which expression of the foreign antigen was confirmed were used for the next passage.

Passage of Bacteria in Mice 6-8 week old female BALB/c (H-2d) mice were purchased from Jackson Laboratories (Bar Harbor, Me.) and were maintained in a pathogen-free microisolator environment. The titer of viable bacteria in an aliquot of stock culture, stored frozen at −70° C., was determined by plating on BHI agar plates on thawing and prior to use. In all, $5 \times 10^5$ bacteria were injected intravenously into BALB/c mice. After 3 days, spleens were harvested, homogenized, and serial dilutions of the spleen homogenate were incubated in BHI broth overnight and plated on BHI agar plates. For further passage, aliquots were again grown to 0.1-0.2 O.D., frozen at −70° C., and bacterial titer was again determined by serial dilution. After the initial passage (passage 0), this sequence was repeated for a total of 4 times.

Intracellular Cytokine Stain for IFN-Gamma

Lymphocytes were cultured for 5 hours in complete RPMI-10 medium supplemented with 50 U/ml human recombinant IL-2 and 1 microliter/ml Brefeldin A (Golgistop™; PharMingen, San Diego, Calif.) in the presence or absence of either the cytotoxic T-cell (CTL) epitope for HIV-GAG (AMQMLKETI; SEQ ID No: 25), *Listeria* LLO (GYKDGNEYI; SEQ ID No: 26) or the HPV virus gene E7 (RAHYNIVTF) (SEQ ID No: 24), at a concentration of 1 micromole. Cells were first surface-stained, then washed and subjected to intracellular cytokine stain using the Cytofix/Cytoperm kit in accordance with the manufacturers recommendations (PharMingen, San Diego, Calif.). For intracellular IFN-gamma stain, FITC-conjugated rat anti-mouse IFN-gamma monoclonal antibody (clone XMG 1.2) and its isotype control Ab (rat IgGl; both from PharMingen) was used. In all, $10^6$ cells were stained in PBS containing 1% Bovine Serum Albumin and 0.02% sodium azide (FACS Buffer) for 30 minutes at 4° C. followed by 3 washes in FACS buffer. Sample data were acquired on either a FACScan™ flowcytometer or FACSCalibur™ instrument (Becton Dickinson, San Jose, Calif.). Three-color flow cytometry for CD8 (PERCP conjugated, rat anti-mouse, clone 53-6.7 Pharmingen, San Diego, Calif.), CD62L (APC conjugated, rat anti-mouse, clone MEL-14), and intracellular IFN-gamma was performed using a FACSCalibur™ flow cytometer, and data were further analyzed with CELLQuest software (Becton Dickinson, Mountain View, Calif.). Cells were gated on CD8 high and $CD62L^{low}$ before they were analyzed for CD8+ and intracellular IFN-gamma staining.

Results

Passaging in Mice Increases the Virulence of Recombinant *Listeria Monocytogenes*

Three different constructs were used to determine the impact of passaging on recombinant *Listeria* vaccine vectors. Two of these constructs carry a genomic insertion of the passenger antigen: the first comprises the HIV gag gene (Lm-Gag), and the second comprises the HPV E7 gene (Lm-E7). The third (Lm-LLO-E7) comprises a plasmid with the fusion gene for the passenger antigen (HPV E7) fused with a truncated version of LLO and a gene encoding prfA, the positive regulatory factor that controls *Listeria* virulence factors. This plasmid was used to complement a prfA negative mutant so that in a live host, selection pressures would favor conservation of the plasmid, because without it the bacterium is avirulent. All 3 constructs had been propagated extensively in vitro for many bacterial generations.

Figure 7A:
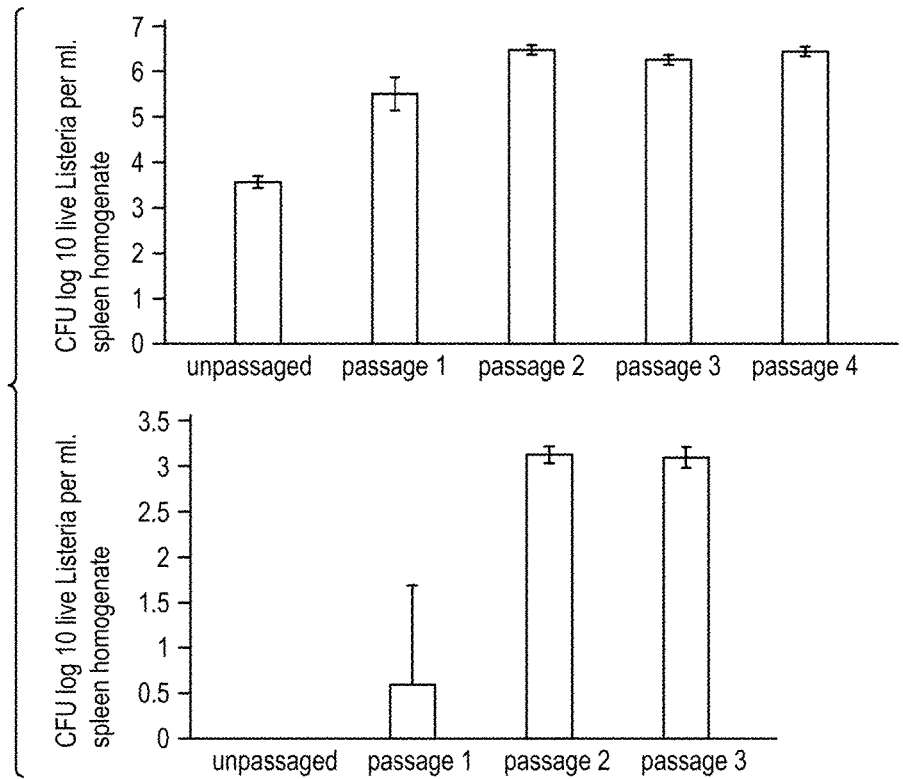
FIG. 7A. Effect of passaging on bacterial load (virulence) of recombinant *Listeria* vaccine vectors. Top panel. Lm-Gag. Bottom panel. Lm-LLO-E7.
Figure 7B:
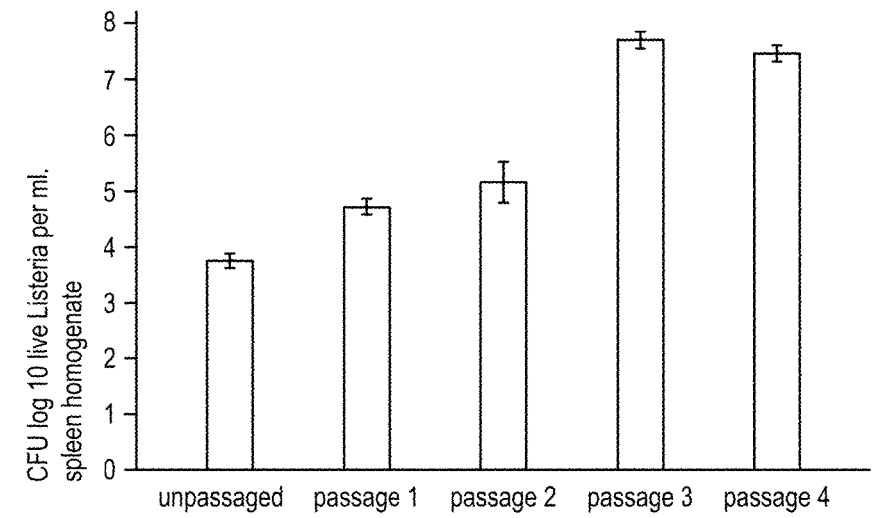
FIG. 7B. Effect of passaging on bacterial load of recombinant Lm-E7 in the spleen. Average CFU of live bacteria per milliliter of spleen homogenate from four mice is depicted.

Passaging the bacteria resulted in an increase in bacterial virulence, as measured by numbers of surviving bacteria in the spleen, with each of the first 2 passages. For Lm-Gag and Lm-LLO-E7, virulence increased with each passage up to passage 2 (FIG. 7A). The plasmid-containing construct, Lm-LLO-E7, demonstrated the most dramatic increase in virulence. Prior to passage, the initial immunizing dose of Lm-LLO-E7 had to be increased to $10^7$ bacteria and the spleen had to be harvested on day 2 in order to recover bacteria (whereas an initial dose of $10^5$ bacteria for Lm-Gag was harvested on day 3). After the initial passage, the standard dosage of Lm-LLO-E7 was sufficient to allow harvesting on day 3. For Lm-E7, virulence increased by 1.5 orders of magnitude over unpassaged bacteria (FIG. 7B).

Thus, passage through mice increases the virulence of *Listeria* vaccine strains.

Passaging Increases the Ability of *L. monocytogenes* to Induce CD8+ T Cells

Figure 8:
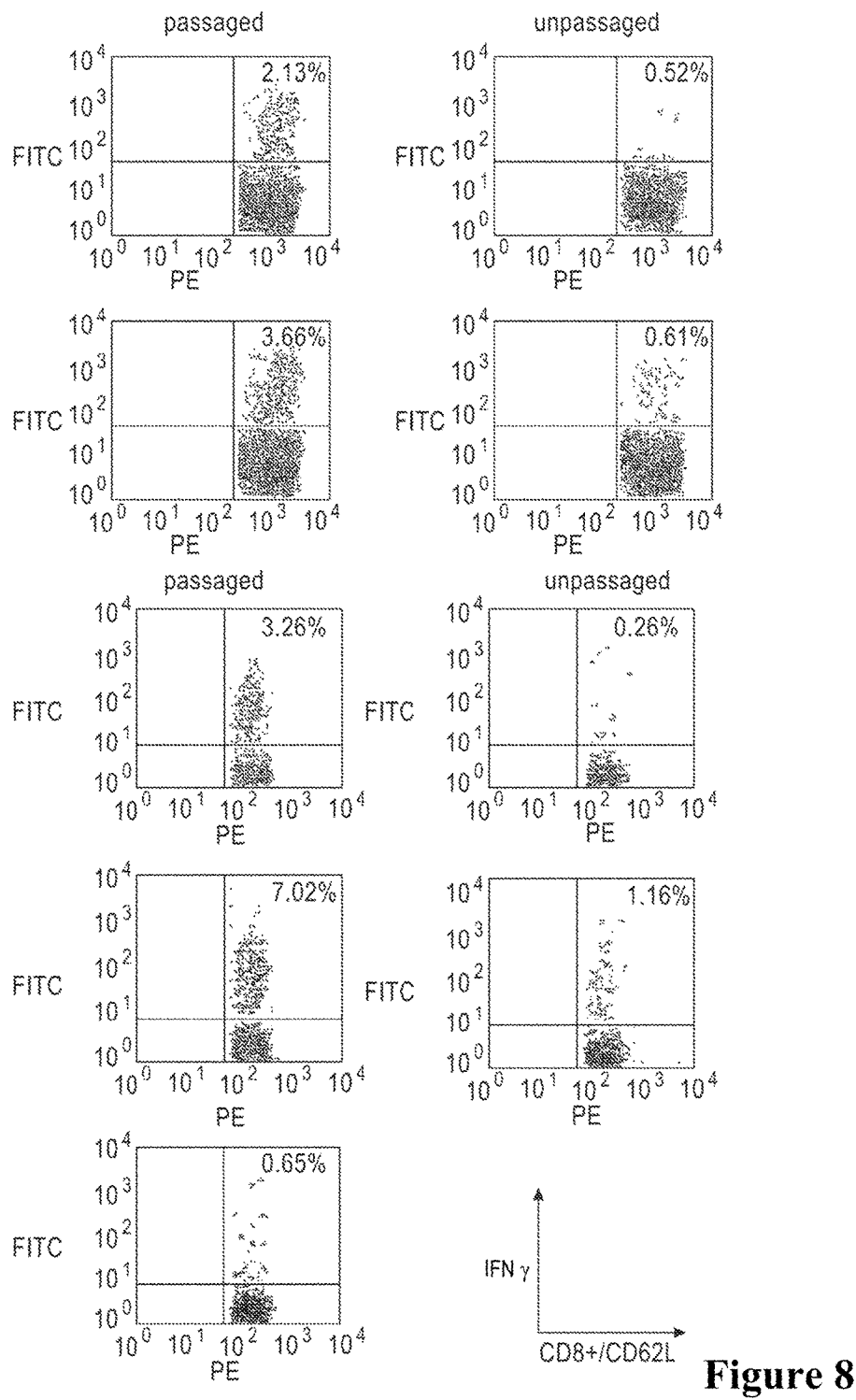
FIG. 8 shows induction of antigen-specific $CD8^+$ T-cells for HIV-Gag and LLO after administration of passaged Lm-Gag versus unpassaged Lm-Gag. Mice were immunized with $10^3$ (A, B, E, F) or $10^5$ (C, D, G, H) CFU passaged *Listeria* vaccine vectors, and antigen-specific T-cells were analyzed. B, D, F, H: unpassaged *Listeria* vaccine vectors. A-D immune response to MHC class I HIV-Gag peptide. E-H: immune response to an LLO peptide. I: splenocytes from mice immunized with $10^5$ CFU passaged Lm-Gag stimulated with a control peptide from HPV E7.
Figure 9C:
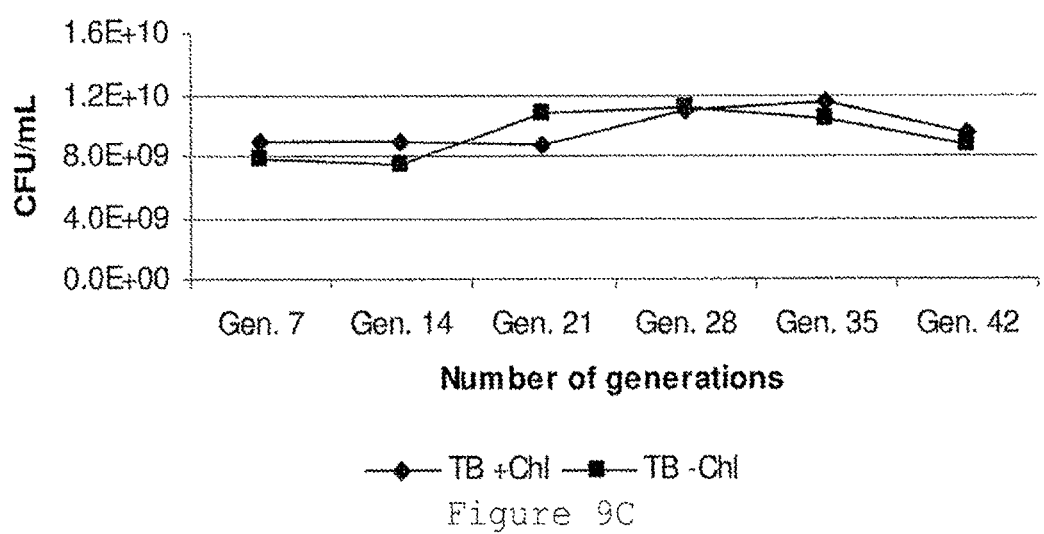
FIG. 9C shows quantitation of TB stability study.
Figure 10:
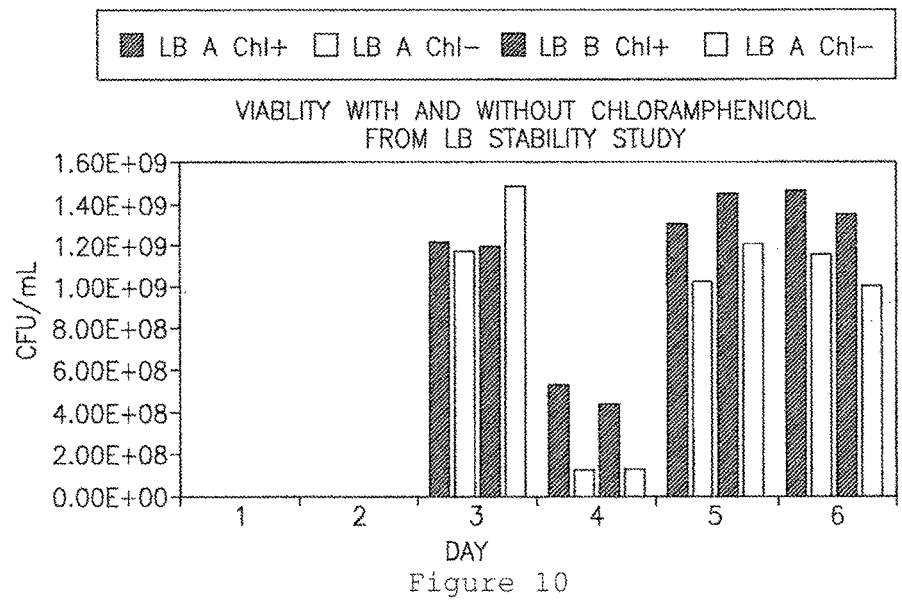
FIG. 10 shows numbers of viable bacteria chloramphenicol (CAP)-resistant and CAP-sensitive colony-forming units (CFU) from bacteria grown in LB. Dark bars: $CAP^+$; white bars: $CAP^-$. The two dark bars and two white bars for each time point represent duplicate samples.
Figure 11:
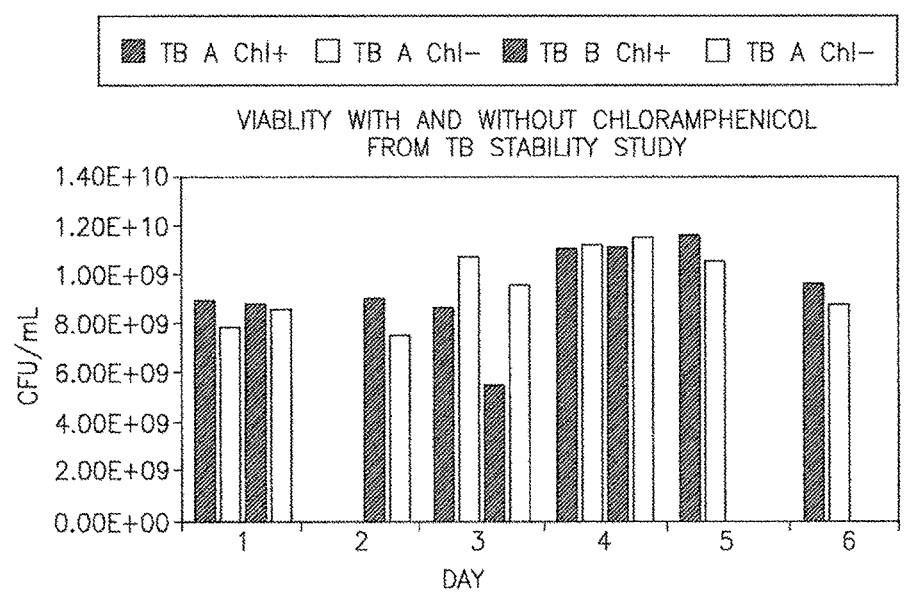
FIG. 11 shows numbers of viable bacteria CAP-resistant and CAP-sensitive CFU from bacteria grown in TB. Dark bars: CAP; white bars: CAP. The two dark bars and two white bars for each time point represent duplicate samples.

Next, the effect of passaging on induction of antigen-specific CD8+ T cells was determined by intracellular cytokine staining with immunodominant peptides specific for MHC-class I using HIV-Gag peptide AMQMLKETI (SEQ ID No: 25) and LLO 91-99 (GYKDGNEYI; SEQ ID No: 26). Injection of $10^3$ CFU passaged bacteria (Lm-Gag) into mice elicited significant numbers of HIV-Gag-specific CD8+ T cells, while the same dose of non-passaged Lm-Gag induced no detectable Gag-specific CD8+ T cells. Even increasing the dose of unpassaged bacteria 100-fold did not compensate for their relative avirulence; in fact, no detectable Gag-specific CD8+ T cells were elicited even at the higher dose. The same dose increase with passaged bacteria increased Gag-specific T cell induction by 50% (FIG. 8). The same pattern of induction of antigen-specific CD8+ T cells was observed with LLO-specific CD8+ T cells, showing that these results were not caused by the properties of the passenger antigen, since they were observed with LLO, an endogenous *Listeria* antigen.

Thus, passage through mice increases the immunogenicity of *Listeria* vaccine strains.

Example 5: A PrfA-Containing Plasmid is Stable in an LM Strain with a PrfA Deletion in the Absence of Antibiotics Materials and Experimental Methods Bacteria

*L. monocytogenes* strain XFL7 contains a 300 base pair deletion in the prfA gene XFL7 carries pGG55 which partially restores virulence and confers CAP resistance, and is described in United States Patent Application Publication No. 200500118184.

Development of Protocol for Plasmid Extraction from *Listeria*

1 mL of *Listeria monocytogenes* Lm-LLO-E7 research working cell bank vial was inoculated into 27 mL BH1 medium containing 34 μg/mL CAP and grown for 24 hours at 37° C. and 200 rpm.

Seven 2.5 mL samples of the culture were pelleted (15000 rpm for 5 minutes), and pellets were incubated at 37° C. with 50 μl lysozyme solution for varying amounts of time, from 0-60 minutes.

Lysozyme solution:

29 μl 1 M dibasic Potassium Phosphate

21 μl 1 M monobasic Potassium Phosphate

500 μl 40% Sucrose (filter sterilized through 0.45/μm filter)

450 μl water

60 μl lysozyme (50 mg/mL)

After incubation with the lysozyme, the suspensions were centrifuged as before and the supernatants discarded. Each pellet was then subjected to plasmid extraction by a modified version of the QIAprep Spin Miniprep Kit® (Qiagen, Germantown, Md.) protocol. The changes to the protocol were as follows:

1. The volumes of buffers PI, P2 and N3 were all increased threefold to allow complete lysis of the increased biomass.
2. 2 mg/mL of lysozyme was added to the resuspended cells before the addition of P2. The lysis solution was then incubated at 37° C. for 15 minutes before neutralization.
3. The plasmid DNA was resuspended in 30 μL rather than 50 μL to increase the concentration.

In other experiments, the cells were incubated for 15 min in P1 buffer+Lysozyme, then incubated with P2 (lysis buffer) and P3 (neutraliztion buffer) at room temperature.

Equal volumes of the isolated plasmid DNA from each subculture were run on an 0.8% agarose gel stained with ethidium bromide and visualized for any signs of structural or segregation instability.

The results showed that plasmid extraction from *L. monocytogenes* Lm-LLO-E7 increases in efficiency with increasing incubation time with lysozyme, up to an optimum level at approximately 50 minutes incubation.

These results provide an effective method for plasmid extraction from *Listeria* vaccine strains.

Replica Plating

Dilutions of the original culture were plated onto plates containing LB or TB agar in the absence or presence of 34 μg/mL CAP. The differences between the counts on selective and non-selective agar were used to determine whether there was any gross segregational instability of the plasmid.

Results

The genetic stability (i.e. the extent to which the plasmid is retained by or remains stably associated with the bacteria in the absence of selection pressure; e.g. antibiotic selection pressure) of the pGG55 plasmid in *L. monocytogenes* strain XFL7 in the absence of antibiotic was assessed by serial sub-culture in both Luria-Bertani media (LB: 5 g/L NaCl, 10 g/ml soy peptone, 5 g/L yeast extract) and Terrific Broth media (TB: 10 g/L glucose, 11.8 g/L soy peptone, 23.6 g/L yeast extract, 2.2 g/L $KH_2PO_4$, 9.4 g/L $K_2HPO_4$), in duplicate cultures. 50 mL of fresh media in a 250 mL baffled shake flask was inoculated with a fixed number of cells (1 ODmL), which was then subcultured at 24 hour intervals. Cultures were incubated in an orbital shaker at 37° C. and 200 rpm. At each subculture the $OD_{600}$ was measured and used to calculate the cell doubling time (or generation) elapsed, until 30 generations were reached in LB and 42 in TB. A known number of cells (15 OD mL) at each subculture stage (approximately every 4 generations) were pelleted by centrifugation, and the plasmid DNA was extracted using the Qiagen QIAprep Spin Miniprep® protocol described above. After purification, plasmid DNA was subjected to agarose gel electrophoresis, followed by ethidium bromide staining. While the amount of plasmid in the preps varied slightly between samples, the overall trend was a constant amount of plasmid with respect to the generational number of the bacteria (FIGS. 9A-B). Thus, pGG55 exhibited stability in strain XFL7, even in the absence of antibiotic.

Plasmid stability was also monitored during the stability study by replica plating on agar plates at each stage of the subculture. Consistent with the results from the agarose gel electrophoresis, there was no overall change in the number of plasmid-containing cells throughout the study in either LB or TB liquid culture (FIGS. 10 and 11, respectively).

These findings demonstrate that prfA-encoding plasmids exhibit stability in the absence of antibiotic in *Listeria* strains containing mutations in prfA.

Materials and Methods (Examples 6-10)

PCR Reagents

The primers used for amplification of the prfA gene and discrimination of the D133V mutation are shown in Table 1. Stock solutions of the primers ADV451, 452 and 453 were prepared by diluting the primers in TE buffer to 400 μM. An aliquot of the stock solution was further diluted to 20 μM in water (PCR grade) to prepare a working solution. Primers were stored at −20° C. The reagents used in the PCR are shown in Table 2.

TABLE 1

Primers ADV451, 452 and 453.

| Primer | Orientation | Sequence (5' → 3') | Specificity |
|---|---|---|---|
| ADV451 | Forward | CCTAGCTAAATTTAATGT (SEQ ID NO: 28) | D133V mutation |
| ADV452 | Forward | CCTAGCTAAATTTAATGA (SEQ ID NO: 29) | Wild-type sequence |

TABLE 1-continued Primers ADV451, 452 and 453.

| Primer | Orientation | Sequence (5' → 3') | Specificity |
|---|---|---|---|
| ADV453 | Reverse | TAATTTTCCCCAAGTAGCAGG (SEQ ID NO: 30) | Shared sequence |

TABLE 2

PCR reagents.

| | Description | Provider | Catalog number |
|---|---|---|---|
| 1 | 0.2 ml thin-walled PCR tubes: GeneAmp autoclaved reaction tube with cap | Applied Biosystems | N801-0612 |
| 2 | Water (PCR reagent) | Sigma | W1754 |
| 3 | Taq DNA Polymerase with 10x reaction buffer containing 15 mM $MgCl_2$ | Sigma | D1806 |
| 4 | Set of deoxynucleotides (dNTPs), 10 mM each | Sigma | D7295 |
| 5 | Primers ADV451, ADV452 and ADV453 | Invitrogen | |
| 6 | Template DNA, midipreparations of pGG55 plasmids | | |
| 7 | Thermal cycler PTC200 (48 wells block) | MJ Research | |

Plasmid DNA Preparation pGG55 plasmids with (pGG55 D133V) and without (pGG55 WT) the prfA mutation were extracted and purified by midipreparations either from *E. coli* or *Listeria monocytogenes* using the PureLink™ HiPure Plasmid Midiprep Kit (Invitrogen, K2100-05), according to the manufacturer's instructions. For plasmid purification from *Listeria*, bacterial strains carrying the pGG55 D133V or WT plasmids were streak plated from frozen stocks in BHI agar plates supplemented with chloramphenicol (25 µg/ml). A single colony from each strain was grown in 5 ml of selective medium (BHI broth with 25 µg/ml of chloramphenicol) for 6 hours with vigorous shaking at 37° C. and subinoculated 1:500 in 100 ml of selective medium for overnight growth under similar conditions. Bacteria from the overnight culture were harvested by centrifugation at 4,000×g for 10 minutes and resuspended buffer R3 (resuspension buffer) containing 2 mg/ml of lysozyme (Sigma, L7001). The bacteria suspension was incubated for at least 1 hour at 37° C. before proceeding to the regular protocol. Concentration and purity of the eluted plasmids were measured in a spectrophotometer at 260 nm and 280 nm. To prepare the template DNAs, the pGG55 D133V and WT plasmids were resuspended in water to a final concentration of 1 ng/µl from the midiprep stock solution. For the pGG55 WT plasmid, serial 10-fold dilutions from the 1 ng/µl solution were prepared, corresponding to dilutions from $10^{-1}$ to $10^{-7}$.

prfA Specific PCR Protocol to Test Clinical Grade Material

The reaction mixture contained 1×PCR buffer, 1.5 mM $MgCl_2$, 0.8 mM dNTPs, 0.4 µM of each primer, 0.05 U/µl of Taq DNA polymerase and 0.04 ng/µl of the pGG55 D133V template plasmid. For each test, 10 tubes were required and the key components in each tube in a 25 µl reaction are shown in the Table 3. For the PCR reaction, a master mix was prepared with enough reagents for 11 reactions as shown in Table 4, and 24 µl of this PCR mix was added to each tube. Subsequently, a total of 1 µl of the serially diluted pGG55 WT plasmid was added to the corresponding tubes: 1 ng in tube 3; 100 pg in tube 4; 10 pg in tube 5; 1 pg in tube 6; 100 fg in tube 7; 10 fg in tube 8; 1 fg in tube 9; 0.1 fg in tube 10. This serial dilution was used to calibrate a standard curve to determine the method sensitivity. Additionally, 0.5 µl of water and 0.5 µl of primer ADV451 (20 µM stock) were added in tube 1, and 1 µl of water added in tube 2, completing 25 µl of final volume. The quantities of each reagent per tube for a 25 µl reaction are shown in Table 5. The PCR cycling conditions used in the reaction are shown in Table 6.

After conclusion of the PCR reaction, 5 µl of gel-loading buffer (6x, with bromophenol blue) was added to each sample and 10 µl were analyzed by electrophoresis in 1.2% agarose gel in TBE buffer. The gel dimensions were 7 cm×7 cm×1 cm with a 15 sample wells (1 mm×2 mm) comb. The gel was run at 100 V for ~30 minutes, until the bromophenol blue dye reached the middle of the gel. The gel was stained in ethidium bromide (0.5 µg/ml) for 20 minutes, destaining in water for 10 minutes. The gel is visualized by illumination with UV light and photographed. The image was analyzed using a band densitometry software (Quantity One version 4.5.1, BioRad).

TABLE 3

Set of individual PCR reactions to validate the method to detect the presence of wild-type prfA sequence in Lm-LLO-E7 samples.

| Tube | Primer A | Primer B | Template DNA | Function | Expected result |
|---|---|---|---|---|---|
| 1 | ADV451 | ADV453 | 1 ng of pGG55 (D133V) | Positive control for the ADV451 reaction | Positive |
| 2 | ADV452 | ADV453 | 1 ng of pGG55 (D133V) | Negative control for the ADV452 reaction (specificity) | Negative |
| 3 | ADV452 | ADV453 | 1 ng of pGG55 (wild-type) + 1 ng of pGG55 (D133V) | Positive control for the ADV452 reaction | Positive |
| 4 | ADV452 | ADV453 | 100 pg of pGG55 (wild-type) + 1 ng of pGG55 (D133V) | Test the sensitivity of the reaction | Positive |
| 5 | ADV452 | ADV453 | 10 pg of pGG55 (wild-type) + 1 ng of pGG55 (D133V) | Test the sensitivity of the reaction | Positive |
| 6 | ADV452 | ADV453 | 1 pg of pGG55 (wild-type) + 1 ng of pGG55 (D133V) | Test the sensitivity of the reaction | Positive |

TABLE 3-continued

Set of individual PCR reactions to validate the method to detect
the presence of wild-type prfA sequence in Lm-LLO-E7 samples.

| Tube | Primer A | Primer B | Template DNA | Function | Expected result |
|---|---|---|---|---|---|
| 7 | ADV452 | ADV453 | 100 fg of pGG55 (wild-type) + 1 ng pGG55 (D133V) | Test the sensitivity of the reaction | Positive |
| 8 | ADV452 | ADV453 | 10 fg of pGG55 (wild-type) + pGG55 (D133V) | Test the sensitivity of the reaction | Positive |
| 9 | ADV452 | ADV453 | 1 fg of pGG55 (wild-type) + pGG55 (D133V) | Test the sensitivity of the reaction | Weakly positive |
| 10 | ADV452 | ADV453 | 0.1 fg of pGG55 (wild-type) + pGG55 (D133V) | Test the sensitivity of the reaction | To be determined |

TABLE 4

Master PCR mix preparation.

| Reagent | Quantity (μl) |
|---|---|
| Water | 206.25 |
| Taq DNA Polymerase 10x reaction buffer containing 15 mM MgCl$_2$ | 27.5 |
| Deoxynucleotides (dNTPs) 10 mM each | 5.5 |
| Primers ADV452 (20 μM in water) | 5.5 |
| Primers ADV453 (20 μM in water) | 5.5 |
| pGG55 D133V (Lm-LLO-E7) plasmid (1 ng/μl) | 11 |
| Taq DNA Polymerase (5 U/μl) | 2.75 |
| Total | 264 |

TABLE 5

PCR protocol for validation of the method to detect the presence
of wild-type prfA sequence using primers ADV451, 452 and 453.

| Reagent | PCR |
|---|---|
| Water | 18.75 μl |
| PCR Buffer 10x + MgCl$_2$ 15 mM | 2.5 μl |
| Deoxynucleotides mix (dATP, dCTP, dGTP and dTTP) 10 mM each | 0.5 μl |
| Primer ADV452 (20 μM) | 0.5 μl |
| Primer ADV453 (20 μM) | 0.5 μl |
| Taq DNA polymerase (5 U/μl) | 0.25 μl |
| Template DNA (1 ng/μl) pGG55 D133V | 1 μl |
| Template DNA pGG55 WT (tubes 3 to 10)$^a$ | 1 μl |
| Final volume per tube$^b$ | 25 μl |

$^a$pGG55 WT (1 ng in tube 3; 100 pg in tube 4; 10 pg in tube 5; 1 pg in tube 6; 100 fg in tube 7; 10 fg in tube 8; 1 fg in tube 9; 0.1 fg in tube 10).
$^b$In tube 1, add 0.5 μl of water and 0.5 μl of primer ADV451 (20 μM stock); in tube 2 add 1 μl of water.

TABLE 6

PCR cycling conditions to detect the presence of wild-
type prfA sequence using primers ADV451, 452 and 453.

| Step | Temperature | Time | Number of cycles |
|---|---|---|---|
| 1. | 94° C. | 2 minutes and 30 seconds | 1 |
| 2. | 94° C. | 30 seconds | 1 |
| 3. | 53° C. | 30 seconds | 1 |
| 4. | 72° C. | 30 seconds | 1 |
| 5. | Repeat steps 2 to 4 | | 12 |
| 6. | 94° C. | 30 seconds | 1 |
| 7. | 50° C. | 30 seconds | 1 |
| 8. | 72° C. | 30 seconds | 1 |
| 9. | Repeat steps 6 to 8 | | 23 |
| 10. | 72° C. | 10 minutes | 1 |

Sequencing:

Sequencing of the plasmids was done using the dideoxy sequencing method. The plasmids pGG55 D133V and pGG55 WT were mixed at different ratios (1:1, 1:10, 1;100, 1:1,000 and 1:10,000). The total amount of plasmid in the mixture was kept constant (500 μg) and the plasmid containing the wild-type sequence was 10-fold serially diluted in relation to the D133V plasmid to determine the sensitivity of the method.

Results

Figure 12:
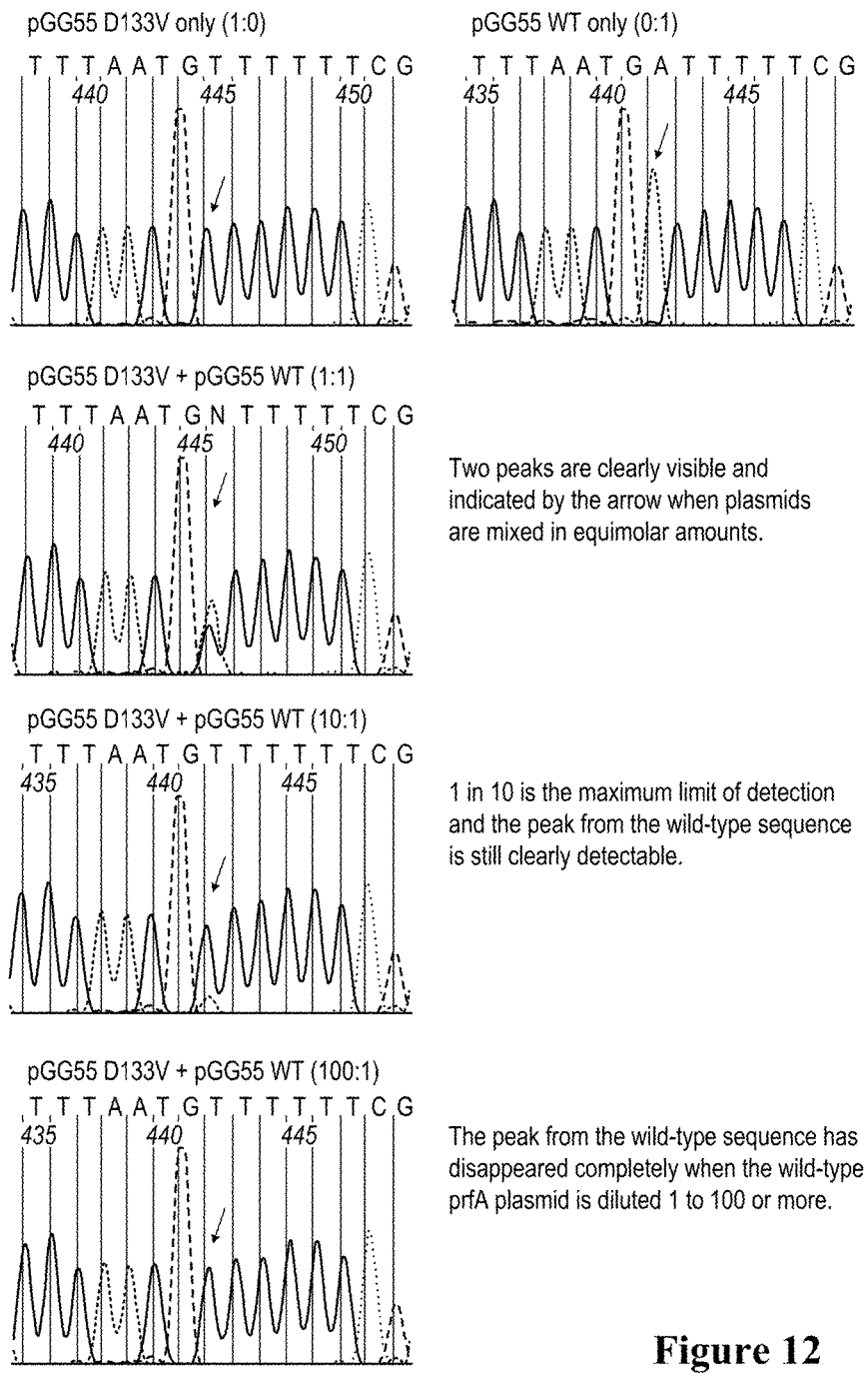
FIG. 12. Actual chromatograms showing the region of the D133V mutation (arrows). The mixture ratio is shown in parentheses.

Example 6: Sequencing is not a Sensitive Method to Detect the Reversion of the D133V Mutation To estimate the sensitivity of sequencing in detecting the wild-type prfA sequence, the pGG55 D133V and WT plasmids were mixed at the different ratios and sequenced. The results are shown in FIG. 12 and reveal that sequencing has a high specificity in discriminating the prfA D133V mutation (FIG. 12). On the other hand, the sensitivity is low and the maximum dilution of wild-type prfA pGG55 plasmid with a detectable peak in the sequence was 1 in 10 (FIG. 12). In conclusion, although sequencing is very specific, the sensitivity of the method is low and not appropriate to screen for the presence of rare events such as revertants of the prfA D133V mutation in Lm-LLO-E7 samples.

Example 7: Development of a Highly Specific and Sensitive PCR Method to Detect Reversion of the D133V Mutation Given the low sensitivity of sequencing to detect rare events, it became imperative to develop a more sensitive method with similar specificity to detect reversion of the D133V mutation to wild-type. To achieve this goal, we designed a PCR-based method that specifically amplifies the wild-type sequence and is sensitive enough to detect at least 1 wild-type copy of prfA in 10,000,000 copies of the D133V mutated sequence. We designed 3 primers for this method: ADV451, ADV452 and ADV453 (Table 1). Both ADV451 and ADV452 are forward primers and differ in the last nucleotide at the 3' position to discriminate the A→T (D133V) mutation at position 398 of the prfA gene. The ADV453 primer is the reverse primer located approximately 300 bp downstream the annealing site of the ADV451 and ADV452 primers (FIG. 13). The expected PCR band obtained with the primers ADV451 or ADV452 and ADV453 is 326 bp. Under stringent conditions, the ADV451 primer should only amplify the pGG55 D133V plasmid, whereas the ADV452 would be specific to the wild-type prfA sequence.

Example 8: Specificity of the PCR Method

Figure 14:
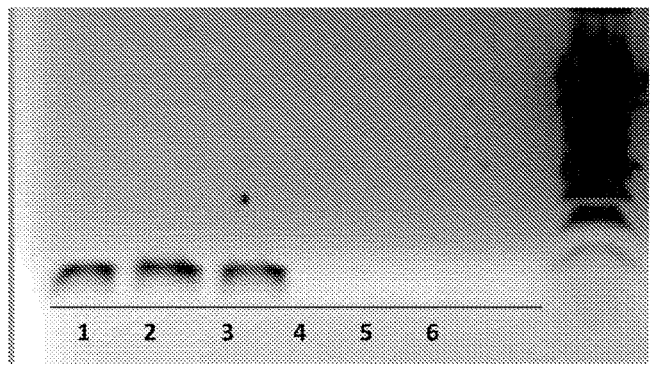
FIG. 14. Specificity of the PCR reaction using primers ADV451 and ADV453.

The reaction using the primer ADV451 was very specific and amplified the mutated D133V prfA sequence (lanes 1 to 3), but not the wild-type sequence (lanes 4 to 6). However, a very faint band can be detected in lane 4, when 5 ng of template DNA was used, but not with 1 ng (FIG. 14).

Figure 15:
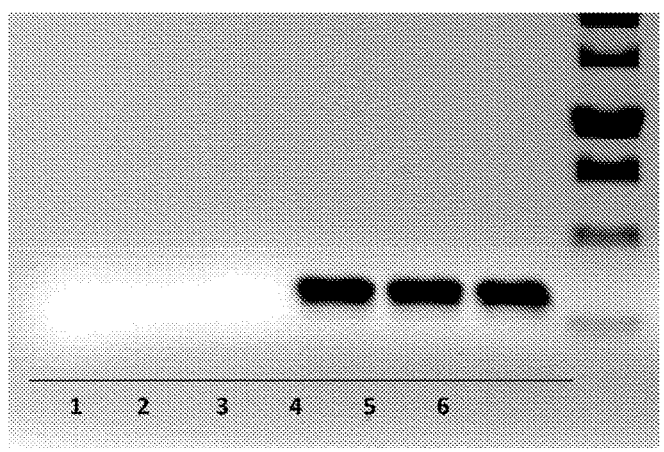
FIG. 15. Specificity of the PCR reaction using primers ADV452 and ADV453.
Figure 16:
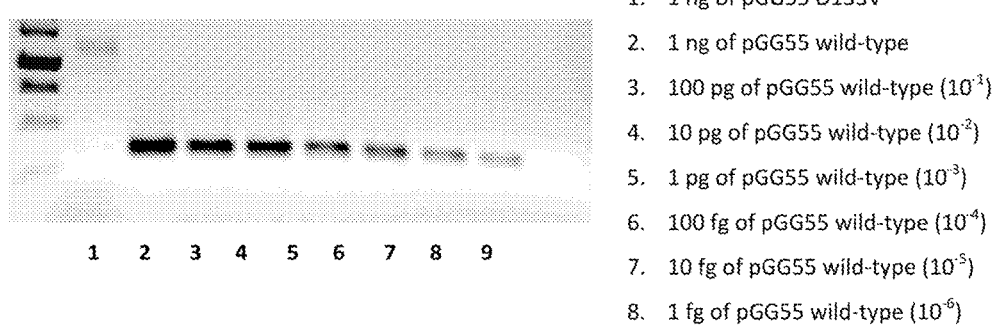
FIG. 16. Sensitivity of the PCR reaction to detect the wild-type prfA sequence using the primer ADV452 and 1 ng as the initial amount of DNA.

As shown in FIG. 15, the reaction with the ADV452 primer only amplified the wild-type prfA sequence (lanes 4, 5 and 6), and no bands were detected when the pGG55 carrying the D133V prfA mutation was used as a template (lanes 1, 2 and 3), even when using 5 ng of plasmid in the reaction (FIG. 16). In conclusion, the PCR reactions with primers ADV451 and ADV452 are very specific and able to discriminate the A ↔ T (D133V) mutation at position 398 of the prfA gene in the pGG55 plasmid. Based on these results, we selected the amount of 1 ng as the standard amount of template DNA to be used in the reaction.

Example 9: Sensitivity of the PCR Method

Figure 5:
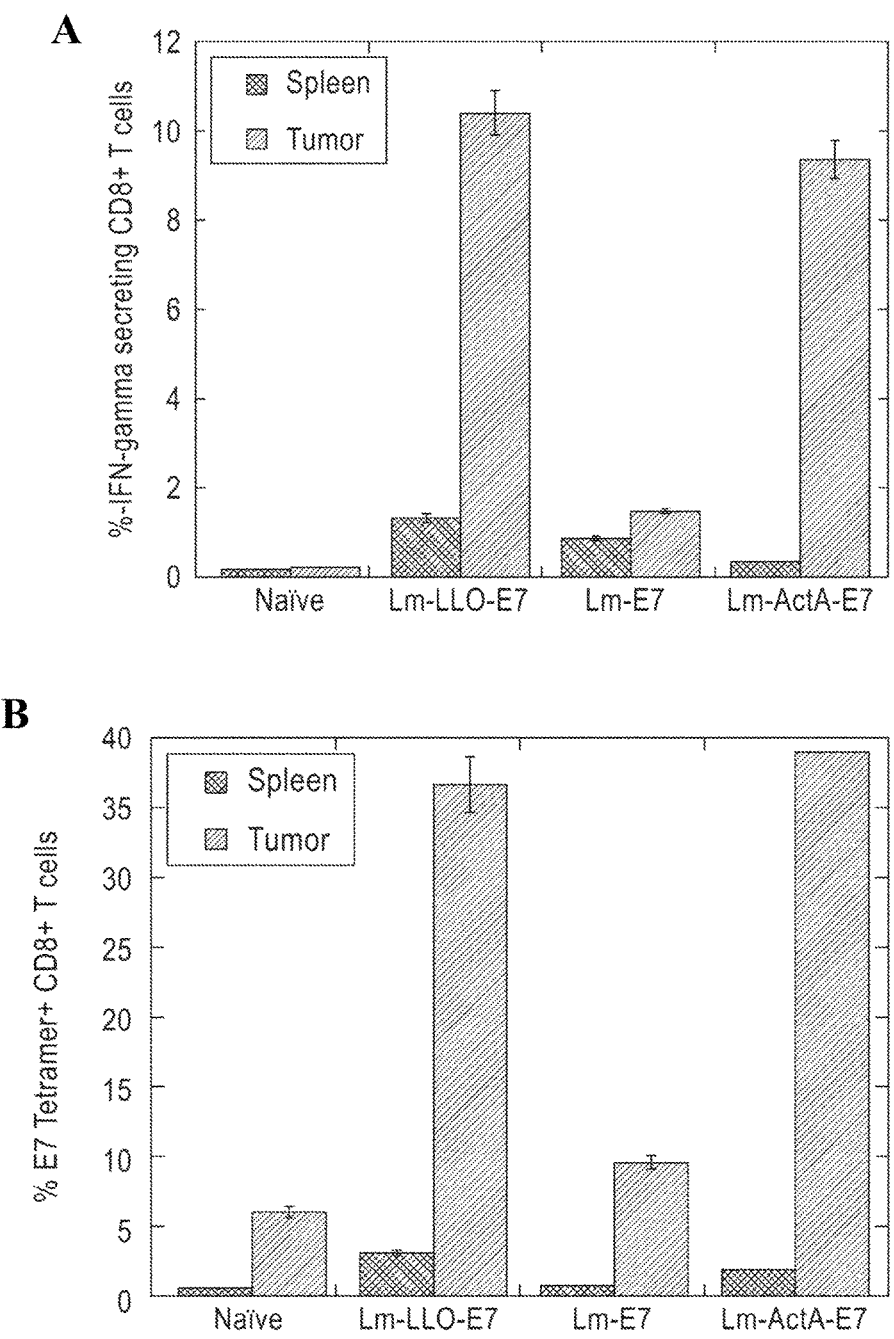
FIG. 5. A. Induction of E7-specific IFN-gamma-secreting $CD8^+$ T cells in the spleens and the numbers penetrating the tumors, in mice administered TC-1 tumor cells and subsequently administered Lm-E7, Lm-LLO-E7, Lm-ActA-E7, or no vaccine (naive). B. Induction and penetration of E7 specific $CD8^+$ cells in the spleens and tumors of the mice described for (A).
Figure 17:
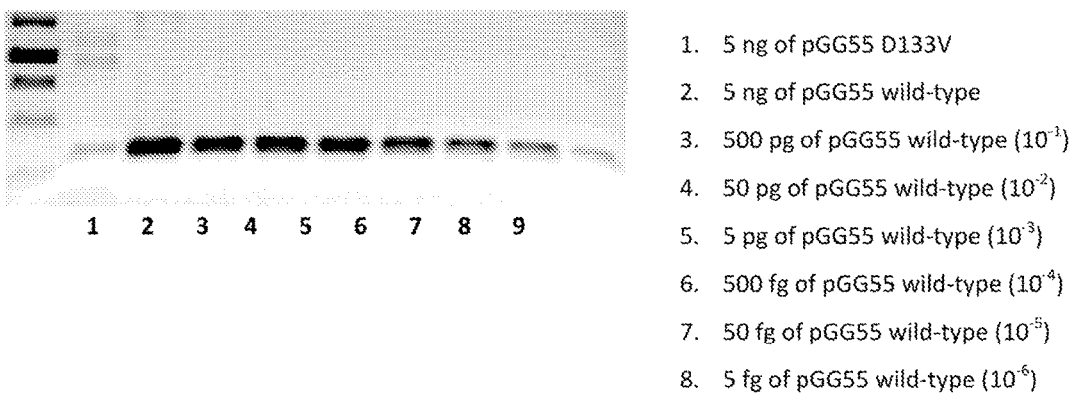
FIG. 17. Sensitivity of the PCR reaction to detect the wild-type prfA sequence using the primer ADV452 and 5 ng as the initial amount of DNA.
Figure 18:
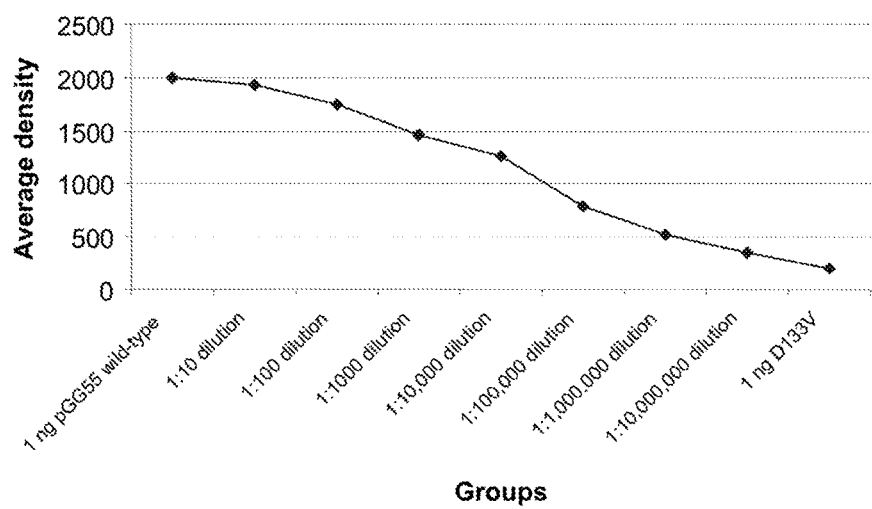
FIG. 18. Average density of the bands from the PCR depicted in FIG. 16.
Figure 19:
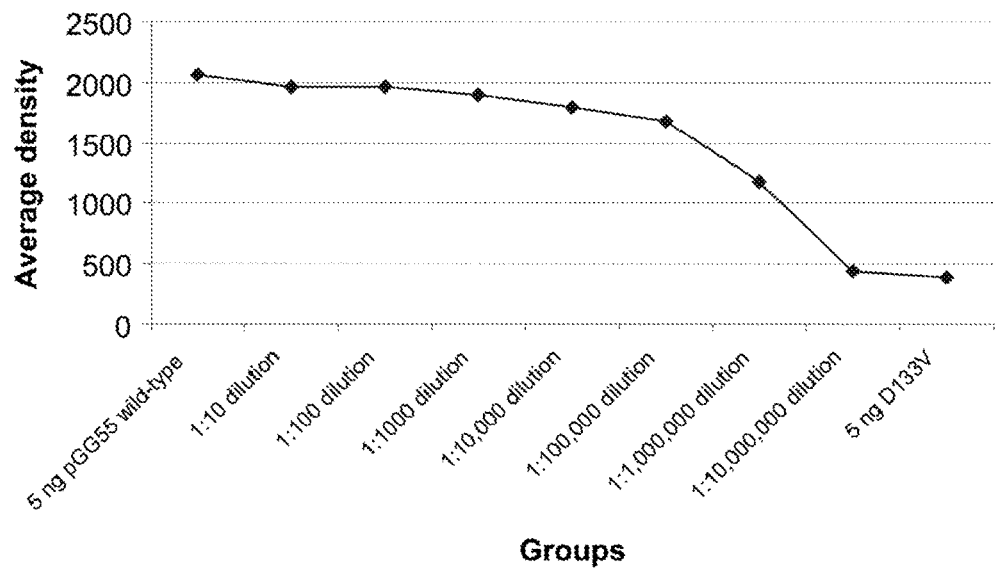
FIG. 19. Average density of the bands from the PCR depicted in FIG. 17.
Figure 20:
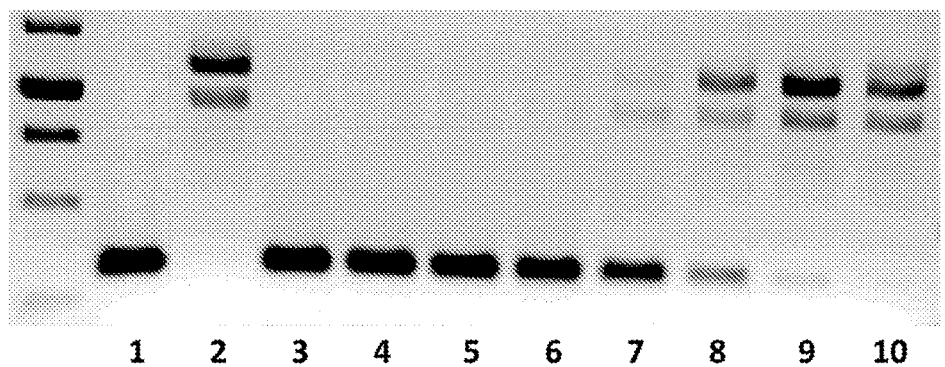
FIG. 20. Validation of the PCR reaction to detect the wild-type prfA sequence using the primer ADV452.
Figure 21:
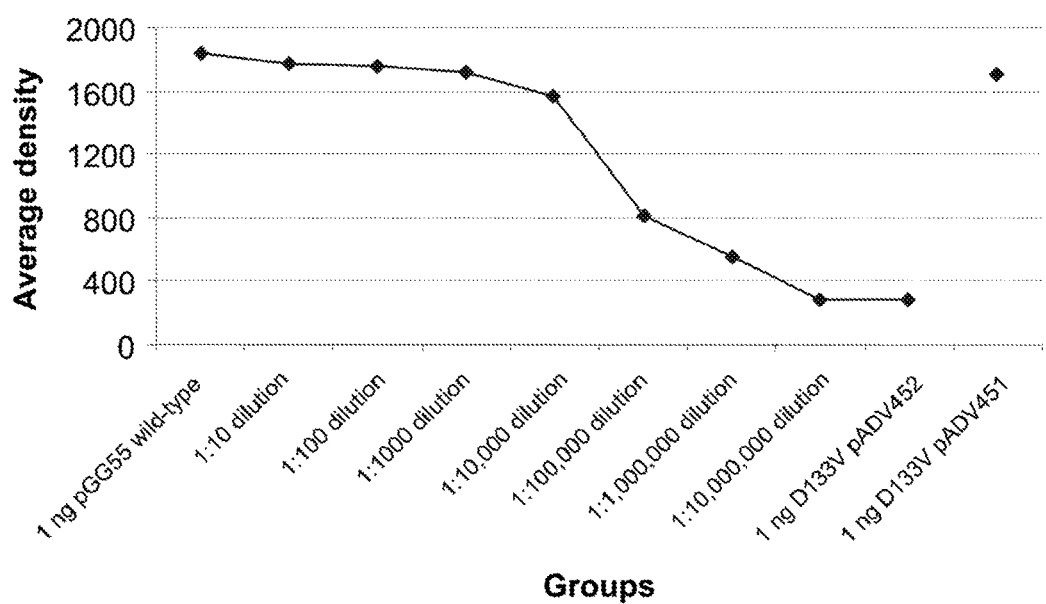
FIG. 21. Average density of the bands from the PCR depicted in FIG. 16.

The sensitivity of the reaction was tested using 1 ng of template DNA. For the plasmid carrying the wild-type pifA sequence, decreasing amounts of DNA (corresponding to 10-fold dilutions from $10^{-1}$ to $10^{-7}$), were also included in the reaction to estimate the sensitivity. In these reactions only the primers ADV452 and ADV453 were used. In a PCR reaction with 30 cycles (10 cycles with annealing temperature of 53° C. and an additional 20 cycles with annealing temperature of 50° C.), the sensitivity of the method was 1 in 100,000 (data not shown). As shown in FIG. 5, increasing the number of PCR cycles to 37 improved the visual sensitivity of the method to $10^{-6}$ for the detection of D133V revertants, without significantly compromising the specificity. A clear band was visible at the $10^{-6}$ dilution, corresponding to a detection level of 1 copy of the wild-type sequence in a million of the D133V mutant, when 1 ng of plasmid was used as the initial amount of DNA. Only a very weak band can be visualized in lanes 1 and 9 after longer exposure, reassuring the robust specificity of the method. On the other hand, when starting with 5 ng of DNA, a band could be easily detected at the $10^{-7}$ dilution, increasing the sensitivity of the PCR. However, a similar band in intensity could also be detected with the pGG55 D133V plasmid, indicating the specificity limit of the method (FIG. 17). This band observed with the pGG55 D133V plasmid is likely due to non-specific amplification of the D133V mutation with primer ADV452 that can significantly accumulate with the increased number of cycles. These results indicate that the sensitivity limit for this method, without significantly compromising the specificity, is situated between 1 to 1,000,000 and 1 to 10,000, 000.

Example 10: Recombinant *Listeria* Expressing a Fusion Protein of LLO to E7 (LM-LLO-E7)

This strain is approx. 4-5 logs more attenuated than the wild-type parent strain 10403S and secretes the fusion protein tLLO-E7. This immunotherapy is based on the backbone XFL7, which is derived from 10403S by the irreversible deletion in the virulence gene transcription activator prfA. PrfA regulates the transcription of several virulence genes such as Listeriolysin O (LLO), ActA, PlcA (phospholipase A), PlcB (phospholipase B) etc that are required for in vivo intracellular growth and survival of *L. monocytogenes*. The plasmid pGG55 is retained by the Lm-LLO-E7 in vitro by means of selection with 'chloramphenicol'. However for in vivo retention of the plasmid by Lm-LLO-E7, it carries a copy of mutated prfA (D133V), which has been demonstrated to be less active than wild-type PrfA in DNA binding and activating the transcription of virulence genes. We have observed that complementation with mutated prfA resulted in approx. 40 fold reduction in the amount of secreted LLO from Lm-LLO-E7 when compared to wild-type strain 10403S. This implicates that the strain Lm-LLO-E7 likely exhibits a reduced expression of the virulence genes that are regulated by PrfA such as actA, inlA, inlB, inlC, plcB etc. In Lm-LLO-E7, the complementation with mutated copy of prfA likely causes a reduction in the expression of different virulence genes that are regulated by PrfA resulting in overall attenuation of approx. 4-5 logs.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed:

1. A recombinant *Listeria* strain, said recombinant *Listeria* strain comprising an episomal plasmid comprising a recombinant nucleic acid, said nucleic acid comprising a first open reading frame encoding a recombinant polypeptide comprising an N-terminal fragment of a listerioly sin O (LLO) protein fused to a heterologous antigen, and wherein said recombinant nucleic acid further comprises a second open reading frame encoding a mutant PrfA protein comprising an amino acid sequence of SEQ ID NO: 34.

2. The recombinant *Listeria* of claim 1, wherein said *Listeria* comprises a deletion, inactivation or mutation in the prfA gene.

3. The recombinant *Listeria* of claim 1, wherein said mutant PrfA protein encoded by said second open reading frame complements said prfA genomic mutation, deletion or inactivation in said *Listeria* strain or restores partial PrfA function in said *Listeria* strain.

4. The recombinant *Listeria* of claim 1, wherein said heterologous antigen is Human Papilloma Virus-E7 (HPV-E7) or HPV-E6.

5. The recombinant *Listeria* strain of claim 1, wherein said N-terminal fragment of an LLO protein is selected from a sequence comprising SEQ ID NO: 2 or SEQ ID NO: 4.

6. The recombinant *Listeria* strain of claim 1, wherein said recombinant *Listeria* strain is a recombinant *Listeria monocytogenes* strain.

7. The recombinant *Listeria* of claim 1, wherein said plasmid comprises a gene encoding a metabolic enzyme.

8. A pharmaceutical composition comprising the recombinant *Listeria* of claim 1 and a pharmaceutically acceptable excipient.

9. A method of inducing an immune response against a tumor or a cancer in a human subject, the method comprising the step of administering to said subject a recombinant *Listeria* strain comprising an episomal plasmid comprising a recombinant nucleic acid, said nucleic acid comprising a first open reading frame encoding a recombinant polypeptide comprising an N-terminal fragment of a listerioly sin O (LLO) protein fused to a heterologous antigen, wherein said recombinant nucleic acid further comprises a second open reading frame encoding a mutant PrfA protein comprising an amino acid sequence of SEQ ID NO:34, thereby inducing an immune response against a tumor or a cancer.

10. The method of claim 9, wherein said *Listeria* comprises a deletion, inactivation or mutation in the prfA gene.

11. The method of claim 9, wherein said mutant PrfA protein encoded by said second open reading frame complements a prfA genomic mutation, deletion or inactivation in said *Listeria* strain or restores partial PrfA function in said *Listeria* strain.

12. The method of claim 9, wherein said administering is intravenous or oral administering.

13. The method of claim 9, wherein said heterologous antigen is Human Papilloma Virus-E7 (HPV-E7) or HPV-E6.

14. The method of claim 9, wherein said N-terminal fragment of an LLO protein is selected from a sequence comprising SEQ ID NO: 2 or SEQ ID NO: 4.

15. The method of claim 9, wherein said recombinant *Listeria* strain is administered to said human subject at a dose of $1\times10^9$-$3.31\times10^{10}$ organisms.

16. The method of claim 15, wherein said recombinant *Listeria* strain is stored in a frozen or lyophilized condition prior to administering.

17. The method of claim 9, wherein said recombinant *Listeria* strain is a recombinant *Listeria monocytogenes* strain.

18. The method of claim 9, wherein said plasmid comprises a gene encoding a metabolic enzyme.

19. The method of claim 9, further comprising the step of boosting said human subject with said recombinant *Listeria* strain.

20. The method of claim 9, wherein said immune response is a cytotoxic T cell anti-tumor immune response.

21. The method of claim 9, wherein said method allows protecting a subject against a tumor or cancer.

22. The method of claim 9, wherein said method allows treating a subject against a tumor or cancer.

23. The method of claim 22, wherein said cancer is cervical cancer, head and neck cancer (HNC) or anal cancer.

24. The recombinant *Listeria* of claim 2, wherein said heterologous antigen is Human Papilloma Virus-E7 (HPV-E7) or Human Papilloma Virus-E6 (HPV-E6).

25. The recombinant *Listeria* of claim 4, wherein said heterologous antigen is Human Papilloma Virus-E7 (HPV-E7).

26. The recombinant *Listeria* of claim 4, wherein said heterologous antigen is Human Papilloma Virus-E6 (HPV-E6).

27. The method of claim 13, wherein said heterologous antigen is Human Papilloma Virus-E7 (HPV-E7).

28. The method of claim 13, wherein said heterologous antigen is Human Papilloma Virus-E6 (HPV-E6).

29. The recombinant *Listeria* of claim 1, wherein said mutant PrfA protein is encoded by SEQ ID NO: 33.

30. The recombinant *Listeria* of claim 25, wherein said HPV-E7 is from HPV16.

31. The method of claim 9, wherein said mutant PrfA protein is encoded by SEQ ID NO: 33.

32. The method of claim 27, wherein said HPV-E7 is from HPV16.

* * * * *

SEQUENCE LISTING

```
<160> NUMBER OF SEQ ID NOS: 36

<210> SEQ ID NO 1
<211> LENGTH: 32
<212> TYPE: PRT
<213> ORGANISM: Listeria monocytogenes

<400> SEQUENCE: 1

Lys Glu Asn Ser Ile Ser Ser Met Ala Pro Pro Ala Ser Pro Pro Ala
1               5                   10                  15
```

Ser Pro Lys Thr Pro Ile Glu Lys His Ala Asp Glu Ile Asp Lys
         20                  25                  30

<210> SEQ ID NO 2
<211> LENGTH: 441
<212> TYPE: PRT
<213> ORGANISM: Listeria monocytogenes

<400> SEQUENCE: 2

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Val Ala Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Ser Asn Val Ser Ala Lys Ile Asp Tyr Asp Asp
        195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
            340                 345                 350

Lys Asp Glu Val Gln Ile Ile Asp Gly Asn Leu Gly Asp Leu Arg Asp
        355                 360                 365

```
Ile Leu Lys Lys Gly Ala Thr Phe Asn Arg Glu Thr Pro Gly Val Pro
        370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

Gly Lys Ile Asn Ile Asp His Ser Gly Gly Tyr Val Ala Gln Phe Asn
                420                 425                 430

Ile Ser Trp Asp Glu Val Asn Tyr Asp
        435                 440

<210> SEQ ID NO 3
<211> LENGTH: 529
<212> TYPE: PRT
<213> ORGANISM: Listeria monocytogenes

<400> SEQUENCE: 3

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
                20                  25                  30

Glu Asn Ser Ile Ser Ser Met Ala Pro Pro Ala Ser Pro Pro Ala Ser
            35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Lys Ser Ile Asn Gln Asn Asn
                100                 105                 110

Ala Asp Ile Gln Val Val Asn Ala Ile Ser Ser Leu Thr Tyr Pro Gly
            115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
                180                 185                 190

Tyr Ala Gln Ala Tyr Pro Asn Val Ser Ala Lys Ile Asp Tyr Asp Asp
            195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Glu Val Ile Ser Phe Lys Gln Ile Tyr Tyr
                245                 250                 255

Asn Val Asn Val Asn Glu Pro Thr Arg Pro Ser Arg Phe Phe Gly Lys
                260                 265                 270

Ala Val Thr Lys Glu Gln Leu Gln Ala Leu Gly Val Asn Ala Glu Asn
            275                 280                 285

Pro Pro Ala Tyr Ile Ser Ser Val Ala Tyr Gly Arg Gln Val Tyr Leu
```

```
                290                 295                 300
Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
                340                 345                 350

Lys Asp Glu Val Gln Ile Ile Asp Gly Asn Leu Gly Asp Leu Arg Asp
                355                 360                 365

Ile Leu Lys Lys Gly Ala Thr Phe Asn Arg Glu Thr Pro Gly Val Pro
370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

Gly Lys Ile Asn Ile Asp His Ser Gly Gly Tyr Val Ala Gln Phe Asn
                420                 425                 430

Ile Ser Trp Asp Glu Val Asn Tyr Asp Pro Glu Gly Asn Glu Ile Val
                435                 440                 445

Gln His Lys Asn Trp Ser Glu Asn Asn Lys Ser Lys Leu Ala His Phe
                450                 455                 460

Thr Ser Ser Ile Tyr Leu Pro Gly Asn Ala Arg Asn Ile Asn Val Tyr
465                 470                 475                 480

Ala Lys Glu Cys Thr Gly Leu Ala Trp Glu Trp Trp Arg Thr Val Ile
                485                 490                 495

Asp Asp Arg Asn Leu Pro Leu Val Lys Asn Arg Asn Ile Ser Ile Trp
                500                 505                 510

Gly Thr Thr Leu Tyr Pro Lys Tyr Ser Asn Lys Val Asp Asn Pro Ile
                515                 520                 525

Glu

<210> SEQ ID NO 4
<211> LENGTH: 416
<212> TYPE: PRT
<213> ORGANISM: Listeria monocytogenes

<400> SEQUENCE: 4

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
                20                  25                  30

Glu Asn Ser Ile Ser Ser Val Ala Pro Pro Ala Ser Pro Pro Ala Ser
                35                  40                  45

Pro Lys Thr Pro Ile Glu Lys Lys His Ala Asp Glu Ile Asp Lys Tyr
                50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
                100                 105                 110

Ala Asp Ile Gln Val Val Asn Ala Ile Ser Ser Leu Thr Tyr Pro Gly
                115                 120                 125

Ala Leu Val Lys Ala Asn Ser Glu Leu Val Glu Asn Gln Pro Asp Val
```

```
                130               135               140
Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Ser Asn Val Ser Ala Lys Ile Asp Tyr Asp Asp
        195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
            340                 345                 350

Lys Asp Glu Val Gln Ile Ile Asp Gly Asn Leu Gly Asp Leu Arg Asp
        355                 360                 365

Ile Leu Lys Lys Gly Ala Thr Phe Asn Arg Glu Thr Pro Gly Val Pro
370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415
```

<210> SEQ ID NO 5
<211> LENGTH: 390
<212> TYPE: PRT
<213> ORGANISM: Listeria monocytogenes

<400> SEQUENCE: 5

```
Met Arg Ala Met Met Val Val Phe Ile Thr Ala Asn Cys Ile Thr Ile
1               5                   10                  15

Asn Pro Asp Ile Ile Phe Ala Ala Thr Asp Ser Glu Asp Ser Ser Leu
                20                  25                  30

Asn Thr Asp Glu Trp Glu Glu Glu Lys Thr Glu Glu Gln Pro Ser Glu
            35                  40                  45

Val Asn Thr Gly Pro Arg Tyr Glu Thr Ala Arg Glu Val Ser Ser Arg
        50                  55                  60

Asp Ile Lys Glu Leu Glu Lys Ser Asn Lys Val Arg Asn Thr Asn Lys
65                  70                  75                  80

Ala Asp Leu Ile Ala Met Leu Lys Glu Lys Ala Glu Lys Gly Pro Asn
                85                  90                  95
```

```
Ile Asn Asn Asn Asn Ser Glu Gln Thr Glu Asn Ala Ala Ile Asn Glu
            100                 105                 110

Glu Ala Ser Gly Ala Asp Arg Pro Ala Ile Gln Val Glu Arg Arg His
        115                 120                 125

Pro Gly Leu Pro Ser Asp Ser Ala Ala Glu Ile Lys Lys Arg Arg Lys
    130                 135                 140

Ala Ile Ala Ser Ser Asp Ser Glu Leu Glu Ser Leu Thr Tyr Pro Asp
145                 150                 155                 160

Lys Pro Thr Lys Val Asn Lys Lys Val Ala Lys Glu Ser Val Ala
                165                 170                 175

Asp Ala Ser Glu Ser Asp Leu Asp Ser Ser Met Gln Ser Ala Asp Glu
            180                 185                 190

Ser Ser Pro Gln Pro Leu Lys Ala Asn Gln Gln Pro Phe Phe Pro Lys
        195                 200                 205

Val Phe Lys Lys Ile Lys Asp Ala Gly Lys Trp Val Arg Asp Lys Ile
    210                 215                 220

Asp Glu Asn Pro Glu Val Lys Lys Ala Ile Val Asp Lys Ser Ala Gly
225                 230                 235                 240

Leu Ile Asp Gln Leu Leu Thr Lys Lys Lys Ser Glu Glu Val Asn Ala
                245                 250                 255

Ser Asp Phe Pro Pro Pro Thr Asp Glu Glu Leu Arg Leu Ala Leu
            260                 265                 270

Pro Glu Thr Pro Met Leu Leu Gly Phe Asn Ala Pro Ala Thr Ser Glu
        275                 280                 285

Pro Ser Ser Phe Glu Phe Pro Pro Pro Thr Asp Glu Glu Leu Arg
    290                 295                 300

Leu Ala Leu Pro Glu Thr Pro Met Leu Leu Gly Phe Asn Ala Pro Ala
305                 310                 315                 320

Thr Ser Glu Pro Ser Ser Phe Glu Phe Pro Pro Pro Thr Glu Asp
                325                 330                 335

Glu Leu Glu Ile Ile Arg Glu Thr Ala Ser Ser Leu Asp Ser Ser Phe
            340                 345                 350

Thr Arg Gly Asp Leu Ala Ser Leu Arg Asn Ala Ile Asn Arg His Ser
        355                 360                 365

Gln Asn Phe Ser Asp Phe Pro Pro Ile Pro Thr Glu Glu Leu Asn
    370                 375                 380

Gly Arg Gly Gly Arg Pro
385                 390

<210> SEQ ID NO 6
<211> LENGTH: 1170
<212> TYPE: DNA
<213> ORGANISM: Listeria monocytogenes

<400> SEQUENCE: 6
atgcgtgcga tgatggtggt tttcattact gccaattgca ttacgattaa ccccgacata      60
atatttgcag cgacagatag cgaagattct agtctaaaca cagatgaatg ggaagaagaa     120
aaaacagaag agcaaccaag cgaggtaaat acgggaccaa gatacgaaac tgcacgtgaa     180
gtaagttcac gtgatattaa agaactagaa aaatcgaata agtgagaaa tacgaacaaa     240 gcagacctaa tagcaatgtt gaaagaaaaa gcagaaaaag gtccaaatat caataataac     300
aacagtgaac aaactgagaa tgcggctata aatgagagg cttcaggagc cgaccgacca     360
gctatacaag tggagcgtcg tcatccagga ttgccatcgg atagcgcagc ggaaattaaa     420
```

-continued

```
aaaagaagga aagccatagc atcatcggat agtgagcttg aaagccttac ttatccggat    480
aaaccaacaa aagtaaataa gaaaaaagtg gcgaaagagt cagttgcgga tgcttctgaa    540
agtgacttag attctagcat gcagtcagca gatgagtctt caccacaacc tttaaaagca    600
aaccaacaac cattttttccc taaagtattt aaaaaaataa agatgcggg gaaatgggta    660 cgtgataaaa tcgacgaaaa tcctgaagta agaaagcga ttgttgataa aagtgcaggg    720
ttaattgacc aattattaac caaaagaaa agtgaagagg taaatgcttc ggacttcccg    780
ccaccaccta cggatgaaga gttaagactt gctttgccag agacaccaat gcttcttggt    840
tttaatgctc ctgctacatc agaaccgagc tcattcgaat tccaccacc acctacggat    900 gaagagttaa gacttgcttt gccagagacg ccaatgcttc ttggttttaa tgctcctgct    960
acatcggaac cgagctcgtt cgaatttcca ccgcctccaa cagaagatga actagaaatc   1020
atccgggaaa cagcatcctc gctagattct agttttacaa gaggggattt agctagtttg   1080
agaaatgcta ttaatcgcca tagtcaaaat ttctctgatt tcccaccaat cccaacagaa   1140
gaagagttga acgggagagg cggtagacca                                    1170
```

<210> SEQ ID NO 7
<211> LENGTH: 14
<212> TYPE: PRT
<213> ORGANISM: Listeria monocytogenes

<400> SEQUENCE: 7

Lys Thr Glu Glu Gln Pro Ser Glu Val Asn Thr Gly Pro Arg
1               5                   10

<210> SEQ ID NO 8
<211> LENGTH: 28
<212> TYPE: PRT
<213> ORGANISM: Listeria monocytogenes

<400> SEQUENCE: 8

Lys Ala Ser Val Thr Asp Thr Ser Glu Gly Asp Leu Asp Ser Ser Met
1               5                   10                  15

Gln Ser Ala Asp Glu Ser Thr Pro Gln Pro Leu Lys
            20                  25

<210> SEQ ID NO 9
<211> LENGTH: 20
<212> TYPE: PRT
<213> ORGANISM: Listeria monocytogenes

<400> SEQUENCE: 9

Lys Asn Glu Glu Val Asn Ala Ser Asp Phe Pro Pro Pro Pro Thr Asp
1               5                   10                  15

Glu Glu Leu Arg
            20

<210> SEQ ID NO 10
<211> LENGTH: 33
<212> TYPE: PRT
<213> ORGANISM: Listeria monocytogenes

<400> SEQUENCE: 10

Arg Gly Gly Ile Pro Thr Ser Glu Glu Phe Ser Ser Leu Asn Ser Gly
1               5                   10                  15

Asp Phe Thr Asp Asp Glu Asn Ser Glu Thr Thr Glu Glu Glu Ile Asp
            20                  25                  30

Arg

```
<210> SEQ ID NO 11
<211> LENGTH: 17
<212> TYPE: PRT
<213> ORGANISM: Streptococcus sp. G148

<400> SEQUENCE: 11
```

Lys Gln Asn Thr Ala Ser Thr Glu Thr Thr Thr Thr Asn Glu Gln Pro
1               5                   10                  15

Lys

```
<210> SEQ ID NO 12
<211> LENGTH: 17
<212> TYPE: PRT
<213> ORGANISM: Streptococcus equisimilis

<400> SEQUENCE: 12
```

Lys Gln Asn Thr Ala Asn Thr Glu Thr Thr Thr Thr Asn Glu Gln Pro
1               5                   10                  15

Lys

```
<210> SEQ ID NO 13
<211> LENGTH: 98
<212> TYPE: PRT
<213> ORGANISM: Human papillomavirus type 16

<400> SEQUENCE: 13
```

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
        50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

```
<210> SEQ ID NO 14
<211> LENGTH: 105
<212> TYPE: PRT
<213> ORGANISM: Human papillomavirus type 16

<400> SEQUENCE: 14
```

Met His Gly Pro Lys Ala Thr Leu Gln Asp Ile Val Leu His Leu Glu
1               5                   10                  15

Pro Gln Asn Glu Ile Pro Val Asp Leu Leu Cys His Glu Gln Leu Ser
                20                  25                  30

Asp Ser Glu Glu Glu Asn Asp Glu Ile Asp Gly Val Asn His Gln His
            35                  40                  45

Leu Pro Ala Arg Arg Ala Glu Pro Gln Arg His Thr Met Leu Cys Met
        50                  55                  60

Cys Cys Lys Cys Glu Ala Arg Ile Glu Leu Val Val Glu Ser Ser Ala
65                  70                  75                  80

```
Asp Asp Leu Arg Ala Phe Gln Gln Leu Phe Leu Asn Thr Leu Ser Phe
            85                  90                  95

Val Cys Pro Trp Cys Ala Ser Gln Gln
            100                 105
```

<210> SEQ ID NO 15
<211> LENGTH: 158
<212> TYPE: PRT
<213> ORGANISM: Human papillomavirus type 16

<400> SEQUENCE: 15

```
Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
                20                  25                  30

Ile Ile Leu Glu Cys Val Tyr Cys Lys Gln Gln Leu Leu Arg Arg Glu
            35                  40                  45

Val Tyr Asp Phe Ala Phe Arg Asp Leu Cys Ile Val Tyr Arg Asp Gly
        50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
    130                 135                 140

Ser Cys Cys Arg Ser Ser Arg Thr Arg Glu Thr Gln Leu
145                 150                 155
```

<210> SEQ ID NO 16
<211> LENGTH: 158
<212> TYPE: PRT
<213> ORGANISM: Human papillomavirus type 16

<400> SEQUENCE: 16

```
Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys
                20                  25                  30

Val Tyr Cys Lys Thr Val Leu Glu Leu Thr Glu Val Phe Glu Phe Ala
            35                  40                  45

Phe Lys Asp Leu Phe Val Val Tyr Arg Asp Ser Ile Pro His Ala Ala
        50                  55                  60

Cys His Lys Cys Ile Asp Phe Tyr Ser Arg Ile Arg Glu Leu Arg His
65                  70                  75                  80

Tyr Ser Asp Ser Val Tyr Gly Asp Thr Leu Glu Lys Leu Thr Asn Thr
                85                  90                  95

Gly Leu Tyr Asn Leu Leu Ile Arg Cys Leu Arg Cys Gln Lys Pro Leu
            100                 105                 110

Asn Pro Ala Glu Lys Leu Arg His Leu Asn Glu Lys Arg Arg Phe His
        115                 120                 125

Asn Ile Ala Gly His Tyr Arg Gly Gln Cys His Ser Cys Cys Asn Arg
    130                 135                 140
```

Ala Arg Gln Glu Arg Leu Gln Arg Arg Arg Glu Thr Gln Val
145                 150                 155

<210> SEQ ID NO 17
<211> LENGTH: 22
<212> TYPE: DNA
<213> ORGANISM: Artificial Sequence
<220> FEATURE:
<223> OTHER INFORMATION: Primer

<400> SEQUENCE: 17
ggctcgagca tggagataca cc                                         22

<210> SEQ ID NO 18
<211> LENGTH: 28
<212> TYPE: DNA
<213> ORGANISM: Artificial Sequence
<220> FEATURE:
<223> OTHER INFORMATION: Primer

<400> SEQUENCE: 18
ggggactagt ttatggtttc tgagaaca                                   28

<210> SEQ ID NO 19
<211> LENGTH: 31
<212> TYPE: DNA
<213> ORGANISM: Artificial Sequence
<220> FEATURE:
<223> OTHER INFORMATION: Primer

<400> SEQUENCE: 19
gggggctagc cctcctttga ttagtatatt c                               31

<210> SEQ ID NO 20
<211> LENGTH: 28
<212> TYPE: DNA
<213> ORGANISM: Artificial Sequence
<220> FEATURE:
<223> OTHER INFORMATION: Primer

<400> SEQUENCE: 20
ctccctcgag atcataattt acttcatc                                   28

<210> SEQ ID NO 21
<211> LENGTH: 27
<212> TYPE: DNA
<213> ORGANISM: Artificial Sequence
<220> FEATURE:
<223> OTHER INFORMATION: Primer

<400> SEQUENCE: 21
cccgtcgacc agctcttctt ggtgaag                                    27

<210> SEQ ID NO 22
<211> LENGTH: 25
<212> TYPE: DNA
<213> ORGANISM: Artificial Sequence
<220> FEATURE:
<223> OTHER INFORMATION: Primer

<400> SEQUENCE: 22
gcggatccca tggagataca cctac                                      25

<210> SEQ ID NO 23
<211> LENGTH: 22
<212> TYPE: DNA

```
<213> ORGANISM: Artificial Sequence
<220> FEATURE:
<223> OTHER INFORMATION: Primer

<400> SEQUENCE: 23
gctctagatt atggtttctg ag                                            22

<210> SEQ ID NO 24
<211> LENGTH: 9
<212> TYPE: PRT
<213> ORGANISM: Human papillomavirus type 16

<400> SEQUENCE: 24

Arg Ala His Tyr Asn Ile Val Thr Phe
1               5

<210> SEQ ID NO 25
<211> LENGTH: 9
<212> TYPE: PRT
<213> ORGANISM: Human immunodeficiency virus

<400> SEQUENCE: 25

Ala Met Gln Met Leu Lys Glu Thr Ile
1               5

<210> SEQ ID NO 26
<211> LENGTH: 9
<212> TYPE: PRT
<213> ORGANISM: Listeria monocytogenes

<400> SEQUENCE: 26

Gly Tyr Lys Asp Gly Asn Glu Tyr Ile
1               5

<210> SEQ ID NO 27
<211> LENGTH: 55
<212> TYPE: DNA
<213> ORGANISM: Artificial Sequence
<220> FEATURE:
<223> OTHER INFORMATION: Primer

<400> SEQUENCE: 27
gactacaagg acgatgaccg acaagtgata acccgggatc taaataaatc cgttt        55

<210> SEQ ID NO 28
<211> LENGTH: 18
<212> TYPE: DNA
<213> ORGANISM: Artificial Sequence
<220> FEATURE:
<223> OTHER INFORMATION: ADV451 forward primer for amplification of prfA
      gene and discernment of D133V mutation

<400> SEQUENCE: 28
cctagctaaa tttaatgt                                                 18

<210> SEQ ID NO 29
<211> LENGTH: 18
<212> TYPE: DNA
<213> ORGANISM: Artificial Sequence
<220> FEATURE:
<223> OTHER INFORMATION: ADV452 forward primer for amplification of prfA
      gene

<400> SEQUENCE: 29
cctagctaaa tttaatga                                                 18
```

<210> SEQ ID NO 30
<211> LENGTH: 21
<212> TYPE: DNA
<213> ORGANISM: Artificial Sequence
<220> FEATURE:
<223> OTHER INFORMATION: ADV453 reverse primer for amplification of prfA
      gene

<400> SEQUENCE: 30
taattttccc caagtagcag g                                              21

<210> SEQ ID NO 31
<211> LENGTH: 714
<212> TYPE: DNA
<213> ORGANISM: Listeria monocytogenes

<400> SEQUENCE: 31
atgaacgctc aagcagaaga attcaaaaaa tatttagaaa ctaacgggat aaaaccaaaa     60
caatttcata aaaagaact tatttttaac caatgggatc cacaagaata ttgtattttt     120
ctatatgatg gtatcacaaa gctcacgagt attagcgaga acgggaccat catgaattta    180
caatactaca aaggggcttt cgttataatg tctggcttta ttgatacaga aacatcggtt    240
ggctattata atttagaagt cattagcgag caggctaccg catacgttat caaaataaac    300
gaactaaaag aactactgag caaaaatctt acgcactttt tctatgtttt ccaaccccta    360
caaaaacaag tttcatacag cctagctaaa tttaatgatt tttcgattaa cgggaagctt    420
ggctctattt gcggtcaact tttaatcctg acctatgtgt atggtaaaga aactcctgat    480
ggcatcaaga ttacactgga taatttaaca atgcaggagt taggatattc aagtggcatc    540
gcacatagct cagctgttag cagaattatt tccaaattaa agcaagagaa agttatcgtg    600
tataaaaatt catgctttta tgtacaaaat cttgattatc tcaaaagata tgcccctaaa    660
ttagatgaat ggttttatt agcatgtcct gctacttggg gaaaattaaa ttaa            714

<210> SEQ ID NO 32
<211> LENGTH: 237
<212> TYPE: PRT
<213> ORGANISM: Listeria monocytogenes

<400> SEQUENCE: 32

Met Asn Ala Gln Ala Glu Glu Phe Lys Lys Tyr Leu Glu Thr Asn Gly
1               5                   10                  15

Ile Lys Pro Lys Gln Phe His Lys Lys Glu Leu Ile Phe Asn Gln Trp
            20                  25                  30

Asp Pro Gln Glu Tyr Cys Ile Phe Leu Tyr Asp Gly Ile Thr Lys Leu
        35                  40                  45

Thr Ser Ile Ser Glu Asn Gly Thr Ile Met Asn Leu Gln Tyr Tyr Lys
    50                  55                  60

Gly Ala Phe Val Ile Met Ser Gly Phe Ile Asp Thr Glu Thr Ser Val
65                  70                  75                  80

Gly Tyr Tyr Asn Leu Glu Val Ile Ser Glu Gln Ala Thr Ala Tyr Val
                85                  90                  95

Ile Lys Ile Asn Glu Leu Lys Glu Leu Leu Ser Lys Asn Leu Thr His
            100                 105                 110

Phe Phe Tyr Val Phe Gln Thr Leu Gln Lys Gln Val Ser Tyr Ser Leu
        115                 120                 125

Ala Lys Phe Asn Asp Phe Ser Ile Asn Gly Lys Leu Gly Ser Ile Cys
    130                 135                 140

Gly Gln Leu Leu Ile Leu Thr Tyr Val Tyr Gly Lys Glu Thr Pro Asp
145                 150                 155                 160

Gly Ile Lys Ile Thr Leu Asp Asn Leu Thr Met Gln Glu Leu Gly Tyr
                165                 170                 175

Ser Ser Gly Ile Ala His Ser Ser Ala Val Ser Arg Ile Ile Ser Lys
            180                 185                 190

Leu Lys Gln Glu Lys Val Ile Val Tyr Lys Asn Ser Cys Phe Tyr Val
        195                 200                 205

Gln Asn Leu Asp Tyr Leu Lys Arg Tyr Ala Pro Lys Leu Asp Glu Trp
    210                 215                 220

Phe Tyr Leu Ala Cys Pro Ala Thr Trp Gly Lys Leu Asn
225                 230                 235

<210> SEQ ID NO 33
<211> LENGTH: 714
<212> TYPE: DNA
<213> ORGANISM: Listeria monocytogenes

<400> SEQUENCE: 33

```
atgaacgctc aagcagaaga attcaaaaaa tatttagaaa ctaacgggat aaaaccaaaa      60
caatttcata aaaagaact tattttaac caatgggatc cacaagaata ttgtattttt      120
ctatatgatg gtatcacaaa gctcacgagt attagcgaga acgggaccat catgaattta     180
caatactaca aggggctttt cgttataatg tctggcttta ttgatacaga aacatcggtt     240
ggctattata atttagaagt cattagcgag caggctaccg catacgttat caaaataaac     300
gaactaaaag aactactgag caaaaatctt acgcactttt tctatgtttt ccaaacccta     360
caaaaacaag tttcatacag cctagctaaa tttaatgttt tttcgattaa cgggaagctt     420
ggctctattt gcggtcaact tttaatcctg acctatgtgt atggtaaaga aactcctgat     480
ggcatcaaga ttacactgga taatttaaca atgcaggagt taggatattc aagtggcatc     540
gcacatagct cagctgttag cagaattatt ccaaattaa agcaagagaa agttatcgtg     600
tataaaaatt catgctttta tgtacaaaat cgtgattatc tcaaaagata tgcccctaaa     660
ttagatgaat ggttttattt agcatgtcct gctacttggg gaaaattaaa ttaa          714
```

<210> SEQ ID NO 34
<211> LENGTH: 237
<212> TYPE: PRT
<213> ORGANISM: Listeria monocytogenes

<400> SEQUENCE: 34

Met Asn Ala Gln Ala Glu Glu Phe Lys Lys Tyr Leu Glu Thr Asn Gly
1               5                   10                  15

Ile Lys Pro Lys Gln Phe His Lys Lys Glu Leu Ile Phe Asn Gln Trp
            20                  25                  30

Asp Pro Gln Glu Tyr Cys Ile Phe Leu Tyr Asp Gly Ile Thr Lys Leu
        35                  40                  45

Thr Ser Ile Ser Glu Asn Gly Thr Ile Met Asn Leu Gln Tyr Tyr Lys
    50                  55                  60

Gly Ala Phe Val Ile Met Ser Gly Phe Ile Asp Thr Glu Thr Ser Val
65                  70                  75                  80

Gly Tyr Tyr Asn Leu Glu Val Ile Ser Glu Gln Ala Thr Ala Tyr Val
                85                  90                  95

Ile Lys Ile Asn Glu Leu Lys Glu Leu Leu Ser Lys Asn Leu Thr His
            100                 105                 110

Phe Phe Tyr Val Phe Gln Thr Leu Gln Lys Gln Val Ser Tyr Ser Leu
            115                 120                 125

Ala Lys Phe Asn Val Phe Ser Ile Asn Gly Lys Leu Gly Ser Ile Cys
        130                 135                 140

Gly Gln Leu Leu Ile Leu Thr Tyr Val Tyr Gly Lys Glu Thr Pro Asp
145                 150                 155                 160

Gly Ile Lys Ile Thr Leu Asp Asn Leu Thr Met Gln Glu Leu Gly Tyr
                165                 170                 175

Ser Ser Gly Ile Ala His Ser Ser Ala Val Ser Arg Ile Ile Ser Lys
            180                 185                 190

Leu Lys Gln Glu Lys Val Ile Val Tyr Lys Asn Ser Cys Phe Tyr Val
        195                 200                 205

Gln Asn Arg Asp Tyr Leu Lys Arg Tyr Ala Pro Lys Leu Asp Glu Trp
    210                 215                 220

Phe Tyr Leu Ala Cys Pro Ala Thr Trp Gly Lys Leu Asn
225                 230                 235

<210> SEQ ID NO 35
<211> LENGTH: 364
<212> TYPE: DNA
<213> ORGANISM: Artificial Sequence
<220> FEATURE:
<223> OTHER INFORMATION: Lovaxin_C_pGG55

<400> SEQUENCE: 35 ccaaaccta caaaaacaag tttcatacag cctagctaaa tttaatgttt tttcgattaa      60
cgggaagctt ggctctattt gcggtcaact tttaatcctg acctatgtgt atggtaaaga    120
aactcctgat ggcatcaaga ttacactgga taatttaaca atgcaggagt taggatattc    180
aagtggcatc gcacatagct cagctgttag cagaattatt ccaaattaa agcaagagaa     240 agttatcgtg tataaaaatt catgctttta tgtacaaaat cgtgattatc tcaaaagata    300
tgcccctaaa ttagatgaat ggttttattt agcatgtcct gctacttggg gaaaattaaa    360
ttaa                                                                364

<210> SEQ ID NO 36
<211> LENGTH: 364
<212> TYPE: DNA
<213> ORGANISM: Listeria monocytogenes

<400> SEQUENCE: 36 ccaaaccta caaaaacaag tttcatacag cctagctaaa tttaatgatt tttcgattaa      60
cgggaagctt ggctctattt gcggtcaact tttaatcctg acctatgtgt atggtaaaga    120
aactcctgat ggcatcaaga ttacactgga taatttaaca atgcaggagt taggatattc    180
aagtggcatc gcacatagct cagctgttag cagaattatt ccaaattaa agcaagagaa     240 agttatcgtg tataaaaatt catgctttta tgtacaaaat cttgattatc tcaaaagata    300
tgcccctaaa ttagatgaat ggttttattt agcatgtcct gctacttggg gaaaattaaa    360
ttaa                                                                364